United States Patent
Ansari et al.

(10) Patent No.: US 11,363,318 B2
(45) Date of Patent: Jun. 14, 2022

(54) DISPLAY INSERTS, OVERLAYS, AND GRAPHICAL USER INTERFACES FOR MULTIMEDIA SYSTEMS

(71) Applicant: KIP PROD P1 LP, New York, NY (US)

(72) Inventors: Amir Ansari, Plano, TX (US); George A. Cowgill, Farmersville, TX (US); Leon E. Nicholls, Plano, TX (US); Atousa Raissyan, Potomac, MD (US); Jude P. Ramayya, Wylie, TX (US); Ramprakash Masina, Plano, TX (US); Alvin R. McQuarters, Euless, TX (US)

(73) Assignee: KIP PROD PI LP, New York, NY (US)

( * ) Notice: Subject to any disclaimer, the term of this patent is extended or adjusted under 35 U.S.C. 154(b) by 0 days.

(21) Appl. No.: 16/115,091

(22) Filed: Aug. 28, 2018

(65) Prior Publication Data

US 2018/0361426 A1    Dec. 20, 2018

Related U.S. Application Data

(60) Division of application No. 15/360,700, filed on Nov. 23, 2016, now Pat. No. 10,069,643, which is a
(Continued)

(51) Int. Cl.
*H04N 21/258* (2011.01)
*H04N 21/6334* (2011.01)
(Continued)

(52) U.S. Cl.
CPC ............ *H04N 21/24* (2013.01); *B05D 1/305* (2013.01); *B05D 3/002* (2013.01); *B05D 3/04* (2013.01);
(Continued)

(58) Field of Classification Search
CPC ............ H04N 21/482; H04N 21/4312; H04N 21/43615; H04N 21/47217;
(Continued)

(56) References Cited

U.S. PATENT DOCUMENTS 2,273,733 A    2/1942 Paddock
2,316,993 A    4/1943 Sherwood
(Continued)

FOREIGN PATENT DOCUMENTS

CN    102500747    11/2011
DE    3002904    8/1980
(Continued)

OTHER PUBLICATIONS

DLNA enables streaming of premium video in connected homes across Europe. (New Products) IPTV Newsletter, v 5, n 10, p. Oct. 4, 2011.
(Continued)

*Primary Examiner* — Pinkal R Chokshi
(74) *Attorney, Agent, or Firm* — Perkins Coie LLP

(57) ABSTRACT

A disclosed digital media device operational at user premises to receive media signals from a media source for presentation via endpoint devices such as a television display. The digital media device can include gateway and digital media management functionality and can be referred to as a gateway and digital media device. The device offers application services obtained over a wide area network and a user premises network. The digital media device may form a composite signal from the media signal and application service information, for example, for a composite audio and/or video signal for television type presentation to the user. The digital media device may receive a selection signal based on the presentation, for transmission to the application service provider device or to the media source. The media
(Continued)

device also offers a GUI presenting a moveable arrangement of icons for selectively accessing application services.

23 Claims, 30 Drawing Sheets

Related U.S. Application Data continuation of application No. 13/793,336, filed on Mar. 11, 2013, now Pat. No. 9,602,880, which is a continuation of application No. 12/521,760, filed as application No. PCT/US2007/019533 on Sep. 7, 2007, now Pat. No. 8,397,264.

(60) Provisional application No. 60/882,862, filed on Dec. 29, 2006, provisional application No. 60/882,865, filed on Dec. 29, 2006.

(51) Int. Cl.
| | | |
|---|---|---|
| *H04N 21/21* | (2011.01) | |
| *H04N 21/482* | (2011.01) | |
| *H04N 21/24* | (2011.01) | |
| *H04N 21/472* | (2011.01) | |
| *H04L 65/102* | (2022.01) | |
| *H04N 21/436* | (2011.01) | |
| *H04N 21/488* | (2011.01) | |
| *H04N 21/238* | (2011.01) | |
| *B05D 1/30* | (2006.01) | |
| *B05D 3/00* | (2006.01) | |
| *B05D 3/04* | (2006.01) | |
| *B29C 59/10* | (2006.01) | |
| *H04N 21/431* | (2011.01) | |
| *H04N 21/422* | (2011.01) | |
| *H04L 12/28* | (2006.01) | |
| *H04N 21/485* | (2011.01) | |
| *C07D 417/12* | (2006.01) | |
| *C07D 417/14* | (2006.01) | |
| *H04L 9/40* | (2022.01) | |
| *H04N 21/4363* | (2011.01) | |

(52) U.S. Cl.
CPC ............ *B29C 59/10* (2013.01); *C07D 417/12* (2013.01); *C07D 417/14* (2013.01); *H04L 12/2807* (2013.01); *H04L 65/102* (2013.01); *H04N 21/238* (2013.01); *H04N 21/25816* (2013.01); *H04N 21/25875* (2013.01); *H04N 21/42204* (2013.01); *H04N 21/4312* (2013.01); *H04N 21/43615* (2013.01); *H04N 21/47217* (2013.01); *H04N 21/482* (2013.01); *H04N 21/485* (2013.01); *H04N 21/4882* (2013.01); *H04N 21/6334* (2013.01); *B05D 3/044* (2013.01); *H04L 63/10* (2013.01); *H04L 2012/2849* (2013.01); *H04N 21/2402* (2013.01); *H04N 21/43637* (2013.01)

(58) Field of Classification Search
CPC ......... H04N 21/43637; H04N 21/4882; H04N 21/42204; H04N 21/25875; H04N 21/25816; H04N 21/6334
See application file for complete search history.

(56) References Cited

U.S. PATENT DOCUMENTS

| | | | |
|---|---|---|---|
| 4,297,607 A | 10/1981 | Lynnworth et al. | |
| 4,467,586 A | 8/1984 | Long | |
| 4,814,552 A | 3/1989 | Stefik et al. | |
| 4,991,148 A | 2/1991 | Gilchrist | |
| 5,339,259 A | 8/1994 | Puma | |
| 5,372,138 A | 12/1994 | Crowley et al. | |
| 5,421,338 A | 6/1995 | Crowley et al. | |
| 5,515,853 A | 5/1996 | Smith et al. | |
| 5,517,579 A | 5/1996 | Baron et al. | |
| 5,524,630 A | 6/1996 | Crowley et al. | |
| 5,588,432 A | 12/1996 | Crowley et al. | |
| 5,673,252 A | 9/1997 | Johnson et al. | |
| 5,715,825 A | 2/1998 | Crowley et al. | |
| 5,750,941 A | 5/1998 | Ishikawa et al. | |
| 5,840,031 A | 11/1998 | Crowley et al. | |
| 5,862,299 A * | 1/1999 | Lee | H04N 21/426 386/253 |
| 5,867,146 A | 2/1999 | Kim et al. | |
| 5,867,666 A | 2/1999 | Harvey | |
| 5,878,223 A | 3/1999 | Becker et al. | |
| 5,943,478 A | 8/1999 | Aggarwal et al. | |
| 5,977,958 A | 11/1999 | Baron et al. | |
| 5,991,739 A | 11/1999 | Cupps et al. | |
| 5,995,272 A | 11/1999 | Werner | |
| 6,004,269 A | 12/1999 | Crowley et al. | |
| 6,016,520 A | 1/2000 | Facq et al. | |
| 6,029,045 A | 2/2000 | Picco | |
| 6,033,150 A | 3/2000 | Culen | |
| 6,039,251 A | 3/2000 | Holowko | |
| 6,055,569 A | 4/2000 | O'Brien et al. | |
| 6,092,114 A | 7/2000 | Shaffer et al. | |
| 6,118,205 A | 9/2000 | Wood et al. | |
| 6,158,483 A | 12/2000 | Trpkovski | |
| 6,228,290 B1 | 5/2001 | Reames et al. | |
| 6,301,609 B1 | 10/2001 | Aravamudan et al. | |
| 6,330,599 B1 | 12/2001 | Harvey | |
| 6,377,571 B1 | 4/2002 | Tai | |
| 6,426,955 B1 | 7/2002 | Dalton | |
| 6,434,158 B1 | 8/2002 | Harris | |
| 6,434,618 B1 | 8/2002 | Cohen | |
| 6,449,344 B1 | 9/2002 | Goldfinger et al. | |
| 6,456,597 B1 | 9/2002 | Bare | |
| 6,457,294 B1 | 10/2002 | Virnelson et al. | |
| 6,487,646 B1 | 11/2002 | Adams et al. | |
| 6,493,128 B1 | 12/2002 | Agrawal et al. | |
| 6,496,575 B1 | 12/2002 | Vasell | |
| 6,526,581 B1 | 2/2003 | Edson | |
| 6,542,506 B1 | 4/2003 | Lee | |
| 6,549,937 B1 | 4/2003 | Auerbach et al. | |
| 6,553,345 B1 | 4/2003 | Kuhn | |
| 6,622,168 B1 | 9/2003 | Datta | |
| 6,631,412 B1 | 10/2003 | Glasser et al. | |
| 6,658,091 B1 | 12/2003 | Naidoo | |
| 6,671,730 B1 | 12/2003 | Akatsu | |
| 6,677,976 B2 | 1/2004 | Parker et al. | |
| 6,681,232 B1 | 1/2004 | Sistanizadeh et al. | |
| 6,694,007 B2 | 2/2004 | Lang et al. | |
| 6,697,474 B1 | 2/2004 | Hanson et al. | |
| 6,731,992 B1 | 5/2004 | Ziegler | |
| 6,735,619 B1 | 5/2004 | Sawada | |
| 6,745,632 B1 | 6/2004 | Dryer et al. | |
| 6,771,006 B2 | 8/2004 | Zioter et al. | |
| 6,798,403 B2 | 9/2004 | Kitada et al. | |
| 6,850,252 B1 | 2/2005 | Hoffberg | |
| 6,850,901 B1 | 2/2005 | Hunter et al. | |
| 6,850,979 B1 | 2/2005 | Saulpaugh et al. | |
| 6,851,054 B2 | 2/2005 | Wheeler | |
| 6,865,150 B1 | 3/2005 | Perkins | |
| 6,868,292 B2 | 3/2005 | Ficco | |
| 6,871,193 B1 | 3/2005 | Campbell et al. | |
| 6,889,321 B1 | 5/2005 | Kung | |
| 6,891,838 B1 | 5/2005 | Petite et al. | |
| 6,898,276 B1 | 5/2005 | Millet et al. | |
| 6,910,074 B1 | 6/2005 | Amin | |
| 6,928,576 B2 | 8/2005 | Sekiguchi | |
| 6,930,598 B2 | 8/2005 | Weiss | |
| 6,931,445 B2 | 8/2005 | Davis | |
| 6,952,773 B2 | 10/2005 | Wheeler | |
| 6,957,275 B1 | 10/2005 | Sekiguchi | |
| 6,961,335 B1 | 11/2005 | Millet et al. | |
| 6,961,857 B1 | 11/2005 | Floryanzia | |
| 6,965,614 B1 | 11/2005 | Osterhout et al. | |

(56) References Cited

U.S. PATENT DOCUMENTS

| | | | |
|---|---|---|---|
| 6,981,025 B1 | 12/2005 | Frazier | |
| 6,988,070 B2 | 1/2006 | Kawasaki | |
| 6,988,075 B1 | 1/2006 | Hacker | |
| 7,007,070 B1 | 2/2006 | Hickman | |
| 7,035,270 B2 | 4/2006 | Moore, Jr. et al. | |
| 7,054,376 B1 | 5/2006 | Rubinstain et al. | |
| 7,058,036 B1 | 6/2006 | Yu et al. | |
| 7,075,919 B1 | 7/2006 | Wendt et al. | |
| 7,123,700 B1 | 10/2006 | Weaver, III et al. | |
| 7,130,719 B2 | 10/2006 | Ehlers et al. | |
| 7,139,811 B2 | 11/2006 | Lev Ran et al. | |
| 7,167,920 B2 | 1/2007 | Traversal et al. | |
| 7,174,512 B2 * | 2/2007 | Martin | H04N 5/4401 715/719 |
| 7,203,477 B2 | 4/2007 | Coppinger et al. | |
| 7,207,048 B2 | 4/2007 | McQuillan et al. | |
| 7,222,087 B1 | 5/2007 | Bezos et al. | |
| 7,235,710 B2 | 6/2007 | Hatzfeld et al. | |
| 7,266,589 B2 | 9/2007 | Brownhill | |
| 7,269,162 B1 | 9/2007 | Turner | |
| 7,277,384 B1 | 10/2007 | Chan | |
| 7,305,550 B2 | 12/2007 | Oliver | |
| 7,313,120 B2 | 12/2007 | Ekberg et al. | |
| 7,336,262 B2 | 2/2008 | Tsuji | |
| 7,349,993 B2 | 3/2008 | Kawamoto et al. | |
| 7,397,807 B2 | 7/2008 | Chen et al. | |
| 7,403,838 B2 | 7/2008 | Deen et al. | |
| 7,421,483 B1 | 9/2008 | Kalra | |
| 7,433,836 B1 | 10/2008 | August | |
| 7,444,401 B1 | 10/2008 | Keyghobad | |
| 7,461,122 B2 | 12/2008 | Kawana | |
| 7,480,724 B2 | 1/2009 | Zimler et al. | |
| 7,526,539 B1 | 4/2009 | Hsu | |
| 7,551,071 B2 | 6/2009 | Bennett et al. | |
| 7,574,660 B2 | 8/2009 | Campbell et al. | |
| 7,584,263 B1 | 9/2009 | Hicks | |
| 7,596,692 B2 | 9/2009 | Fox et al. | |
| 7,627,679 B1 | 12/2009 | Bowen et al. | |
| 7,650,361 B1 * | 1/2010 | Wong | H04N 21/25875 707/999.107 |
| 7,673,001 B1 | 3/2010 | Battle et al. | |
| 7,685,629 B1 | 3/2010 | White | |
| 7,706,928 B1 | 4/2010 | Howell | |
| 7,707,606 B2 | 4/2010 | Hofrichter et al. | |
| 7,761,527 B2 | 7/2010 | Ferreira et al. | |
| 7,765,294 B2 | 7/2010 | Edwards et al. | |
| 7,780,080 B2 | 8/2010 | Owen | |
| 7,809,605 B2 | 10/2010 | Tonse et al. | |
| 7,818,444 B2 | 10/2010 | Brueck | |
| 7,831,748 B2 | 11/2010 | Dernis et al. | |
| 7,836,044 B2 | 11/2010 | Kamvar et al. | |
| 7,865,735 B2 | 1/2011 | Yiachos | |
| 7,895,633 B2 | 2/2011 | Van Hoff et al. | |
| 7,913,278 B2 | 3/2011 | Ellis et al. | |
| 7,933,970 B2 | 4/2011 | Zimler et al. | |
| 7,948,992 B1 | 5/2011 | Holmgren et al. | |
| 7,961,712 B2 | 6/2011 | Rabenko et al. | |
| 7,970,863 B1 | 6/2011 | Fontaine | |
| 7,970,914 B2 | 6/2011 | Bowen et al. | |
| 7,987,490 B2 | 7/2011 | Ansari et al. | |
| 8,005,915 B2 | 8/2011 | Jeon | |
| 8,020,174 B2 | 9/2011 | Sedogbo | |
| 8,027,335 B2 | 9/2011 | Ansari et al. | |
| 8,031,726 B2 | 10/2011 | Ansari et al. | |
| 8,032,409 B1 | 10/2011 | Mikurak | |
| 8,060,589 B1 | 11/2011 | Kao | |
| 8,086,495 B2 | 12/2011 | Ansari et al. | |
| 8,090,856 B1 | 1/2012 | Bonefas | |
| 8,107,217 B2 | 1/2012 | Watanabe | |
| 8,189,608 B2 | 5/2012 | Duo et al. | |
| 8,205,240 B2 | 6/2012 | Ansari et al. | |
| 8,280,978 B2 | 10/2012 | Ansari et al. | |
| 8,281,010 B2 | 10/2012 | Ansari et al. | |
| 8,315,266 B1 | 11/2012 | Lam et al. | |
| 8,369,326 B2 | 2/2013 | Ansari et al. | |
| 8,374,586 B2 | 2/2013 | Bentkovski | |
| 8,375,657 B2 | 2/2013 | Buchwald et al. | |
| 8,386,465 B2 | 2/2013 | Ansari et al. | |
| 8,391,299 B2 | 3/2013 | Schliserman et al. | |
| 8,397,264 B2 | 3/2013 | Ansari et al. | |
| 8,422,397 B2 | 4/2013 | Ansari et al. | |
| 8,459,119 B2 | 6/2013 | Miyamoto et al. | |
| 8,461,413 B2 | 6/2013 | Frankard | |
| 8,508,340 B2 | 8/2013 | Sanchez | |
| 8,510,133 B2 | 8/2013 | Peak | |
| 8,516,118 B2 * | 8/2013 | Saint Clair | H04N 21/43615 709/225 |
| 8,543,665 B2 | 9/2013 | Ansari et al. | |
| 8,577,739 B2 | 11/2013 | Ansari et al. | |
| 8,583,055 B2 | 11/2013 | Park | |
| 8,600,776 B2 | 12/2013 | Raduchel | |
| 8,621,588 B2 | 12/2013 | Yoshida | |
| 8,649,386 B2 | 2/2014 | Ansari et al. | |
| 8,654,936 B1 | 2/2014 | Eslambolchi | |
| 8,665,885 B2 | 3/2014 | Pastorino et al. | |
| 8,694,523 B2 | 4/2014 | Lim et al. | |
| 8,701,166 B2 | 4/2014 | Courtney | |
| 8,738,921 B2 | 5/2014 | Gephart | |
| 8,856,289 B2 | 10/2014 | Ansari et al. | |
| 8,893,293 B1 | 11/2014 | Schmoyer | |
| 8,910,299 B2 | 12/2014 | Michalske | |
| 8,971,341 B2 | 3/2015 | Ansari et al. | |
| 8,973,056 B2 | 3/2015 | Ellis et al. | |
| 9,028,405 B2 | 5/2015 | Tran | |
| 9,071,606 B2 | 6/2015 | Braun et al. | |
| 9,083,798 B2 | 7/2015 | Cross et al. | |
| 9,167,176 B2 | 10/2015 | Winter | |
| 9,202,084 B2 | 12/2015 | Moore | |
| 9,203,912 B2 | 12/2015 | Krishnaswarmy et al. | |
| 9,253,150 B2 | 2/2016 | Ansari et al. | |
| 9,270,492 B2 | 2/2016 | Ansari et al. | |
| 9,325,540 B2 | 4/2016 | Zhang | |
| 9,407,624 B1 | 8/2016 | Myers | |
| 9,414,776 B2 | 8/2016 | Sillay | |
| 9,426,151 B2 | 8/2016 | Richards et al. | |
| 9,569,587 B2 | 2/2017 | Ansari et al. | |
| 9,602,880 B2 | 3/2017 | Ansari et al. | |
| 9,736,028 B2 | 8/2017 | Ansari et al. | |
| 9,924,235 B2 | 3/2018 | Ansari et al. | |
| 10,057,269 B1 | 8/2018 | Ellingson | |
| 10,069,643 B2 | 9/2018 | Ansari et al. | |
| 10,071,395 B2 | 9/2018 | Ansari et al. | |
| 10,097,367 B2 | 10/2018 | Ansari et al. | |
| 10,263,803 B2 | 4/2019 | Ansari et al. | |
| 10,530,598 B2 | 1/2020 | Ansari et al. | |
| 10,764,254 B2 | 9/2020 | Ford | |
| 2001/0011284 A1 | 8/2001 | Humpleman | |
| 2001/0025349 A1 | 9/2001 | Sharood | |
| 2001/0041982 A1 | 11/2001 | Kawasaki | |
| 2001/0048030 A1 | 12/2001 | Sharood | |
| 2001/0049786 A1 | 12/2001 | Harrison et al. | |
| 2001/0051996 A1 | 12/2001 | Cooper et al. | |
| 2002/0021465 A1 | 2/2002 | Moore | |
| 2002/0023131 A1 | 2/2002 | Wu et al. | |
| 2002/0027504 A1 | 3/2002 | David | |
| 2002/0033416 A1 | 3/2002 | Gerszberg | |
| 2002/0035404 A1 | 3/2002 | Ficco | |
| 2002/0046279 A1 | 4/2002 | Chung | |
| 2002/0052915 A1 | 5/2002 | Amin-Salehi | |
| 2002/0059425 A1 | 5/2002 | Belfiore | |
| 2002/0059586 A1 | 5/2002 | Carney et al. | |
| 2002/0060994 A1 | 5/2002 | Kovacs et al. | |
| 2002/0065894 A1 | 5/2002 | Dalal et al. | |
| 2002/0067376 A1 * | 6/2002 | Martin | H04N 21/426 715/810 |
| 2002/0069243 A1 | 6/2002 | Raverdy | |
| 2002/0071440 A1 | 6/2002 | Cerami et al. | |
| 2002/0078150 A1 | 6/2002 | Thompson | |
| 2002/0103877 A1 | 8/2002 | Gagnon | |
| 2002/0112047 A1 | 8/2002 | Kushwaha et al. | |
| 2002/0120686 A1 | 8/2002 | Schell | |
| 2002/0122410 A1 | 9/2002 | Kulikov et al. | |
| 2002/0124257 A1 | 9/2002 | Ismagilov | |
| 2002/0128930 A1 | 9/2002 | Nakamoto et al. | |

(56) References Cited

U.S. PATENT DOCUMENTS

| | | |
|---|---|---|
| 2002/0133613 A1 | 9/2002 | Teng |
| 2002/0136226 A1 | 9/2002 | Christoffel et al. |
| 2002/0156688 A1 | 10/2002 | Horn |
| 2002/0169858 A1 | 11/2002 | Bellinger |
| 2002/0176404 A1 | 11/2002 | Girard |
| 2002/0184358 A1 | 12/2002 | Traversal et al. |
| 2002/0184620 A1 | 12/2002 | Davies et al. |
| 2003/0005112 A1 | 1/2003 | Kraitkremer |
| 2003/0012155 A1 | 1/2003 | Sayeedi |
| 2003/0023131 A1 | 1/2003 | Wu et al. |
| 2003/0023730 A1 | 1/2003 | Wengrovitz |
| 2003/0083961 A1 | 5/2003 | Bezos et al. |
| 2003/0095569 A1 | 5/2003 | Wengrovitz |
| 2003/0112755 A1 | 6/2003 | McDysan |
| 2003/0118726 A1 | 6/2003 | Nakayama |
| 2003/0104010 A1 | 7/2003 | Szeto et al. |
| 2003/0126207 A1 | 7/2003 | Creamer et al. |
| 2003/0135823 A1 | 7/2003 | Marejka |
| 2003/0140103 A1 | 7/2003 | Szeto et al. |
| 2003/0151621 A1 | 8/2003 | McEvilly |
| 2003/0169752 A1 | 9/2003 | Chen et al. |
| 2003/0171996 A1 | 9/2003 | Chen et al. |
| 2003/0185360 A1 | 10/2003 | Moore |
| 2003/0210770 A1 | 11/2003 | Krejcarek |
| 2003/0217110 A1 | 11/2003 | Weiss |
| 2003/0229900 A1 | 12/2003 | Reisman |
| 2003/0231641 A1 | 12/2003 | Ryoo |
| 2003/0237004 A1 | 12/2003 | Okamura |
| 2004/0001480 A1 | 1/2004 | Tanigawa et al. |
| 2004/0003070 A1 | 1/2004 | Fernald et al. |
| 2004/0005859 A1 | 1/2004 | Ghercioiu et al. |
| 2004/0006477 A1 | 1/2004 | Craner |
| 2004/0006769 A1 | 1/2004 | Ansari et al. |
| 2004/0010327 A1 | 1/2004 | Terashima |
| 2004/0019489 A1 | 1/2004 | Funk et al. |
| 2004/0030750 A1 | 2/2004 | Moore et al. |
| 2004/0031058 A1 | 2/2004 | Reisman |
| 2004/0032399 A1 | 2/2004 | Sekiguchi et al. |
| 2004/0047310 A1 | 3/2004 | Chen et al. |
| 2004/0047358 A1 | 3/2004 | Chen et al. |
| 2004/0052076 A1 | 3/2004 | Mueller |
| 2004/0060079 A1 | 3/2004 | Tanaka et al. |
| 2004/0062230 A1 | 4/2004 | Taylor et al. |
| 2004/0073867 A1 | 4/2004 | Kausik et al. |
| 2004/0078573 A1 | 4/2004 | Matsuyama |
| 2004/0114608 A1 | 6/2004 | Rao et al. |
| 2004/0114610 A1 | 6/2004 | Featherson |
| 2004/0128310 A1 | 7/2004 | Zmudzinski et al. |
| 2004/0133657 A1 | 7/2004 | Smith et al. |
| 2004/0136373 A1 | 7/2004 | Bareis |
| 2004/0140989 A1 | 7/2004 | Papageorge |
| 2004/0160969 A1 | 8/2004 | Moon et al. |
| 2004/0174858 A1 | 9/2004 | Caspi et al. |
| 2004/0174863 A1 | 9/2004 | Caspi et al. |
| 2004/0177376 A1 | 9/2004 | Caspi et al. |
| 2004/0203942 A1 | 10/2004 | Dehlin |
| 2004/0213273 A1 | 10/2004 | Ma |
| 2004/0215750 A1 | 10/2004 | Stilp |
| 2004/0218609 A1 | 11/2004 | Foster et al. |
| 2004/0228324 A1 | 11/2004 | Alexiou |
| 2004/0230695 A1 | 11/2004 | Anschutz et al. |
| 2004/0240389 A1 | 12/2004 | Bessis |
| 2004/0255048 A1 | 12/2004 | Lev Ran et al. |
| 2004/0255326 A1 | 12/2004 | Hicks, III et al. |
| 2004/0260427 A1 | 12/2004 | Wimsatt |
| 2005/0018612 A1 | 1/2005 | Fitzgerald |
| 2005/0025887 A1 | 2/2005 | Xin |
| 2005/0027887 A1* | 2/2005 | Zimler .......... H04L 12/2814 |
| | | 709/249 |
| 2005/0038526 A1 | 2/2005 | Choi |
| 2005/0038875 A1 | 2/2005 | Park |
| 2005/0065855 A1 | 3/2005 | Geller |
| 2005/0066063 A1 | 3/2005 | Grigorovitch |
| 2005/0068938 A1 | 3/2005 | Wang |
| 2005/0071663 A1 | 3/2005 | Medvinsky |
| 2005/0076198 A1 | 4/2005 | Skomra et al. |
| 2005/0086479 A1* | 4/2005 | Ondet .......... H04L 63/0869 |
| | | 713/172 |
| 2005/0089052 A1 | 4/2005 | Chen et al. |
| 2005/0094621 A1 | 5/2005 | Acharya |
| 2005/0096753 A1 | 5/2005 | Arling |
| 2005/0107086 A1 | 5/2005 | Tell |
| 2005/0108091 A1 | 5/2005 | Sotak et al. |
| 2005/0141492 A1 | 6/2005 | Chan |
| 2005/0144616 A1 | 6/2005 | Hammond |
| 2005/0149922 A1 | 7/2005 | Vincent |
| 2005/0150697 A1 | 7/2005 | Altman et al. |
| 2005/0174950 A1 | 8/2005 | Ayyagari |
| 2005/0180396 A1 | 8/2005 | Lim |
| 2005/0190744 A1 | 9/2005 | Sun et al. |
| 2005/0190898 A1 | 9/2005 | Priest |
| 2005/0195752 A1 | 9/2005 | Amin-Salehi |
| 2005/0195802 A1 | 9/2005 | Klein |
| 2005/0198040 A1 | 9/2005 | Cohen |
| 2005/0208948 A1 | 9/2005 | Hori |
| 2005/0210064 A1 | 9/2005 | Caldini |
| 2005/0216302 A1 | 9/2005 | Raji |
| 2005/0216580 A1 | 9/2005 | Raji |
| 2005/0216949 A1 | 9/2005 | Candelora et al. |
| 2005/0220081 A1 | 10/2005 | Urquizo |
| 2005/0222933 A1 | 10/2005 | Wesby |
| 2005/0226158 A1 | 10/2005 | Takahashi |
| 2005/0232284 A1 | 10/2005 | Karaoguz et al. |
| 2005/0240680 A1 | 10/2005 | Costa-Requena et al. |
| 2005/0240943 A1 | 10/2005 | Smith et al. |
| 2005/0257039 A1 | 11/2005 | Marshall |
| 2005/0260996 A1 | 11/2005 | Groenendaal |
| 2005/0262257 A1 | 11/2005 | Major |
| 2005/0273790 A1 | 12/2005 | Kearney, III et al. |
| 2005/0286466 A1 | 12/2005 | Tagg |
| 2006/0020589 A1 | 1/2006 | Wu |
| 2006/0025132 A1 | 2/2006 | Karoguz et al. |
| 2006/0029007 A1 | 2/2006 | Ayyagari |
| 2006/0029064 A1 | 2/2006 | Rao et al. |
| 2006/0031406 A1 | 2/2006 | Watson et al. |
| 2006/0031476 A1 | 2/2006 | Mathes et al. |
| 2006/0040667 A9 | 2/2006 | Coppinger et al. |
| 2006/0041926 A1 | 2/2006 | Istvan |
| 2006/0041936 A1 | 2/2006 | Anderson |
| 2006/0067344 A1 | 3/2006 | Sakurai |
| 2006/0075108 A1 | 4/2006 | Sylvain |
| 2006/0075276 A1 | 4/2006 | Kata |
| 2006/0075429 A1 | 4/2006 | Istvan |
| 2006/0080352 A1 | 4/2006 | Boubez et al. |
| 2006/0104432 A1 | 5/2006 | Evslin |
| 2006/0122976 A1 | 6/2006 | Baluja et al. |
| 2006/0136246 A1 | 6/2006 | Tu |
| 2006/0142968 A1 | 6/2006 | Han |
| 2006/0146784 A1 | 7/2006 | Karpov et al. |
| 2006/0153214 A1 | 7/2006 | Moore et al. |
| 2006/0154642 A1 | 7/2006 | Scannell |
| 2006/0159116 A1 | 7/2006 | Gerszberg |
| 2006/0164205 A1 | 7/2006 | Buckingham |
| 2006/0167985 A1 | 7/2006 | Albanese |
| 2006/0174289 A1 | 8/2006 | Theberge |
| 2006/0178943 A1 | 8/2006 | Rollinson et al. |
| 2006/0206565 A1* | 9/2006 | Ganesan .......... H04N 21/632 |
| | | 709/204 |
| 2006/0209857 A1 | 9/2006 | Hicks, III et al. |
| 2006/0220830 A1 | 10/2006 | Bennett |
| 2006/0227724 A1 | 10/2006 | Thubert et al. |
| 2006/0229746 A1 | 10/2006 | Ollis |
| 2006/0239425 A1 | 10/2006 | Hurst |
| 2006/0253894 A1 | 11/2006 | Bookman |
| 2006/0256759 A1 | 11/2006 | Sayeedi |
| 2006/0258396 A1 | 11/2006 | Matsuoka |
| 2006/0259584 A1 | 11/2006 | Watson et al. |
| 2006/0271695 A1 | 11/2006 | Lavian |
| 2006/0288112 A1 | 12/2006 | Soelberg |
| 2006/0291506 A1 | 12/2006 | Cain |
| 2006/0293965 A1 | 12/2006 | Burton |
| 2007/0005766 A1 | 1/2007 | Singhal et al. |
| 2007/0021867 A1 | 1/2007 | Woo |
| 2007/0036303 A1 | 2/2007 | Lee et al. |

(56) References Cited

U.S. PATENT DOCUMENTS

| | | |
|---|---|---|
| 2007/0038637 A1 | 2/2007 | Taneja |
| 2007/0043476 A1 | 2/2007 | Richards et al. |
| 2007/0043478 A1 | 2/2007 | Ehlers et al. |
| 2007/0049342 A1 | 3/2007 | Mayer et al. |
| 2007/0050351 A1 | 3/2007 | Kasperski et al. |
| 2007/0055759 A1 | 3/2007 | McCoy |
| 2007/0058608 A1 | 3/2007 | Lin |
| 2007/0058644 A1 | 3/2007 | Brahmbhatt et al. |
| 2007/0061149 A1 | 3/2007 | Chang |
| 2007/0066490 A1* | 3/2007 | Gemelos ............... A63F 13/792 505/100 |
| 2007/0100981 A1 | 5/2007 | Adamczyk et al. |
| 2007/0106570 A1 | 5/2007 | Hartman et al. |
| 2007/0109976 A1 | 5/2007 | Samanta et al. |
| 2007/0115922 A1 | 5/2007 | Schneider et al. |
| 2007/0133763 A1 | 6/2007 | D'angelo |
| 2007/0143262 A1 | 6/2007 | Kasperski |
| 2007/0143831 A1 | 6/2007 | Pearson |
| 2007/0147420 A1 | 6/2007 | Dean |
| 2007/0150286 A1 | 6/2007 | Miller |
| 2007/0150345 A1 | 6/2007 | Tonse et al. |
| 2007/0216764 A1 | 6/2007 | Kwak |
| 2007/0156265 A1 | 7/2007 | McCoy |
| 2007/0157285 A1 | 7/2007 | Frank |
| 2007/0165629 A1 | 7/2007 | Chaturvedi et al. |
| 2007/0169144 A1 | 7/2007 | Chen |
| 2007/0171091 A1 | 7/2007 | Nisenboim |
| 2007/0171895 A1 | 7/2007 | Oberle et al. |
| 2007/0192477 A1 | 8/2007 | Hicks et al. |
| 2007/0192486 A1 | 8/2007 | Wilson |
| 2007/0192735 A1* | 8/2007 | Lehto ............... H04M 1/72522 715/810 |
| 2007/0198437 A1 | 8/2007 | Eisner et al. |
| 2007/0199022 A1 | 8/2007 | Moshiri |
| 2007/0220165 A1 | 9/2007 | Moorer |
| 2007/0241879 A1 | 10/2007 | Jobe |
| 2007/0250592 A1 | 10/2007 | Reckamp |
| 2007/0253443 A1 | 11/2007 | Dean, Jr. et al. |
| 2007/0273539 A1 | 11/2007 | Gananathan |
| 2007/0286159 A1 | 12/2007 | Preiss et al. |
| 2007/0291650 A1 | 12/2007 | Ormazabal |
| 2007/0294721 A1 | 12/2007 | Haeuser |
| 2007/0297454 A1 | 12/2007 | Brothers |
| 2008/0005306 A1 | 1/2008 | Kushalnagar |
| 2008/0005565 A1 | 1/2008 | Shiga |
| 2008/0022391 A1 | 1/2008 | Sax |
| 2008/0043719 A1 | 2/2008 | Pok et al. |
| 2008/0052393 A1 | 2/2008 | McNaughton et al. |
| 2008/0062965 A1 | 3/2008 | Silva |
| 2008/0066126 A1 | 3/2008 | Walter |
| 2008/0069121 A1 | 3/2008 | Adamson et al. |
| 2008/0084789 A1 | 4/2008 | Altman et al. |
| 2008/0084888 A1 | 4/2008 | Yadav et al. |
| 2008/0098212 A1 | 4/2008 | Helms |
| 2008/0101320 A1 | 5/2008 | Krahn et al. |
| 2008/0115162 A1 | 5/2008 | Yu et al. |
| 2008/0123683 A1 | 5/2008 | Cheng et al. |
| 2008/0127063 A1 | 5/2008 | Silva |
| 2008/0130666 A1 | 6/2008 | Kawamoto et al. |
| 2008/0134258 A1 | 6/2008 | Goose |
| 2008/0141315 A1 | 6/2008 | Ogilvie |
| 2008/0144642 A1 | 6/2008 | Song |
| 2008/0147205 A1 | 6/2008 | Ollis |
| 2008/0151778 A1 | 6/2008 | Venkitaraman et al. |
| 2008/0155613 A1 | 6/2008 | Benya |
| 2008/0163059 A1 | 7/2008 | Craner |
| 2008/0166048 A1 | 7/2008 | Raif et al. |
| 2008/0177856 A1 | 7/2008 | Howard |
| 2008/0178236 A1 | 7/2008 | Hoshall |
| 2008/0221715 A1 | 9/2008 | Krzyzanowski |
| 2008/0239957 A1 | 10/2008 | Tokura |
| 2008/0240125 A1 | 10/2008 | Purvis et al. |
| 2008/0272934 A1 | 11/2008 | Wang |
| 2008/0304500 A1 | 12/2008 | Schliserman et al. |
| 2009/0034419 A1 | 2/2009 | Flammer et al. |
| 2009/0077207 A1 | 3/2009 | Karaoguz et al. |
| 2009/0100460 A1 | 4/2009 | Hicks |
| 2009/0178079 A1* | 7/2009 | Derrenberger ..... H04N 5/44543 725/42 |
| 2009/0180422 A1 | 7/2009 | Bohacek et al. |
| 2009/0189774 A1 | 7/2009 | Brundridge et al. |
| 2009/0216847 A1 | 8/2009 | Krishnaswarmy et al. |
| 2010/0014444 A1 | 1/2010 | Ghanadan et al. |
| 2010/0030734 A1 | 2/2010 | Chunilal |
| 2010/0061309 A1 | 3/2010 | Buddhikot et al. |
| 2010/0071053 A1 | 3/2010 | Ansari et al. |
| 2010/0142692 A1 | 6/2010 | Gotta |
| 2010/0153730 A1* | 6/2010 | Goria ................... H04N 7/1675 713/173 |
| 2010/0205152 A1 | 8/2010 | Ansari et al. |
| 2010/0211636 A1* | 8/2010 | Starkenburg ........ H04N 7/17318 709/203 |
| 2010/0231790 A1* | 9/2010 | Ansari .................... G06F 16/64 348/552 |
| 2010/0238810 A1 | 9/2010 | Ormazabal |
| 2010/0241711 A1 | 9/2010 | Ansari et al. |
| 2010/0291940 A1 | 11/2010 | Koo |
| 2011/0019135 A1 | 1/2011 | Koganezawa |
| 2011/0092232 A1 | 4/2011 | Lee |
| 2011/0182205 A1 | 7/2011 | Gerdes et al. |
| 2012/0060181 A1* | 3/2012 | Craner ............... H04N 21/4532 725/28 |
| 2012/0101881 A1 | 4/2012 | Taylor et al. |
| 2012/0110490 A1 | 5/2012 | Keller |
| 2012/0157043 A1 | 6/2012 | LaJoie |
| 2012/0311665 A1 | 12/2012 | Lim |
| 2013/0191871 A1 | 7/2013 | Gilboy |
| 2013/0329745 A1 | 12/2013 | Phillips et al. |
| 2014/0362253 A1 | 12/2014 | Kim |
| 2015/0074259 A1 | 3/2015 | Ansari et al. |
| 2015/0208363 A1 | 7/2015 | Funk et al. |
| 2016/0226823 A1 | 8/2016 | Ansari et al. |
| 2016/0226920 A1 | 8/2016 | Ansari et al. |
| 2016/0330200 A1 | 11/2016 | Ansari et al. |
| 2016/0344745 A1 | 11/2016 | Johnson et al. |
| 2017/0070395 A1 | 3/2017 | Ansari et al. |
| 2017/0078154 A1 | 3/2017 | Ansari et al. |
| 2017/0344703 A1 | 11/2017 | Ansari et al. |
| 2018/0123819 A1 | 5/2018 | Ansari et al. |
| 2018/0123905 A1 | 5/2018 | Ansari et al. |
| 2018/0124115 A1 | 5/2018 | Ansari et al. |
| 2018/0131571 A1 | 5/2018 | Ansari et al. |
| 2018/0131572 A1 | 5/2018 | Ansari et al. |
| 2018/0152310 A1 | 5/2018 | Ansari et al. |
| 2018/0198692 A1 | 7/2018 | Ansari et al. |
| 2018/0227140 A1 | 8/2018 | Ansari et al. |
| 2019/0245714 A1 | 8/2019 | Ansari et al. |
| 2019/0312745 A1 | 10/2019 | Ansari et al. |
| 2020/0076638 A1 | 3/2020 | Ansari et al. |
| 2020/0228364 A1 | 7/2020 | Ansari et al. |
| 2020/0274727 A1 | 8/2020 | Ansari et al. |
| 2020/0279626 A1 | 9/2020 | Ansari et al. |
| 2020/0294636 A1 | 9/2020 | Ansari et al. |
| 2021/0194715 A1 | 6/2021 | Ansari et al. |
| 2021/0211320 A1 | 7/2021 | Ansari et al. |
| 2021/0218571 A1 | 7/2021 | Ansari et al. |

FOREIGN PATENT DOCUMENTS

| | | |
|---|---|---|
| DE | 3818631 | 12/1989 |
| DE | 9116206 | 4/1992 |
| DE | 19723596 | 10/1998 |
| DE | 10024525 | 11/2001 |
| DE | 20304806 | 8/2003 |
| EP | 0805254 | 11/1997 |
| EP | 0921260 | 6/1999 |
| EP | 1113659 | 7/2001 |
| EP | 1195497 | 4/2002 |
| EP | 1377005 | 1/2004 |
| EP | 1394986 | 3/2004 |
| EP | 1657396 | 5/2006 |
| JP | 07104063 | 4/1995 |
| JP | 03269387 | 3/2002 |

(56) References Cited

FOREIGN PATENT DOCUMENTS

| | | |
|---|---|---|
| JP | 2002139565 | 5/2002 |
| WO | WO0193533 | 12/2001 |
| WO | WO2005111653 | 11/2005 |
| WO | WO2007004921 | 1/2007 |
| WO | WO2008021665 | 2/2008 |
| WO | WO2008082346 | 7/2008 |
| WO | WO2008082441 | 7/2008 |
| WO | WO2008083384 | 7/2008 |
| WO | WO2008083385 | 7/2008 |
| WO | WO2008083387 | 7/2008 |
| WO | WO2008083391 | 7/2008 |
| WO | WO2008085201 | 7/2008 |
| WO | WO2008085202 | 7/2008 |
| WO | WO2008085203 A2 | 7/2008 |
| WO | WO2008085204 A2 | 7/2008 |
| WO | WO2008085205 A2 | 7/2008 |
| WO | WO2008085206 A2 | 7/2008 |
| WO | WO2008085207 A2 | 7/2008 |
| WO | WO2008085205 A3 | 9/2008 |
| WO | WO2008085204 A3 | 10/2008 |
| WO | WO2008085207 A3 | 10/2008 |
| WO | WO2008085203 A3 | 11/2008 |
| WO | WO2008085206 A3 | 11/2008 |
| WO | WO2009036088 | 3/2009 |
| WO | WO2009036185 | 3/2009 |
| WO | WO2009086134 | 7/2009 |

OTHER PUBLICATIONS

Dueans, J.C., "An End-to-End Service Provisioning Scenario for the Residential Environment," IEEE Communications Magazine, Sep. 2005, pp. 94-100.
Ganguly, A., et al., "IP over P2P: enabling self-configuring virtual IP networks for grid computing," in Parallel and Distributed Processing symposium, 20060 IPDPS Apr. 25-29, 2006, retrieved on Jan. 20, 2010, retrieved from the internet http://aarxiv.org/PS_cache/cs/pdf/0603/0603087v1.pdf.
Haerick W et al., "Success in Home Service Deployment: Zero-Touch or Chaos?", British Telecommunications, Jul. 1, 2007, pp. 36-43, vol. 5, No. 3, London, GB.
Il-Woo Lee, et al., "A Proposed Platform & Performance Estimation of Digital-Home Service Delivery/Management Systems," Apr. 10, 2006, pp. 713-719, Information Technology: New Generations, 2006.
Intel, "Delivering on the Promise of Triple Play Digital Media," Technology Backgrounder, Consumer Electronics, 2004, pp. 1-4.
International Application No. PCT/US2008/087724, filed Dec. 19, 2008, 7 Pages, 1211 Geneva 20, Switzerland.
International Search Report and the Written Opinion of the International Searching Authority issued in International Application No. PCT/US2008/087724 dated Feb. 17, 2009.
International Search Report and the Written Opinion of the International Searching Authority issued in International Patent Application No. PCT/US08/75889 dated on Nov. 24, 2008.
International Search Report and Written Opinion in International Application No. PCT/US05/15860, dated Jul. 17, 2006, 8 pages.
International Search Report and Written Opinion in International Application No. PCT/US08/76036, dated Nov. 14, 2008.
International Search Report in International Application No. PCT/JP2008/051225, dated Feb. 19, 2008.
International Search Report dated Apr. 25, 2008, International Application No. PCT/US2007/019531, filed Sep. 7, 2007, 1 page.
International Search Report dated Aug. 21, 2008, International Application No. PCT/US2007/019534, filed Sep. 7, 2007, 1 page.
International Search Report dated Aug. 25, 2008, International Application No. PCT/US2007/019545, filed Sep. 7, 2007, 1 page.
International Search Report dated Aug. 27, 2008, International Application No. PCT/US2007/089237, filed Dec. 31, 2007, 6 pages.
International Search Report dated Jul. 14, 2008, International Application No. PCT/US2007/019546, filed Sep. 7, 2007, 1 page.
International Search Report dated Jul. 17, 2008, International Application No. PCT/US2007/019543, filed Sep. 7, 2001, 1 page.
International Search Report dated Jul. 2, 2008, International Application No. PCT/US2007/019544, filed Sep. 7, 2007, 1 page.
International Search Report dated Mar. 14, 2008, International Application No. PCT/US2007/019533, filed Sep. 7, 2007, 1 page.
Machine Translation of JP11290082-A, Oct. 1999.
Notification of Transmittal of the International Search Report and the Written Opinion of the International Searching Authority, or the Declaration dated Aug. 27, 2008, 24 pages, Application No. PCT/US2007/089232.
Notification of Transmittal of the International Search Report and the Written Opinion of the International Searching Authority, or the Declaration dated Aug. 8, 2008, 22 pages, Application No. PCT/US2007/089227.
Notification of Transmittal of the International Search Report and the Written Opinion of the International Searching Authority, or the Declaration dated Oct. 22, 2008, 12 pages, Application No. PCT/US2007/089232.
Notification of Transmittal of the International Search Report and the Written Opinion of the International Searching Authority, or the Declaration, dated Feb. 26, 2008, 11 pages, Application No. PCT/US07/19483.
Notification of Transmittal of the International Search Report and the Written Opinion of the International Searching Authority, or the Declaration, dated Mar. 14, 2008, 12 pages, Application No. PCT/US07/19533.
PCT Invitation to Pay Additional Fees and, where Applicable, Protest Fee (PCT/ISA/206) and Communication Relating to the Results of the Partial International Search (Annex to PCT/ISA/206) dated May 19, 2008 for PCT Application No. PCT/US2007/089237, 7 pages.
PCT Invitation to Pay Additional Fees and, where Applicable, Protest Fee (PCT/ISA/206) and Communication Relating to the Results of the Partial International Search (Annex to PCT/ISA/206) dated May 21, 2008 for PCT Application No. PCT/US2007/089227, 7 pages.
Technology and challenges of virtual communities. International Journal of Business Research, v 7, n 4, p. 69 Jul. 2007.
Wen-Shyang Hwang et al., "A QoS-aware Residential Gateway with Bandwidth Management," Aug. 2005.
Written Opinion of the International Searching Authority dated Apr. 25, 2008, International Application No. PCT/US2007/019531, filed Sep. 7, 2007, 7 pages.
Written Opinion of the International Searching Authority dated Aug. 21, 2008, International Application No. PCT/US2007/019534, filed Sep. 7, 2007, 5 pages.
Written Opinion of the International Searching Authority dated Aug. 25, 2008, International Application No. PCT/US2007/019545, filed Sep. 7, 2007, 5 pages.
Written Opinion of the International Searching Authority dated Jul. 14, 2008, International Application No. PCT/US2007/019546, filed Sep. 7, 2007, 5 pages.
Written Opinion of the International Searching Authority dated Jul. 17, 2008, International Application No. PCT/US2007/019543, filed Sep. 7, 2007, 5 pages.
Written Opinion of the International Searching Authority dated Jul. 2, 2008, International Application No. PCT/US2007/019544, filed Sep. 7, 2007, 5 pages.
Written Opinion of the International Searching Authority dated Mar. 14, 2008, International Application No. PCT/US2007/19533, filed Sep. 7, 2007, 7 pages.
Written Opinion of the International Searching Authority dated Aug. 27, 2008, International Application No. PCT/US2007/089237, filed Dec. 31, 2007, 15 pages.
Yeon-Joo, O. et al., "Design of a SIP-based Real-time Visitor Conversation and Door Control Architecture using a Home Gateway," Consumer Electronics, 2006, ICCE '06, 2006 Digest of Technical Papers, International Conference, Las Vegas, NV, USA, IEEE, Jan. 1, 2006, pp. 187-188.
Young-Gab Kim et al., A Service Bundle Authentication Mechanism in the OSGI Service Platform, Advanced Information Networking and Applications, 2004, AINA 2004. 18th International Conference

(56) References Cited

OTHER PUBLICATIONS on Fukuoka, Japan, Mar. 29-31, 2004, Piscataway, NJ, USA, IEEE, vol. 1, Mar. 29, 2004, pp. 420-425.
U.S. Appl. No. 16/002,945 for Ansari et al., filed Jun. 7, 2018.
U.S. Appl. No. 16/044,790 for Ansari et al., filed Jul. 25, 2018.
U.S. Appl. No. 16/124,500 for Ansari et al., filed Sep. 7, 2018.
U.S. Appl. No. 16/684,915 for Ansari et al., filed Nov. 15, 2019.
U.S. Appl. No. 16/778,304 for Ansari et al., filed Jan. 31, 2020.
U.S. Appl. No. 16/291,856 for Ansari et al., filed Mar. 4, 2019.
U.S. Appl. No. 16/439,501 for Ansari et al., filed Jun. 12, 2019.
U.S. Appl. No. 16/460,148 for Ansari et al., filed Jul. 2, 2019.
U.S. Appl. No. 16/512,876 for Ansari et al., filed Jul. 16, 2019.
U.S. Appl. No. 16/514,803 for Ansari et al., filed Jul. 17, 2019.
U.S. Appl. No. 16/531,914 for Ansari et al., filed Aug. 5, 2019.
U.S. Appl. No. 16/900,487, for Ansari et al., filed Jun. 12, 2020.
"Apple moves to link TV to the computer," TVTechnology, Sep. 18, 2006, 2 pages.
"Apple Releases QuickTime 5 and QuickTime Streaming Server 3 Public Previews," Apple Press Release, Oct. 10, 2000, 3 pages.
"Microsoft Introduces New Interactive Program Guide Solution to Improve Digital Cable TV Experience," Microsoft, May 6, 2002, 4 pages.
"Microsoft WebTV Networks Announces Pricing for UltimateTV Service," PressPass, Microsoft, Oct. 26, 2000, 2 pages.
"QuickTime 4.0 Plays MP3," Wired, Apr. 14, 1999, 3 pages.
"QuickTime 6.4 User's Guide," Apple Computer, Inc.,2003, 50 pages.
"QuickTime 7 User's Guide," Apple Computer, Inc., 2005, 62 pages.
"RealNetworks Releases RealPlayer 10, the best Media Player Ever," E-Channel News, Jan. 7, 2004, 4 pages.
"Vulnerability in Windows Media Services Could Allow a Denial of Service," Microsoft Security Bulletin, MS04-008, Mar. 9, 2004, 12 pages.
"Windows Media Services 4.1," Microsoft, 2000, 3 pages.
Akst, D., "The Cutting Edge: Computing/Technology/Innovation: The Hear and Now of Making Sound on the Internet," Los Angeles Times, Jun. 28, 1995, 8 pages.
Apple TV Setup Guide, 2008, 37 pages.
Lane, S., "Disney chief talks up Apple's iTV media hub," AppleInsider, 13 pages.
Mattson, W., "QuickTime 4 ready for prime time," ZDNet, Jun. 9, 1999, 5 pages.
Perez, C., "Microsoft TV (IPTV) is here," Academy Florida, Jan. 9, 2006, 10 pages.
Sheesley, J., "Add Streaming Media Capability to Your Windows NT Server," TechRepublic, May 13, 2002, 11 pages.
Transcription of Apple Showtime Event 2006—The iTV Introduction (Pt. 1) <https://www.youtube.com/watch?v=X_oz3DdLkG4>, including screenshots of Apple devices, GUI's, and menus from video (2006), 13 pages.
U.S. Appl. No. 17/000,067 for Ansari et al., filed Aug. 21, 2020.
U.S. Appl. No. 17/019,930 for Ansari et al., filed Sep. 14, 2020.
U.S. Appl. No. 17/077,964 for Ansari et al., filed Oct. 22, 2020.
U.S. Appl. No. 17/236,443 for Ansari et al., filed Apr. 21, 2021.
U.S. Appl. No. 17/341,569 for Ansari et al., filed Jun. 8, 2021.
U.S. Appl. No. 17/380,312 for Ansari et al., filed Jul. 20, 2021.
U.S. Appl. No. 17/491,440 for Ansari et al., filed Sep. 30, 2021.
U.S. Appl. No. 17/498,731 for Ansari et al., filed Oct. 11, 2021.
U.S. Appl. No. 17/506,451 for Ansari et al., filed Oct. 20, 2021.
U.S. Appl. No. 17/516,352 for Ansari et al., filed Nov. 1, 2021.

\* cited by examiner

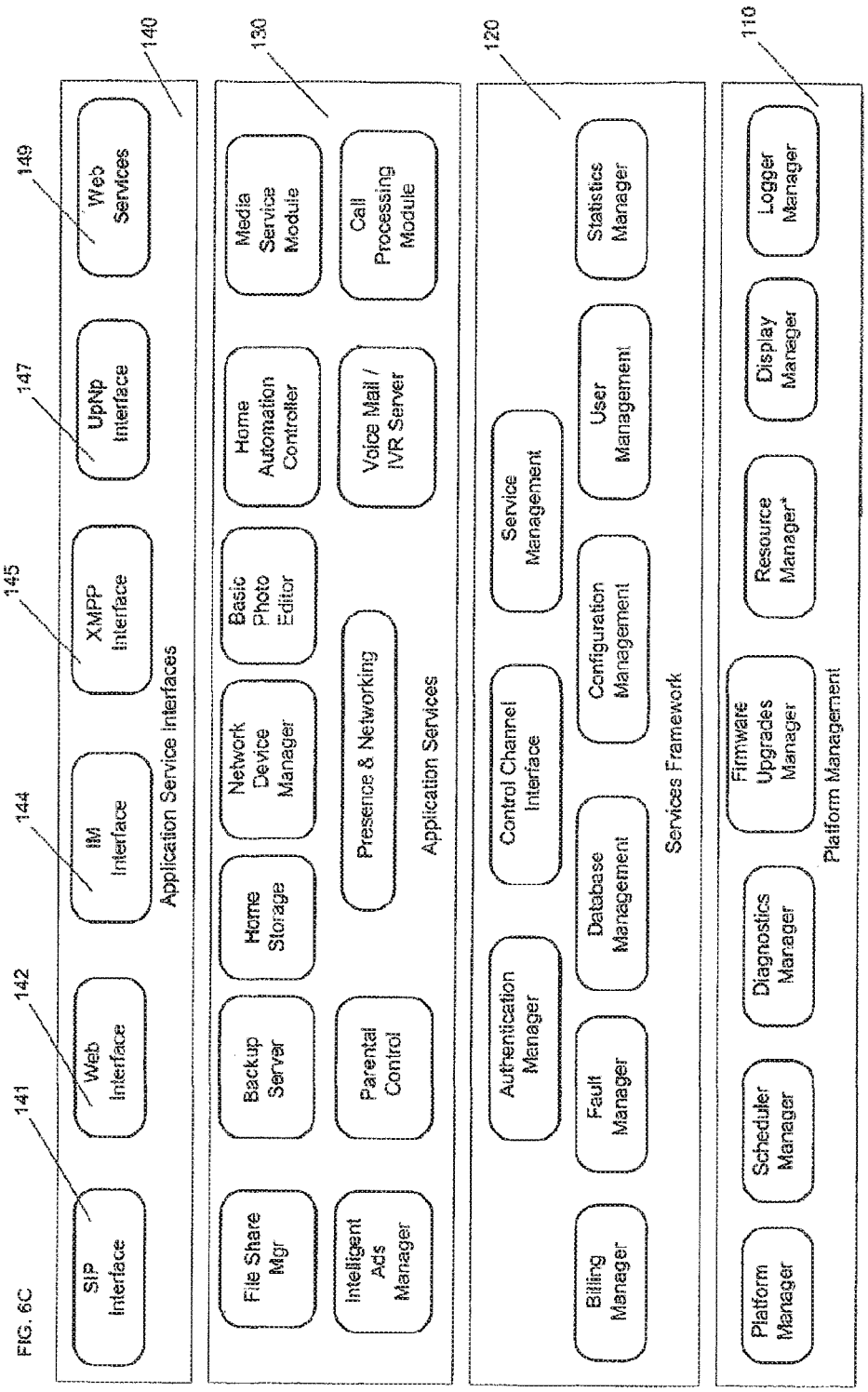

DISPLAY INSERTS, OVERLAYS, AND GRAPHICAL USER INTERFACES FOR MULTIMEDIA SYSTEMS

CROSS-REFERENCE TO RELATED APPLICATIONS

This application is a divisional U.S. patent application Ser. No. 15/360,700, files Nov. 23, 2016, which is continuation of U.S. application Ser. No. 13/793,336, filed Mar. 11, 2013, now U.S. Pat. No. 9,602,880, which is a continuation of U.S. application Ser. No. 12/251,760, filed May 28, 2010, now U.S. Pat. No. 8,397,264, which is a Unite States national stage entry of International Application No. PCT/US2007/019533, filed Sep. 7, 2007, which claims the benefit of U.S. Provisional Application No. 60/882/865, filed Dec. 29, 2006, and of U.S. Provisional Application No. 60/882,862, filed Dec. 29, 2006, the disclosures of which are incorporated herein by reference.

FIELD OF THE INVENTION

The disclosed subject matter relates to gateways and digital media devices, programming for such devices, and media and service distribution systems to provide media signals from a media source and provide application services from an application services device independent of the media source, where the digital media device provides a composite signal to an audio-video system for an audio type presentation, video type television presentation, or audio and video type presentation. The disclosed subject matter also encompasses digital media devices and/or programming thereof for offering a graphical user interface (GUI) presenting a moveable arrangement of icons for selectively accessing application services.

BACKGROUND

The digital home is now becoming more complex with the myriad of new and emerging digital devices and services intended to address many user and consumer needs such as communication, entertainment, privacy and security, etc. However, given the complexity of the emerging digital home and digital environments generally, users who are technologically challenged may find it a daunting and intimidating task to integrate new devices into their home network of interconnected digital devices. Additionally, users may find it difficult to integrate new services along with their existing services such as in-home media sources, broadcast sources, Internet services from an Internet Services Provider (ISP), cable television services, etc. Often accompanying the new devices and/or services are user interfaces for controlling functionality and delivery of applications and services. These new interfaces typically have a different look and feel, thus compounding the daunting task of using the new devices and services.

Moreover, new paradigms are emerging oriented to delivering media content to and the consuming of media content at the home. Many of these paradigms rely on communication of application specific data to and/or from the Internet, as opposed to conventional telephone, broadcast video type applications, or from in-home media sources such as Digital Video Recorders (DVRs), Digital Video Disc (DVD) players, and the like. Furthermore, with respect to Internet based data, most of the content delivery solutions are provided to the digital home networks through availability of the "two-foot" interface (i.e., the PC). It is relatively cumbersome to bring this Internet based data content to the "ten-foot" interface (e.g., the television).

Increasingly, there is a need in a user home or similar digital environment to interconnect and simplify the overall management of application specific data devices with media content and other data to and/or from the Internet along with on-premises media sources, broadcast media sources, game console devices, and other home network devices with a common, dynamic Graphical User Interface (GUI) as may be presented on a television or audio-video system display. A further need exists to have such a GUI be able to dynamically add applications, features, and functionality as a user adds or removes devices from the home network, or as they subscribe to various services. Such techniques or devices should reduce the complexity of the maintenance, upgrading, and operation of even the more basic needs addressed by emerging digital endpoint devices and networks. Current approaches that suggest greater functionality in home-based appliances fail to reduce or address the complexity of managing and provisioning those appliances, especially with a common GUI presented over the "ten foot" interface, which may be dynamically change as devices, functionality, and services are added or removed.

A further unmet need is for a combination of different content from media and/or application sources to be presented concurrently to a user via a "ten-foot" interface. Accordingly, there is a need for a digital media device inside the user premises to combine signals from various media and/or application sources that are separate from one another, and provide the combined signal to a television display or audio-video system for presentation to the user.

In that regard, it would be desirable to provide a digital media device for a user premises, or a media and service distribution system, that provides a composite of media and application services, IP-based communication services, offers a centralized management capability for application services, and provides a dynamic GUI to access the media and application services.

SUMMARY

The technologies disclosed herein address one or more of the needs discussed above and provide improved results over existing technologies. The technology discussed herein may be embodied in a digital media device, typically for deployment at the user premises, and/or to programming for devices that may function as digital media devices. In addition, the technology discussed herein may be embodied in media and service distribution systems. The digital media devices, as well as the media and service distribution systems, may be implemented in such a manner as to offer users a selection from a variety of media from various media sources, as well as many independently provided application services, at the user premises. The applications offered via the user's digital media device may be managed by a gateway type device capable of handling digital media and/or by a service management center. As described herein, one or more of the endpoint devices may be digital media devices communicatively coupled to a television display or to an audio-video system with a television type output.

In one example, a digital media device is communicatively coupled to a television display for operation at user premises. The digital media device can include a first interface configured to receive a media signal from a media source for presentation via the television display. A second interface can be included that is configured to enable bi-directional communications between the digital media device and an application service provider device via a data communications link in the user premises, where the application service provider device, which is independent from the media source, is configured to provide an application service from a wide area network to the second interface of the digital media device via the user premises data communications network. The digital media device includes a processor coupled to the first interface and the second interface, where the processor is configured to form a composite signal from the media signal and application service information from the provider device, where the composite signal comprises a composite image on the television display. The digital media device receives a selection signal based on the displayed image. The selection signal is transmitted via the user premises data communications network to the application service provider device or to the media source.

The data communications link in the user premises may be a user premises data communications network.

The first interface of the digital media device may be configured to receive the media signal from one or more media sources, where the media signal may be from an analog or digital video source. The media signal may also be an audio signal, and the application service information may provide information for an audio signal. A composite signal may be formed from the media signal and the application service information.

The media signal of the composite signal formed by the digital media device may be used to form from a primary image, and the application service information of the composite signal may form a secondary image. Alternatively, the primary image may be formed from the application service information, and the secondary image may be formed from the media signal. A television display is configured to display the secondary image overlaid on or inserted into the primary image to form the composite image.

The detailed description provides an example of a media and service distribution system for a user premises having a media source to supply to a media signal and a user premises data communications network. The media and service distribution system includes a gateway device for operation at the user premises, independent of the media source, configured to receive an application service via a wide area network and further configured to provide and manage services to one or more endpoint devices associated with the gateway device. The media and service distribution system also includes a digital media device communicatively coupled to a television display. The digital media device can include a first interface configured to receive the media signal from the media source for presentation via the television display. A second interface can be included with the digital media device configured to enable bi-directional communications between the digital media device and the gateway device coupled to the user premises data communications network, where the gateway device can be configured to provide the application service from the wide area network to the second interface of the digital media device. The digital media device also includes a processor coupled to the first interface and the second interface. The processor is configured to form a composite signal from the media signal and application service information from the gateway device, where the composite signal comprises a composite image on the television display. The digital media device receives a selection signal based on the displayed image, and where the selection signal is transmitted via the user premises data communications network to the gateway device or to the media source. It can be appreciated that the gateway device and digital media device can essentially operate as one gateway and digital media device in accordance with the teachings herein. A combined system would include at least one interface to support communications with digital media providers and endpoint devices over data networks (e.g., local and wide area networks).

The gateway device may be communicatively coupled to a service management center via the wide area network. In such a case, the gateway may be configured to provide the application service from the wide area network to associated endpoint devices such as the combination of the digital media device and television, responsive to a communication from the service management center.

The application service information from the gateway device may comprise notifications of status with regard to one or more application services managed by the gateway device. The processor of the digital media device may receive the notifications of status from the gateway device and transmit a message related to the selection signal the to the gateway device, via the user premises data communications network, using a presence and networking protocol.

The gateway device may include a first interface for enabling bi-directional network layer communications on the user's side of the premises with one or more of the associated endpoint devices. A second interface of the gateway device may enable bi-directional network layer communications for the one or more endpoint devices via a wide area network, and for enabling at least some bi-directional communications with a service management center external to the premises via the wide area network. A processor may be coupled to the interfaces, and storage coupled to the processor. Programming may be embodied in the storage for a plurality of application services, where, for each application service, execution of the programming by the processor causes the gateway device to provide functions in relation to a respective service for one or more endpoint devices. The programming embodied on the gateway device may further include logic for a plurality of application services, logic for interfaces for the application services, including at least one television interface for implementation on the television display through the digital media device, logic for a services framework, and logic for platform management.

The detailed description provides an example of a digital media device with a specific programming architecture. The digital media device provides graphical interaction with a media and service distribution system via a television display. The graphical interaction via the television display includes arranging a first set of graphical icons in a pattern displayed on the television display, where the pattern has a first end and a second end. The graphical icons may be arranged in a substantially curved pattern or a substantially linear pattern. The first end and the second end are each defined by a display edge of the television display, and each graphical icon of the first set represents a media application, service application, or media and service application. The graphical interaction also includes highlighting one of the graphical icons of the first set, which is located substantially at a center of the pattern, so as to enable selection of the one graphical icon. The digital media device receives a selection to move the arrangement icons in the pattern in a first direction or a second direction, so as to arrange a second set of graphical icons for display on the television display in the pattern. One or more of the graphical icons of the second set is different from one or more of the graphical icons in the first set. Also, the rotation of the arrangement of the first set of icons to the second set of icons enables at least one graphical icon of the first set to be rotated beyond the display edge, so as to no longer be visible on the television display. The graphical interaction also includes highlighting one of the second set of graphical icons located substantially at the center of the pattern to enable selection. The digital media device receives a selection of the highlighted icon for at least one media application, service application, or media and service application. The graphical interaction also includes displaying the selected media application, service application, or media and service application on the television display.

During the graphical interaction, the digital media device may receive a selection of the highlighted icon that enables the execution of the programming embodied on the digital media device to provide the selected service application from a gateway device through the digital media device, via a user premises data communications network. Alternatively, receiving a selection of the highlighted icon may enable the execution of the programming embodied on the digital media device to provide a selected media application from a media source to the digital media device.

The programming architecture of the digital media device may dynamically add or dynamically remove one or more graphical icons from the first plurality of graphical icons or the second plurality of graphical icons. The dynamic adding or removing of the one or more icons may be determined by subscriptions to media applications, service applications, or media and service applications.

The disclosure also encompasses program products for implementing digital media devices of the type outlined above. In such a product, the programming is embodied in or carried on a machine-readable medium.

The detailed description also provides an example of a digital media device communicatively coupled to an audio-video system for providing a television type output to a viewer at a user premises. The digital media device includes a first interface configured to receive a media signal containing audio and video information, from a media source, for television type presentation via the audio-video system. A second interface is configured to enable bi-directional communications between the digital media device and an application service provider device via a user premises data communications network, where the application service provider device is independent from the media source. The second interface is also configured to receive information for an application service offered from a wide area network from the application service provider device via the user premises data communications network. The second interface is also configured to send messages related to the application service via the user premises data communications network to the application service provider device. The digital media device includes a third interface configured to at least provide output to the audio-video system. The digital media device also includes a processor coupled to the first, second, and third interfaces. The processor is configured to form a composite signal containing audio and video information, in response to the media signal and the received information for the application service. The processor supplies the composite signal for output via the third interface to the audio-video system for television type presentation. The processor is also configured to respond to a user selection signal based on the television type presentation of the composite signal to cause the second interface to send a message related to a selection for the application service, via the second interface and the user premises data communications network, to the application service provider device.

The detailed description also provides an example of a media and service distribution system for a user premises having a media source to supply to media signal and a user premises data communications network. The media and service distribution system includes a gateway device for operation at the user premises, independent of the media source, configured to receive an application service via a wide area network and further configured to provide and manage services to one or more endpoint devices associated with the gateway device. The media and service distribution system also includes a digital media device communicatively coupled to an audio-video system for providing a television type output to a viewer at a user premises. The digital media device includes a first interface configured to receive a media signal containing audio and video information, from a media source, for television type presentation via the audio-video system. A second interface is configured to enable bi-directional communications between the digital media device and an application service provider device via a user premises data communications network. The application service provider device is independent from the media source. The second interface is also configured to receive information for an application service offered from a wide area network from the application service provider device via the user premises data communications network. Also, the second interface is configured to send messages related to the application service via the user premises data communications network to the application service provider device. The digital media device includes a third interface configured to at least provide output to the audio-video system the audio-video system. The digital media device also includes a processor coupled to the first, second, and third interfaces. The processor is configured to form a composite signal containing audio and video information, in response to the media signal and the received information for the application service. The processor supplies the composite signal for output via the third interface to the audio-video system for television type presentation. The processor is also configured to respond to a user selection signal based on the television type presentation of the composite signal to cause the second interface to send a message related to a selection for the application service, via the second interface and the user premises data communications network, to the application service provider device.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE FIGURES

The drawing figures depict one or more implementations in accord with the present teachings, by way of example only, not by way of limitation. In the figures, like reference numerals refer to the same or similar elements.

FIGS. 6A-6D depict the software and hardware architectures of the multi-services applications gateway device.

DETAILED DESCRIPTION

Figure 1:
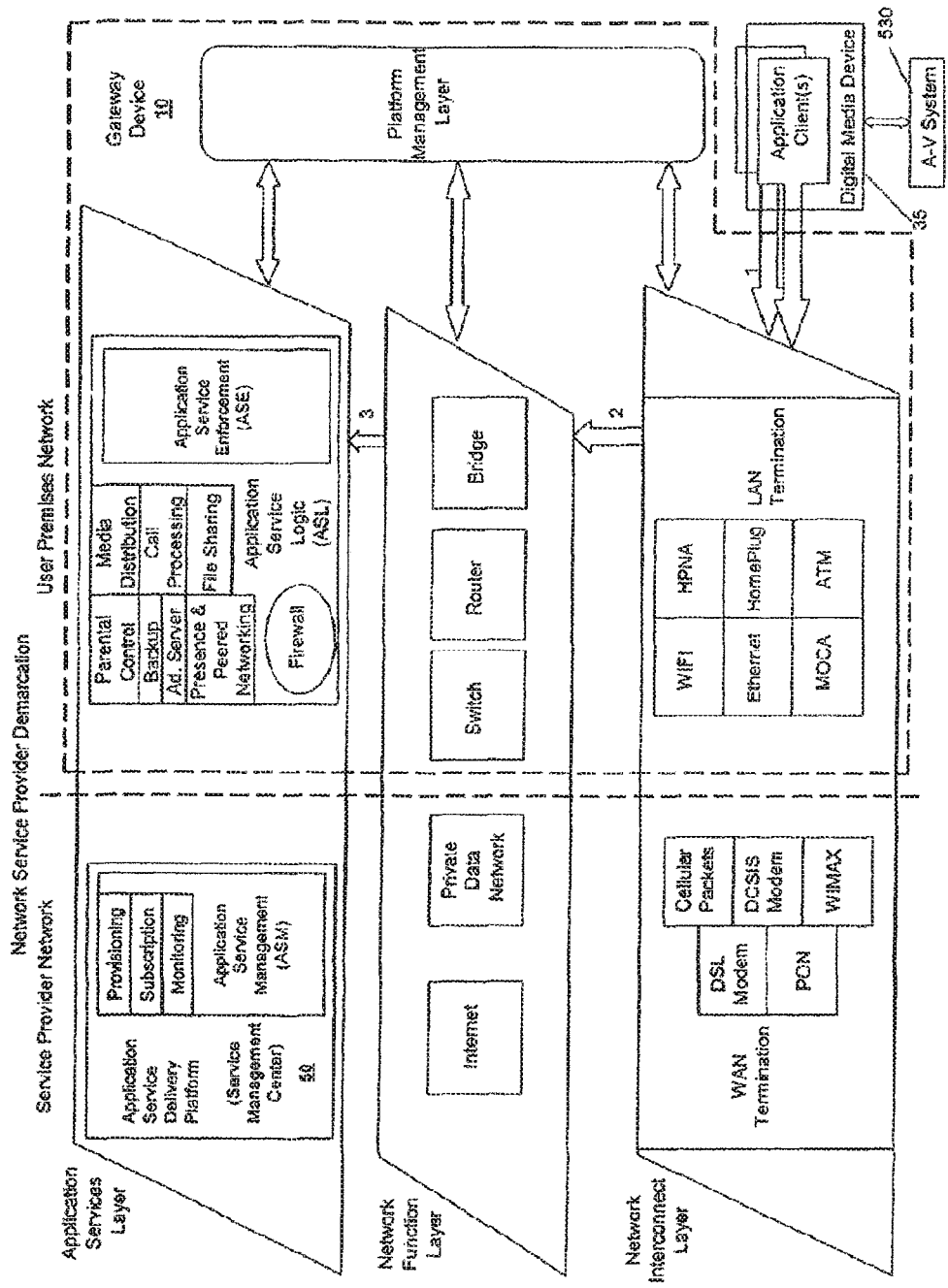
FIG. 1 is a layered logical block diagram with arrows representing steps of a sample logical flow, for an application client residing on a digital media device to access a specific managed application service, in a gateway device-service management center type network configuration.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and circuitry have been described at a relatively high-level, without detail, in order to avoid unnecessarily obscuring aspects of the present teachings.

The technology discussed herein may be embodied in a digital media device, typically for deployment at the user premises, and/or to programming for devices that may function as digital media devices.

In addition, the various technologies disclosed herein describe an application service provider device configured to offer its user many of the applications services, such as were previously offered from network-side servers, from the user premises. An exemplary application service provider as discussed herein is a gateway device in the customer premises having application service logic, where the gateway device is configured for communication with the digital media device(s) and/or with other endpoint devices. The gateway device is implemented in such a manner as to offer its user many of the applications services, such as were previously offered from network-side servers, from the user premises. As further described below, these application services comprise, by way of example, programming to simplify support services in the digital home including one or more of: media delivery, content management, access control and use tracking, file sharing, and protection and back-up services of both Internet/Web-generated digital media content and user generated digital media content. The gateway device is programmed to simplify various aspects of managing the emerging home/business digital networks including the myriad of interconnected digital endpoint devices associated with the gateway device. It is important to note that the endpoint devices need not reside within, or be located at, the premises to maintain their association with the gateway device. One or more of the digital endpoint devices may be digital media devices in a user premises communicatively coupled to a television display or to an audio-video system having a television type display, for implementing a user interface to data based application services provided through the gateway device and/or from one or more media sources. In an exemplary embodiment, the digital media device may communicate with the gateway device via a data communications link in the user premises. In an exemplary configuration, the digital media device may be integrated with the gateway device.

The technology discussed herein may be embodied in media and service distribution systems, that may include gateway type devices and associated digital media device, which provide application service logic in the customer premises. The media and service distribution systems embodied herein may also include one or more media sources associated with the digital media device. Although based on a Client-Server architecture, the exemplary gateway device and service management center move substantial functions performed by the typical network server into the user premises by incorporating those functions into the gateway device, but in a way that allows for the server functionality to be externally managed by the service management center from the network side, which may be operated by a third-party service provider. In this architecture, both the server functionality and the application services offered via the gateway device to the digital media device may be managed by the service management center. Moreover, the server function residing in the gateway device is not only located in the premises but also resides logically on the premises side of the Network Service Provider demarcation. The applications offered via the user's digital media device in a media and service distribution system may be managed by a gateway type device or by a service management center.

The gateway device and the system architecture effectively place a set of application services on a tightly coupled (e.g., always-on or always-available basis), secure hardware platform that is externally managed. A digital media device that is associated with the gateway device in turn provides a user interface, e.g., for the "ten-foot" interface via a television and/or other audio-video system, for the application services. The gateway device comprises application services programming, and associated hardware, that is positioned on the user premises side of the Network Service Provider Demarcation, which is configured to be managed by an external service management center. The gateway device and the external service management center may provide application services to the digital media device positioned within the user premises.

The digital media devices, as well as the media and service distribution systems, may be implemented in such a manner as to offer users a selection from a variety of media from various media sources, as well as many independently provided application services, from the user premises.

Reference now is made in detail to the examples illustrated in the accompanying drawings and discussed below. FIG. 1 is a high-level diagram of the architecture of the gateway-service management center network as disclosed herein, as well as the logical flow of how a specific Application Client residing at a User Premises could interact with Application Service (AS) logic in a gateway device 10 that is being managed in the gateway-service management center network configuration. Gateway device 10 in the example delivers a number of application services to associated endpoint devices, including at least some endpoint devices within the premises. The associated endpoint devices implement Application Clients. For example, as shown in FIG. 1, one or more specific Application Clients may reside on a digital media device 35 within the user premises that may be communicatively coupled to audio-video system 530. The Application Clients residing on digital media device 35 may interact with a server functionality for an Application Service, provided by the on-premises application service layer logic in a gateway device 10 to deliver applications and/or services to audio-video system 530 in the user premises.

In the illustrated architecture shown in FIG. 1, application services logically reside at the Application Service Layer (AS Layer) in the User Premises Network, i.e., on the hardware components located in the user premises, such as, by example, a gateway device 10. In contrast, such application services traditionally were offered from network-side servers on the Service Provider network side of the Network Service Provider Demarcation. In the exemplary architecture only a management function for the application service layer remains on the service provider side of the demarcation line, for example, in a service management center 50.

Gateway device 10 of FIG. 1 may provide applications and services to an audio-video system in a user premises via an Application Client residing on digital media device 35. In particular, the programming that implements application services is logically positioned on the user premises side of the Network Service Provider Demarcation. The application service on the user premises side that enforces authorization, authentication, configuration, or use of the respective service via an endpoint device (e.g., digital media device 35 and associated audio-video system 530) is logically depicted in FIG. 1 as the Application Service Enforcement (ASE) module in the AS Layer of the User Premises Network. The ASE module may also communicate via the wide area network with the Application Service Management (ASM) logic residing in service management center 50.

As discussed more below, the Applications Services Logic (ASL) and the ASE functions shown in FIG. 1 are implemented on the User Premises side as high-level server type logic within gateway device 10. Other elements shown in FIG. 1 that may reside in gateway device 10 include the user premises-side network function or NF (switch, router or bridge) and the local area network (LAN) termination for communication with the endpoint devices implementing the application client functions. Thus, with reference to FIG. 1, the first interface for enabling bi-directional network layer communications on the user's side of the premises with one or more of the associated endpoint devices resides at the Network Interconnect Layer (NI) Layer and provides the LAN Termination referenced therein. FIG. 1 also depicts the wide area network (WAN) termination providing connectivity to the wide area network (network-side NF-Internet or private wide area data network). One or more of the associated endpoint devices may be digital media device 35 (as illustrated in more detail in FIGS. 2 and 3) communicatively coupled to a television display or to audio-video system 530 having a television type output. The second interface of gateway device 10 for enabling bi-directional network layer communications for the associated endpoint devices via a wide area network resides at the NI Layer and provides the WAN Termination referenced therein. The second interface of gateway device 10 also enables bi-directional communications between it and the service management center via the WAN.

With reference to FIG. 1, the core of the logical capacities of service management center 50 resides on the Service Provider Network, and is depicted as the Application Service Management (ASM) portion of the Application Service Delivery Platform in the AS Layer. The ASM function is implemented in service management center 50, which is external to the user premises, and, perforce, on the network side of the demarcation line. The ASL and ASE functions maintain logical connectivity or interaction with the ASM function in service management center 50, typically via communication through a wide area network. This logical connectivity is established through an always-on (or on an as needed, periodic basis), secure communication channel between the User Premises AS Layer (ASL and ASE) in gateway device 10 and the Service Provider AS Layer (ASM) at service management center 50. Service management center 50, and the communications of service management center 50 with one or more of gateway devices (e.g., gateway device 10), provides an infrastructure support and/or management of the application services offered to associated endpoint devices and their users by the logic implemented in the gateway device(s) 10. As further described herein, one or more of the associated endpoint devices may be a digital media device (e.g., digital media device 35) communicatively coupled to a television display or to an audio-video system (e.g., audio-video system 530) providing a television type output. Effectively, the Application Service Delivery Platform (ASD), considered in its entirety, extends all the way to the User Premises and traverses the Network and Network Service Provider Demarcation. The secure communications channel is established through the NF Layer and the NI layer.

The examples discussed herein also introduce a logical platform management layer to the user premises-side, which allows for inter-layer allocation of local resources so as to provide applications and or services to digital media device 35 residing within a user premises. This function guarantees access between the Application Service Logic function on the user premises network and the applications service management function in service management center 50 by assuring that the local user premises hardware (e.g., digital media device 50) and software modules are functioning at a required state (CPU and memory usage, bandwidth usage, QoS settings, etc.) in order for the ASL to have the necessary resources to establish its required communications path to the ASM.

The platform manager is also responsible for implementing that part of the managed application services to be performed by gateway device 10. In that regard, the platform manager secures and manages the overall hardware platform, given that in this scenario, the NF layer and the AS layer reside on one hardware platform. This secure hardware platform provides a robust and secure operating environment for the AS Layer. So, to establish a secure and robust hardware operating environment, the platform manager must interface with all the layers above it and allow for bi-directional management information flow among all of the functions. For example, if the Application Client residing on digital media device 50 is a telephony application and the desired application is call processing, the application must first connect to the LAN termination interface (1). Then a connection must be established to the AS Layer through the NF layer (2). At this point the platform manager determines if there are sufficient resources available for this to take place on the routing and switching modules and if there is not sufficient resources on either the LAN Termination interface or the NF layer functions, it would take the necessary corrective measure to free up the required resources so that the application can execute properly (e.g.

prioritize packets, throttle bandwidth, attempt to reduce noise on an RF (radio frequency) interface, or free up time slices on a TDMA interface such as MoCA). Once that is done, the connection is established to the AS Layer (3), where the ASE and ASL, having been updated by the ASM in the network, respond instantaneously to the Application Client of the digital media device, completing the service request.

Application services represent functionalities, implemented in the higher layer(s) of the protocol or logical stack above the network layer(s) that may extend up to the top application layer (layer 7 of the OSI model). An application service, for example, provides application server communication with a client functionality of one or more endpoint devices, for the respective service, communicated on top of network layer communications through the interfaces. In the examples, the services are provided on a subscription service basis to users at the premises, where the one or more endpoint devices may be digital media device 35 communicatively coupled to a television display or to audio-video system 530 having a television type output. As described above, one or more the application clients may be residing on digital media device 35. Hence, the application service logic provides enforcement regarding authorization, authentication, configuration, and/or use of the respective service via the endpoint devices. The application service includes service and feature functions, implemented and controlled by the application service logic. Management of the application service is based on communications with service management center 50 via the wide area network.

The illustrated architecture of the gateway device 10-service management center 50 network, along with digital media device 35 and associated audio-video system 530 within the user premises, enables other features and capabilities that have not previously been available to the user. For instance, peer-to-peer application communication between or among gateways and/or digital media devices is possible without the need to go through, or utilize resources at, an external service management center. The peer to peer communication may be enabled using a presence and networking protocol, such as an instant messaging type protocol. Communications through service management center 50 are also possible.

Given the considerable functionality present in gateway device 10, and its ability to manage the various endpoint devices associated with it (e.g., one or more digital media devices 35 coupled to a television display or to an audio-video system 530 having a television type output as explained below), the user interface with gateway device 10 and/or digital media device 35 can be presented and utilized on the home TV (e.g., television display, etc.). Additionally, information from other endpoint devices, such as the PC, network sources (such as an RSS (Really Simple Syndication) service), may now be overlaid or inserted into a display on the TV screen so that, for example, PC messages, or weather information, can be viewed on the TV screen, and the functionality of the PC (or other home-networked endpoint devices) can be accessed from the TV screen. Gateway device 10 and its role in a media and distribution system for a user premises having digital media device 35 is discussed below in connection with FIGS. 2 and 3.

Media and Service Distribution System

Figure 2:
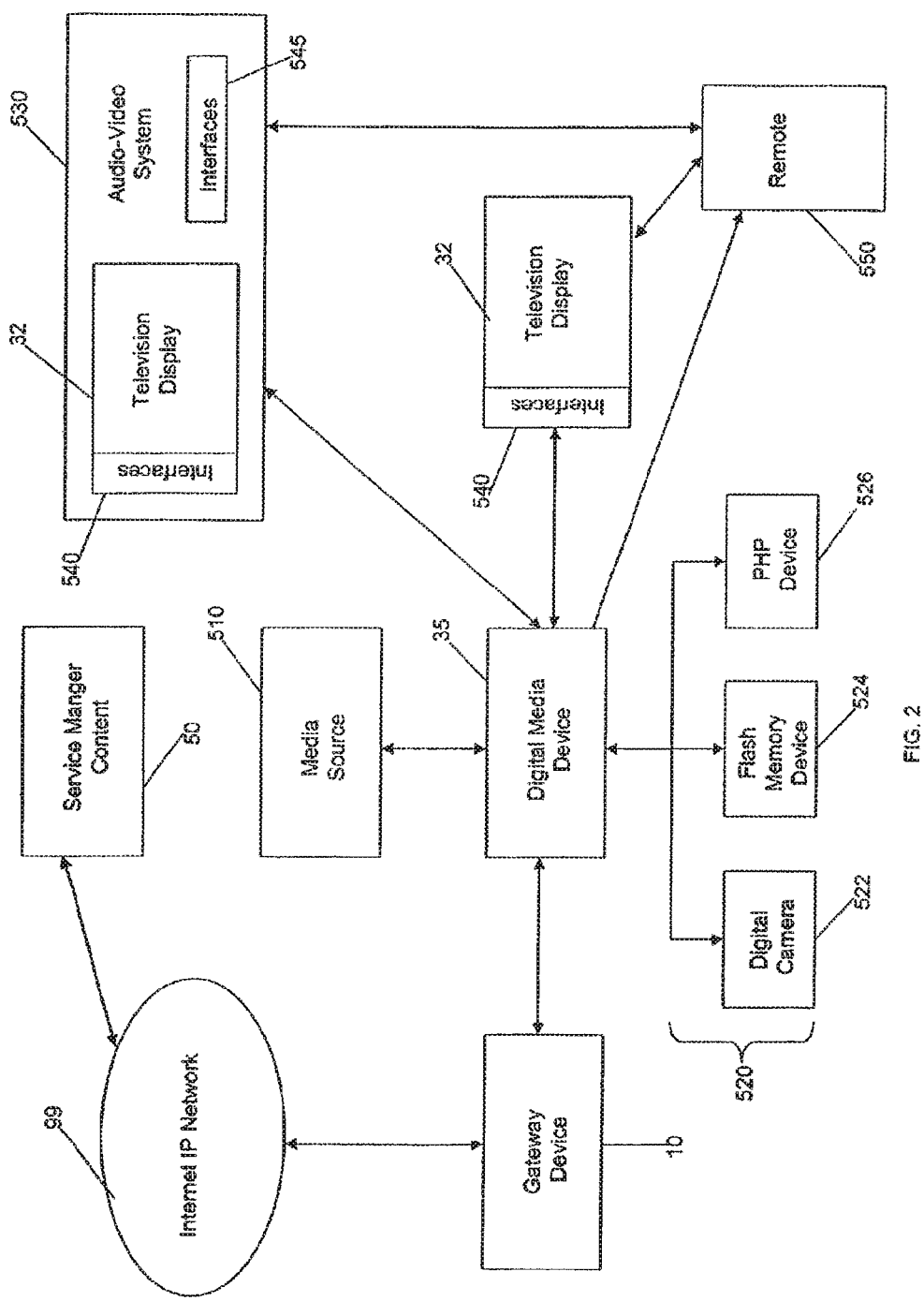
FIG. 2 illustrates a block diagram depicting a media and service distribution system.

FIG. 2 illustrates media and service distribution system 500, with gateway device 10, digital media device 35, media source 510, and television display 32 having interfaces 540. FIG. 2 also illustrates an alternative arrangement, where digital media device 35 is communicatively coupled to audio-video system 530 that includes television display 32 and interfaces 540. Accordingly, as described throughout, television display 32 may operate with digital media device 35, or may operate as part of audio-video system 530 with digital media device 35.

Figure 5:
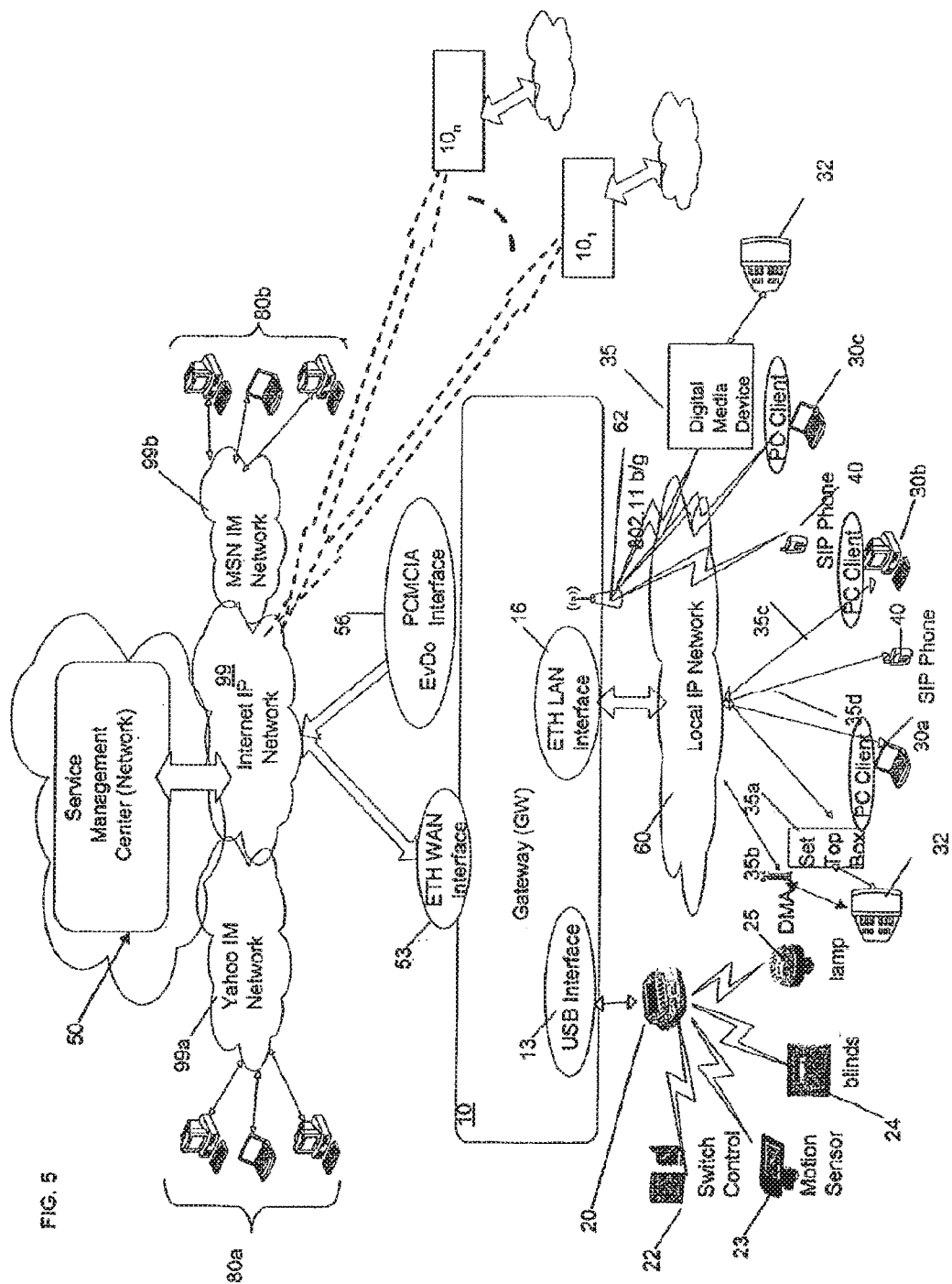
FIG. 5 is a network diagram, depicting a gateway device, endpoint devices at the user premises, one or more wide area networks and a service management center.

Digital media device 35, as described throughout, may be a set top box (e.g., set top box 35a illustrated in FIG. 5) or digital media adaptor (e.g., digital media adaptor (DMA) 35b, shown in FIG. 5). Digital media device may also have a data communications link in the user premises with gateway device 10. In an exemplary embodiment, gateway device 10 and digital media device 35 may be integrated into a single device, or gateway device 10 and digital media device 35 may be coupled together via a data communications link. One or more of the associated endpoint devices of media and service distribution system 500 may be digital media device 35 communicatively coupled to television display 32 (e.g., which may be separate from or included with audio-video system 530). Digital media device 35 may present a graphical user interface for at least part of a display (e.g., an insert or overlay) on television display 32 for enabling a user to selection applications, services, media, or any suitable combination thereof.

Gateway device 10 may communicate with digital media device 35 via a wired or wireless communicative coupling serving as the data communication link within the user premises. The data communications link may be, for example, a user premises data communications network, a USB (Universal Serial Bus) link, or any other suitable communications link. For example, gateway device 10 may utilize a Wi-Fi wireless network or an Ethernet wired network in order to communicate with digital media device 35. In addition to being communicatively coupled with digital media device 35, gateway device 10 may be communicatively coupled via a wireless link or wired link to wide area network 99. The wide area network 99 enables communications with the application service management center 50, which may, at least in part, provide and manage applications provided to gateway device 10 and digital media device 35. Digital media device 35 may be communicatively coupled with gateway device 10 via a wired Ethernet connection or other suitable wired connection. For example, the digital media device may communicate with gateway device 10 via Ethernet and a HTTPS connection to render application services to, for example, television display 32. Alternatively, digital media device 35 and gateway device 10 may be communicatively coupled via wireless communication.

As shown in FIG. 2, digital media device 35 may be communicatively coupled with various digital storage devices 520, which may include, but are not limited to digital camera 522, Flash memory device 524, personal media player (PMP) device 526, etc. Digital media device 35 may have at least one interface, such as a USB (Universal Serial Bus) interface, to communicatively connect devices such as cameras, portable media players, flash memory drives, or other storage based devices to digital media device 35 directly.

Digital media device 35 may be configured to support a fixed media mode in order to be recognized, since fixed media mode allows the device's contents to be viewed as files. Exemplary devices (e.g., devices 522, 524, 526, etc.) may be represented as a mapped drive on gateway device 10 and available for access by a personal computer (e.g., computer 30a or 30b shown in FIG. 5) or other device and digital media device 35 for displaying pictures, playing music, rendering movies, or presenting other audio and/or video media. Digital media device 35 may be configured to automatically detect the connection of a USB device or other similar device, and generate a notification message for display on television 32, which may be part of audio-video system 530. The notification may contain the name, type of device, and/or other related information. The size and position of the notification displayed on the television may be configurable. An icon or other graphical indication may be displayed on the television display in order to identify the connected device. Preferably, the icon or other graphical indication may be present on the television display during the period that the device is connected with digital media device 35.

Digital media device 35 may be communicatively coupled with a display device such as television display 32 having one or more input/output interfaces 540. Alternatively, in the case of audio-video system 530, digital media device may be communicatively coupled with television 32 of audio-video system 530 via interfaces 540, and/or may also be communicatively coupled to audio-video system via interfaces 545. Interfaces 540 and 545 may include component video, S-video, HDMI (high definition multimedia interface), composite video, analog audio, digital audio, or any other suitable interface.

Digital media device 35, television display 32, and/or audio-video system 530 may be controlled by remote 550 via a wired or wireless communication system (e.g., using infrared (IR) signals, radio frequency (RF) signals, etc.). As illustrated in FIG. 9 and described below, digital media device 35 may have remote control interface 640 to support communications between remote 550 and digital media device 35. Digital media device 35 may be configured to support the processing of signals from remote 550, and digital media device 35 may also configure remote 550 to control the functions of other devices, e.g., television 32, audio-video system 530, etc. Remote control 550 may have a number of buttons for interacting with the graphical user interface (e.g., as illustrated in FIGS. 8A-10D and 12A-12I that may be, for example, presented on television 32. Remote control 550 may have various function keys or buttons that include, but are not limited to directional buttons (e.g., up, down, left, right, etc.), functional buttons (e.g., stop, play, pause, next, back, fast-forward, rewind, skip, page up, page down, select, zoom in, zoom out, etc.), a numeric keypad, or any other suitable set of buttons for interactive user input. Remote control 550 may be configured to support a library of codes or commands for controlling other devices such as television 32 and media source 510 (e.g., DVD players, VCRs, DVRs, etc.). Those skilled in the art will recognize that other user input devices may be used, in place of or in addition to the remote control 550.

As shown in FIG. 2, digital media device 35 may also be communicatively coupled with media source 510. Although one media source 510 is shown for simplicity, digital media device 35 may be communicatively coupled to multiple media sources. Media source 510 may be an in-premises analog or digital cable television distribution or the like, a video cassette recorder (VCR), a video game console, a digital video recorder (DVR), a digital versatile disc (DVD) device, an analog or digital broadcast television signal, an analog or digital cable headend, a satellite television signal source, an analog or digital radio broadcast, or an Internet source providing audio, video, or both audio and video, any suitable combination thereof, or any other media source.

Digital media device 35 may support a plurality of different audio and video input and output interfaces (as further discussed below in connection with FIG. 3). For example, digital media device 35 may have video interfaces HDMI, component video, composite video, S-video, or any other suitable interfaces. Digital media device 35 may also have an interface to support at least one tuner, at least one data port, any combination thereof, or any other suitable interfaces. Digital media device 35 may have a digital audio interface (e.g., Sony/Philips Digital Interface Format (S/PDIF)) or an analog audio interface, or any other suitable audio interface. The audio interfaces may be paired or integrated with the analog or digital video interfaces. The video interface may, for example, support a plurality of standard definition video streams, a plurality of high definition video streams, or a combination of standard and high definition video streams. In addition, the wired network interface and/or the wireless network interface of digital media device 35 (as discussed below in connection with FIG. 3), may support digital audio streams, digital video streams, or audio and video data streams, or be configured to receive digital audio and/or video data files.

Digital media device 35 may support picture-in-picture (PIP) functionality, and may further support the ability for a user to configure the size and location of the PIP window within a display (e.g., a display presented on television display 32). Digital media device 35 may support picture-outside-picture (POP) where a plurality of windows of video may be displayed in an arrangement relative to a main video display window. For example, the POP windows may be displayed around the edge of the main video display window. Digital media device 35 may be configured to adjust the size and position of the main POP window, as well as configure the size, position, and number of secondary windows for POP. In addition, digital media device 35 may support the display of two windows of video side-by-side. Digital media device 35 may also support picture-in-graphic (PIG), where a video image may displayed in a window within a separate graphical image. Digital media device 35 may be configured to toggle video displays between the main window and secondary windows for PIP, POP, PIG, and side-by-side. Digital media device 35 may be configured to receive a signal (e.g., from remote control 550) to change the focus between the main windows, secondary windows, side windows, or graphical area, or any suitable combination thereof. Digital media device 35 may be configured to receive a selection (e.g., from remote control 550) as to an audio signal or stream to be played by a television or audio/video system for PIP, POP, PIG, side-by-side, or composite video images (e.g., overlays or insert displays), or any suitable combination thereof.

Figure 3:
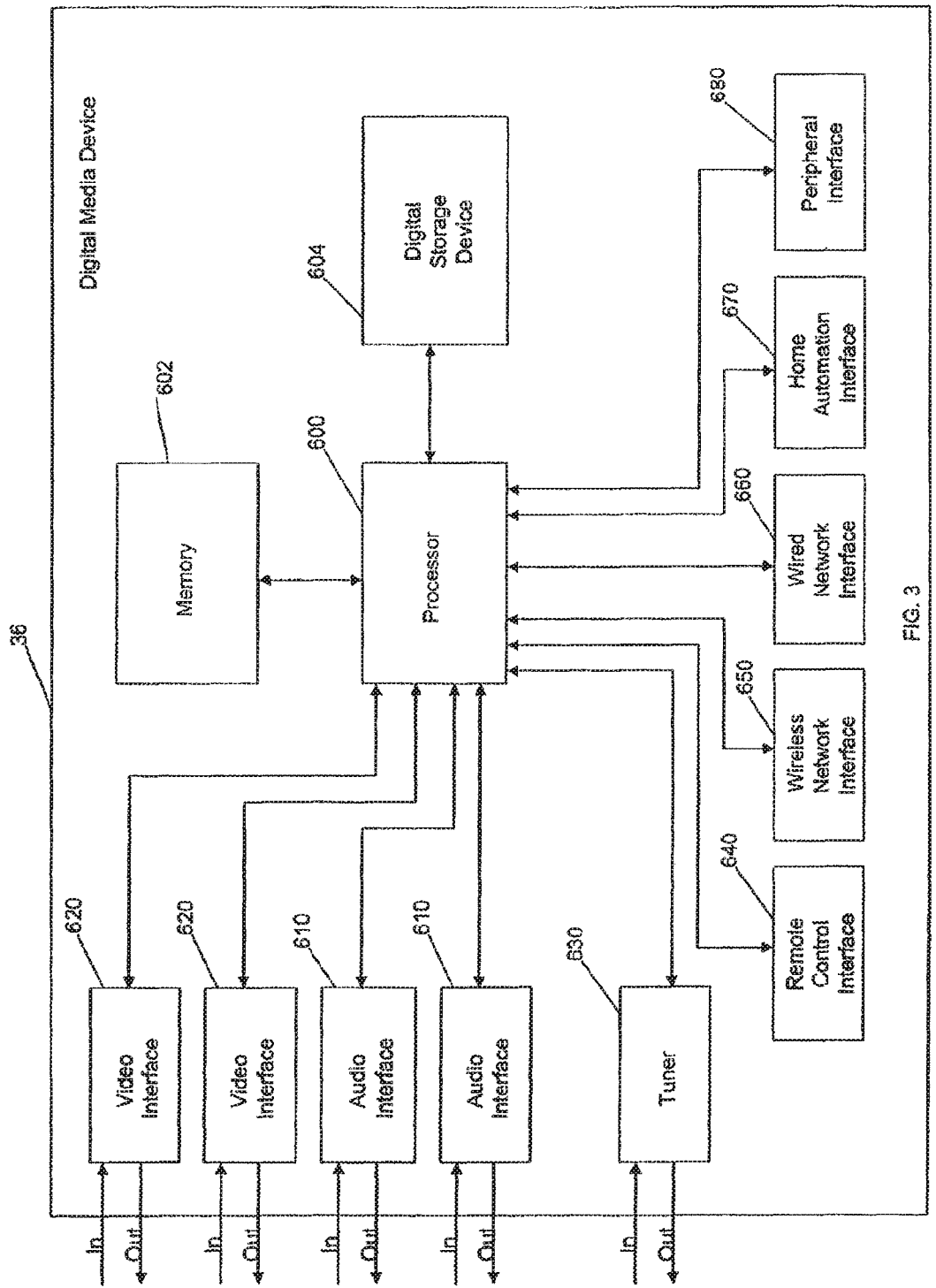
FIG. 3 illustrates a functional block diagram of an exemplary digital media device shown in FIG. 2.

Audio or video files stored on gateway device 10, audio or video signals received via wide area network 99, or audio or video received via media source 510 may be passed through to at least one audio or video interface of digital media device 35 and/or may be received via a network interface (e.g, wireless network interface 650 or wired network interface 660 illustrated in FIG. 3). A plurality of video streams (e.g., a plurality of digital video streams, a plurality of analog video streams, or a plurality of analog and digital video streams) may be integrated to form a composite signal, which may be used to display a composite display on television display 32, or present a composite signal for presentation on audio-video system 530. This plurality of video streams that may be combined to form the composite signal may be integrated with at least one analog audio signal or digital audio signal, where the audio signal may provide audio substantially contemporaneously with the composite image. Alternatively, a plurality of audio signals may form a composite signal and may be played on audio-video system 530.

These capabilities of the digital media device enable presentation of an interactive graphical user interface for application services offered through the gateway device 10, e.g. from the wide area network, to television display 32. For example, the GUI may provide audio and/or video output via a television presentation and allow user input via the remote control 550. The GUI allows the user to select and interact with gateway enabled services. Such services may include, but are not limited to: viewing movies; viewing photos; playing music; controlling home devices of an in-home network; playing video games; controlling security features such as parental control; file backup; or any other suitable functions. The GUI also offers various notification and response functions, for example, receiving notifications of voicemail, incoming calls, or alert or update messages from devices connected to an in-home network or via wide area network, or weather updates, or other suitable notifications, alarms, or messages.

DRM and Non-DRM Content

Digital media device 35 may be configured to acquire, store, and execute a device application for playing protected content (e.g., audio, music, video, etc.). The device application may be utilized to decrypt or unlock protected content for playback as authorized by the content provider's license and terms of use. The application may be represented by the content providers (CP) license manager and may be stored on digital media device 35. Each content provider shall have their own license manager stored on digital media device 35.

Digital media device 35 may be configured to access content stored on or available from gateway device 10. The content may include DRM (Digital Rights Management) and non-DRM content. If the accessed content has DRM, then digital media device 35 may acquire the license related to the DRM content and then render the content to the user subject to the use limitations set by the content and/or service provider rules of the DRM license. For example, digital media device 35 may support rendering of the WMDRM (Windows Media Digital Rights Management) protected content. The DRM and non-DRM content may include, but is not limited to photos, music, audio, video, any other suitable content, or any combination thereof.

Content to be presented (e.g., audio, music, pictures, video, etc.) may be controlled by media control functionalities such as pause, play, stop, delete, fast forward, rewind, scan (jump forwards or backwards by x number of seconds in playback), etc. These media control functionalities may be graphically represented on a playbar that is displayed on television display 32 or other display (e.g., computer display, etc.). The playbar may be presented as an insert into or overlay onto the display of the television display 32.

Display Inserts and Overlays

Figure 7A:
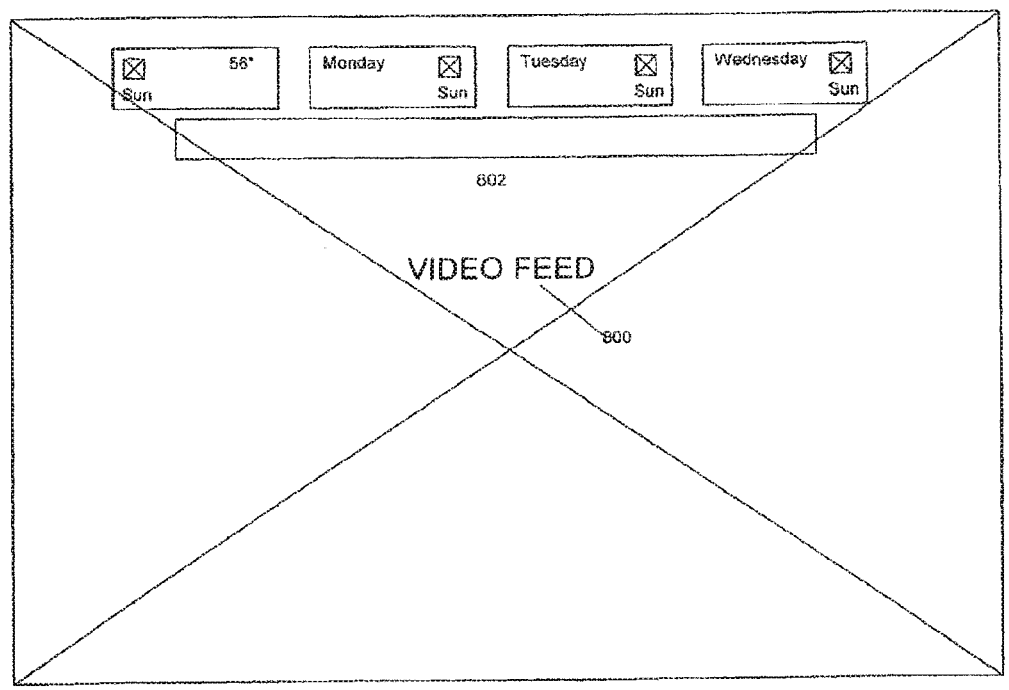
FIG. 7A illustrates a composite image of weather application service information overlaid onto a video display from a media source.

In forming a composite signal, digital media device may use at least one signal from media source 510 to form a primary image and may use application service information from gateway device 10 to form a secondary image, wherein the television display is configured to display the secondary image overlaid on or inserted into the primary image to form the composite image. For example, FIG. 7A illustrates a video display of TV program images 800 from media source 510 as a primary image, and weather information 802 obtained via the gateway device 10 overlaid onto video display images 800 as the secondary image. Alternatively, application service information (e.g., obtained via gateway device 10) of the composite signal may form a primary image, and at least one media signal (e.g., via media source 510) form a secondary image, wherein the television display (e.g., television display 32) is configured to display the secondary image overlaid on or inserted into the primary image to form the composite image. Digital media device 35 may also form a composite signal from at least one an audio signal from the application service information from gateway device 10 or from media source 510, where the audio signal provides audio substantially contemporaneously with an image or composite image on television display 32. The audio information regarding the application service from the gateway device 10 may be inserted as a segment in place of regular program audio or mixed with the regular program audio signal. Digital media device 35 may also be configured to form an audio signal as a composite of audio of a media signal from media source 510 and audio information of the application service information from gateway device 10 for presentation on audio-video system 530, e.g., with the video consisting of one or more images derived from the application service information and audio based on a composite of the program information and the application service information.

Messaging

The application service information received by digital media device 35 from gateway device 10 may include notifications of status with regard to one or more application services managed by gateway device 10. Digital media device 35 may be configured to receive the notifications of status from gateway device 10 and transmit a message related to the selection signal to the gateway device 10 using a presence and networking protocol. The presence and networking protocol may be an instant message type protocol.

Playlist

Digital media device 35 may also be configured to present a playlist (e.g., a playlist of music, audio, pictures, video, etc.) as an insert or overlay on television display 32. The playlist may be managed by a user by utilizing the overlaid or inserted interface For example, a user may utilize the interface to play from a playlist, create a playlist, add items to the playlist, remove items from the playlist, shuffle the playlist, or share playlist with comments, or any other suitable playlist function.

Photos

Digital media device 35 may be configured to display photos on a television display or other display. The size and position of each photo rendered may be configurable. Digital media device 35 may be configured to display the photos from digital storage on digital media device 35, USB devices (e.g., devices 522, 524, or 526, etc.), devices connected to wide area network 99, or devices connected to the in-home network (e.g., network 60 shown in FIG. 5). The photos may be arranged in a slideshow, and digital media device 35 may be configured to associate an audio playlist with a slideshow. Digital media device 35 may be configured to push a slideshow (with or without accompanying audio) to audio-video system 530, television display 32, or to one or more endpoint devices within the premises or to devices communicatively coupled to the wide area network. For example, such devices may be registered on a "buddy list."

Caller ID/Messaging

Figure 7B:
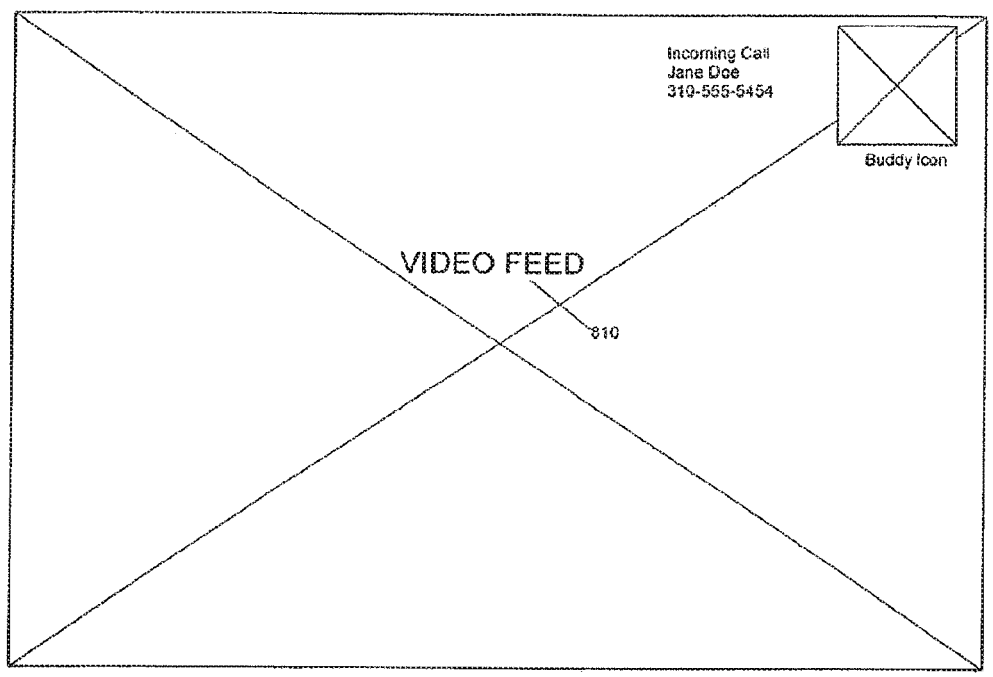
FIG. 7B illustrates received call application service information overlaid onto a video display from a media source.

Digital media device 35 may be configured to support the display of caller identification notification in an overlay or insert on the display on television display 32. For example, the notification may display graphics or images associated with the calling party number. An exemplary composite image having video image 810 with overlay 812 is shown in FIG. 7B. As shown, incoming caller phone number information 814 and caller graphic 816 overlaid on video display 810. Digital media device 35 forms a composite signal from caller information and graphics along with a media signal from media source 510. The composite signal forms the composite image, which is presented on television display 32.

In addition, a message waiting indicator may be displayed over the television when a new voicemail message is received for the current user. Digital media device 35 may be configured to sort the list of voicemail messages by the date the voicemail was left or the calling party number. The voicemail screen may identify which voicemail messages are new. Messages may be considered new if they were received after the last time the user accessed the user's voicemail box. The message waiting indicator, as described above, may be removed, e.g., by acknowledging the presence of the indicator via a selection using the remote control or my any other suitable means, or once the user accesses at least one new message.

Digital media device 35 may be configured to play voicemail messages over the television display 32 or audio-video system 530. Digital media device 35 may insert or overlay graphic controls on television display 32 to playback the voicemail, stop playback of voicemail, pause the voicemail playback, fast forward through at least a portion of the voicemail message, rewind at least a portion the voicemail message, move to the next voicemail message, or move to the previous voicemail message, delete the voicemail message, or any other suitable function.

Digital media device 35 may be configured to display a list of missed, received, or dialed telephone calls. The displayed list may be an overlay or insert on the television display or other display. The depth of the call log list may be configurable by a user. Digital media device 35 may be configured so that each number listed in a call log may be selected for dialing, or may be added to a user's contact list (i.e., address book).

Digital Media Device

FIG. 3 is a functional block diagram of an exemplary digital media device 35 shown in FIG. 2. The digital media device 35 may serve as a set-top box or as a digital media adapter for a television or other audio-video system. As shown in FIG. 3, the digital media device may have processor 600, which may be a central processing unit, application specific integrated circuit (ASIC), programmable logic device (PLD), an integrated circuit, or any other suitable processing device. Processor 600 may be communicatively coupled to memory 602 and digital storage device 604. Memory 602 may be any suitable Random Access Memory (RAM), and digital storage 604 may be any suitable non-volatile storage device, such as a hard disk drive, semiconductor memory, memory card, an or optical drive. Processor 600 may be configured to service a plurality of audio interfaces 610 with inputs and outputs, as well as a plurality of video interfaces 620 with inputs and outputs. The inputs and outputs of audio interfaces 610 may be stereo pairs (left and right audio channels). The operation of processor 600, audio interfaces 610, video interfaces 620, and additional interfaces of digital media device 35 are described in further detail below.

Digital media device 35 may also have at least one wireless network interface 650 (e.g., a Wi-Fi wireless network interface) and at least one wired network interface 660 (e.g., an Ethernet wired network interface). Digital media device 35 may communicate, for example with gateway device 10 via wireless network interface 650 or wired network interface 660. The wired network interface 660 and/or the wireless network 650 interface of digital media device 35 may support digital audio streams, digital video streams, or audio and video data streams, or be configured to receive digital audio and/or video data files.

As illustrated in FIG. 3, digital media device 35 may also have home automation interface 670 communicatively coupled to processor 600. Home automation interface 670 may be, for example, an X10, Z-Wave, or ZigBee interface, or any other suitable interface. Home automation interface 670 may enable the functionality of user interfaces (UI), access home automation, and other appliances.

Digital media device 35 may also have at least one peripheral interface 680, such as a USB interface, in order to enable communications between processor 600 of digital media device 35 and mass storage devices (e.g., devices 522, 524, and 526 illustrated in FIG. 2).

At least one audio interface 610 may be, for example, communicatively coupled to one or more devices that may comprise a media source (e.g., media source 510 shown in FIG. 2) that provides, at least in part, an audio type signal. Audio interface 610 may also be communicatively coupled to interfaces 540 of television display 32 and/or to interfaces 545 of audio-video system 530 in order to present audio type media content to audio-video system 530 or television display 32. The audio type media content may be provided by, for example, media source 510, gateway device 10, flash memory device 524, PMP device 526, or any other suitable source. In addition, audio type signals may be provided from digital storage device 604, tuner 630, wireless network interface 650, wired network interface 660, home automation interface 670, or peripheral interface 680 via processor 600, which may provide audio type signals to audio interface 610 for output for an audio type presentation. Processor 600 may also combine two or more signals received from interfaces 610, 650, 660, 670, 680, or from tuner 630 or digital storage device 604 to provide a composite audio signal to at least one audio interface 610 for output for an audio type presentation or as part of an audio-video presentation.

At least one video interface 620 may be communicatively coupled to, for example, media source 510. Media source 510 may provide, at least in part, video type signals to video interface 620, or alternatively, may provide digital audio and/or video signals via a networking communications protocol to wireless network interface 650 or wired network interface 660. In addition, at least one video interface 620 may be communicatively coupled to interface 545 of audio-video system 530 and/or to interface 540 of television 32 so that video type content may be delivered from digital media device 35 to audio-video system 530 and/or television 32 for at least some video type presentation. Additionally, video type signals may be provided from gateway device 10 (and received, e.g., by wireless networking interface 650 or wired networking interface 660), digital camera 522, flash memory device 524, PMP device 526, or any other suitable device and output to audio-video system 530 and/or to television display 32 for at least some video type presentation. In addition, video type signals may be provided from digital storage device 604, tuner 630, wireless network interface 650, wired network interface 660, home automation interface 670, or peripheral interface 680 via processor 600, which may provide video type signals to at least one video interface 620 for output for a video type presentation. Processor 600 may also combine two or more signals received from interfaces 620, 650, 660, 670, 680, or from tuner 630 or digital storage device 604 to provide a composite audio signal to at least one video interface 620 for output for a video type presentation or as part of an audio-video presentation.

At least one audio interface 610, at least one video interface 620, or a combination thereof may be used to output an audio type presentation, video type presentation, or audio-video type presentation signal generated by processor 600, where the signal may include an insert or overlay audio and/or video signal for presentation on audio-video system 530 and/or television display 32. The insert or overlay video signal may also include a graphical user interface (e.g., as illustrated in FIGS. 8A-10D and FIGS. 12A-12I. At least a portion of the programming that is executed by processor 600 to enable the graphical user interface may be at least in part on digital storage device 604.

Digital media device 35 may include at least one tuner 630 for receiving audio signals or video signals from a media source (e.g., media source 510 illustrated in FIG. 8). Tuner 630 may be communicatively coupled to processor 600. As described above, at least a portion of the signal received by tuner 630 may be output via audio interface 610, video interface 620, or a combination thereof. A signal received by tuner 630 may be combined with at least one other signal from at least one interface or device by processor 600 in order to form a composite signal which may include audio type content, video type content, or audio and video content.

In forming the composite signal, processor 600 may be configured to synchronize the audio signals and/or video signals to form a synchronized composite signal. For example, processor 600 may utilize memory 602 or digital storage device 604 to buffer the audio signals and/or video signals, and may retrieve at least a portion of the stored audio and/or video signals from the buffer in memory 602 or digital storage device 604 to edit (e.g., remove existing audio signals associated with a video signal) and synchronize the audio and/or video signals in forming the composite signal. Buffering the audio and/or video signals may be desirable for filtration of the audio and/or video signals, as well as to enable the processor to address timing delays between the received signals that are to be used to form the composite signal. For example, audio information associated with a received video signal (e.g., a television signal containing video and audio information) may be removed from the video signal, and processor 600 may retrieve the separate buffered audio signal to synchronize with the content of the filtered video signal to form a composite signal. To further illustrate the above example, the video signal may be a football game that contains audio commentary from announcers. This signal may be buffered in memory 602 or digital storage device 604, and the audio content may be filtered out by processor 600. A separate audio signal that may be audio commentary of the same football game by different announcers may be buffered by processor 600 into memory 602 or digital storage device 604. Processor 600 may synchronize the filtered video signal and the buffered audio signal to form a composite signal, such that the content of the audio signal is relevant to the content of the video signal. The resulting composite signal may present synchronized audio and video type content for presentation to a user.

Digital media device 35 may digitally record or store audio, video, images, any combination thereof, or any other suitable media received from audio interface 610, video interface 620, tuner 630, wireless network interface 650, wired network interface 660, and/or peripheral interface 680 for or playback in memory 602, on digital storage device 604, or on digital storage device 520 communicatively connected to digital media device 35. For example, digital storage device 604 may record incoming television signals from tuner 630. Accordingly, memory 602 or digital storage device 604 may serve as a buffer for audio and video data, and a user may "pause" the display of a television signal (e.g., using a remote control), and memory 602 or digital storage device 604 may continue to record the incoming television signal from tuner 630 such that a user may view the recorded television signals that are being buffered after the user de-selects the "pause" option. Gateway device 10 (as shown in FIGS. 2 and 5) may also digitally record or store audio, video, images, or any combination thereof on a non-volatile hard drive/disk magnetic and/or optical disk memory storage. For example, gateway device 10 may store audio, video, images, or other audio-visual presentations initially recorded by digital media device 35 in memory 602, digital storage device 604, or on digital storage device 520 which is communicatively coupled to digital media device 35. Recordings from memory 602, digital storage device 604, or digital storage device 520 may be transferred (e.g., in response to instructions received from service management center 50) to gateway device 10 so as to increase the available digital storage available in the user premises. Recorded audio, video, images, or audio-visual presentations that have been transferred to gateway device 10 may be retrieved as requested by a user (e.g., digital media device 35 may receive a selection from a user for recorded audio, video, or audio-visual presentation, and digital media device may retrieve the selection from the digital storage of gateway device 10 for presentation on television display 32 or audio-visual system 530).

Digital media device 35 may also have remote control interface 640, which may be communicatively coupled to processor 600. Remote control interface 640 may be configured to receive wireless signals (e.g., infrared signals, radio frequency signals, etc.) from remote 550 illustrated in FIG. 3 and described above. Remote 550 may be used to select applications or media sources presented to the user on television display 32 and/or audio-video system 530.

The description provided below further details providing and managing application services to a gateway device and to a digital media device.

Managed Application Services Delivery Platform

Figure 4:
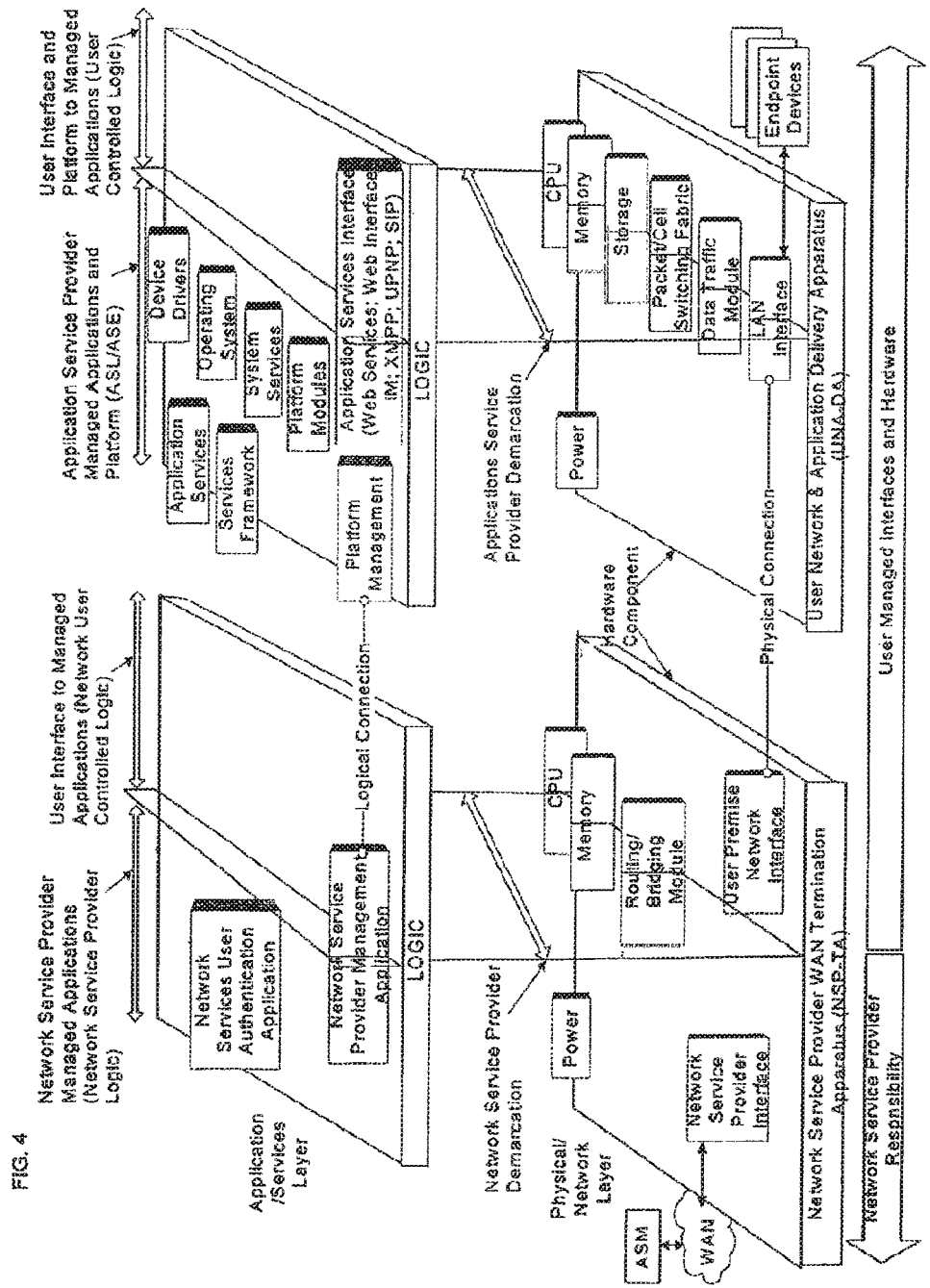
FIG. 4 depicts a managed application services delivery platform.

FIG. 4 depicts, at the Physical/Network layer shown therein, an example of user premises hardware components required for delivering data services (i.e. Internet connectivity) along with a separate, non-integrated managed hardware used in delivering a set of managed application services (e.g. VOD, IM, home automation, IP telephony). As will become apparent from the further discussion, some or all of the elements will form a gateway device at the network edge, for communication with endpoint devices including a digital media device.

The Network Service Provider Wide Area Network Termination Apparatus (NSP-TA) allows for a typical termination of Wide Area Network Services, such as DSL, Cable, Fiber, etc, by a network services provider. The NSP-TA provides the WAN Termination in the NI layer (FIG. 1). The NSP-TA may be an existing user-premises device, provided by the carrier supplying network services to the premises, FIG. 4 also depicts the Network Service Provider Demarcation at the hardware level.

If configured as a standalone device, the NSP-TA device is required to have its own CPU, Memory, physical interfaces and logic control. In order for Network Service Providers to deliver managed services, they typically require a management element controlled by the CPU on the NSP-TA. To depict these logical elements residing on the hardware components, FIG. 2 includes an Application/Services Layer above the hardware layer. This layer corresponds to the AS Layer of FIG. 1, but without reference to any logical elements residing at the network services provider. The management element, represented by the Network Service Provider Managed Application, allows the network service provider to determine the status of the network hardware device and interfaces as well as maintain a certain degree of security enforcement at the customer premises. As noted, the network service functionality is at the NI and NF Layers and generally does not extend to the AS Layer(s) beyond basic authentication authorization and state management. As with the hardware components, the logical elements also have a Network Service Provider Demarcation as shown in FIG. 4. On the WAN side, depicted as the Network Service Provider Managed Applications side, of the Network Service Provider Demarcation, resides the applications that are managed, and under the exclusive control, of the network service provider (the Network Service Provider Logic). The User Interface to Managed Applications is present on the LAN side of the Network Service Provider Demarcation within the Application/Services Layer. Within this interface resides programming and logic available to users other than the network service provider referred to as the Network User Controlled Logic. The Network User Controlled Logic, which is depicted at the Application/Services Layer in FIG. 4, provides a user interface to the Network Service Provider Logic and, to the extent permitted by the Network Service Provider Logic, interaction with or communication between the user and network service provider through the Network User Controlled Logic and the Network Service Provider Logic, and to the NSP-TA hardware components. The Network User Controlled Logic allows for the User of the hardware to make certain, minimal programming changes relevant to their preferences (e.g., user name and password changes, local IP addresses changes, local interface selection). All user devices typically can only communicate with the NSP-TA through one or more of the User Premises Network Interfaces. The user can modify the Network User Controlled Logic through the User Premises Network Interface. The Network Service Provider Demarcation is typically within the NSP-TA, logically dividing the Network Service Provider Interface and the User Premises Network Interface modules. The network service provider does not have any in depth visibility or significant responsibility beyond the Network Service Provider Demarcation.

The User Network and Application Delivery Apparatus (UNA-DA), shown on the right hand side of FIG. 4, is a separate managed gateway device that a managed service provider (which may be different than the network service provider) would control in delivering a set of application services to the user premises (e.g., to a digital media device). This device is required to have its own dedicated CPU, memory, logic control, as well as its own dedicated set of interfaces. The UNA-DA includes one or more Network Interfaces providing connectivity to the NSP-TA as well as to user premises endpoint devices (e.g., digital media device 35 that is coupled to audio-video system 530 and/or television display 32 in FIG. 2, etc.). The interfaces provide the LAN Termination functionality at the NI Layer (FIG. 1). One skilled in the art will readily recognize, however, that the physical connection that connects the UNA-DA to the NSP-TA also provides connectivity for the UNA-DA to the public (WAN side) network, and is the means by which the UNA-DA accesses the public network. The end point devices connected to the LAN Interface are on the private (LAN) side of that interface. The UNA-DA also includes a switch, router or bridge for the NF Layer.

Programming elements of the UNA-DA are depicted at the Application/Services Layer of the UNA-DA. Certain logical elements, depicted as the Application Service Provider Managed Applications and Platform in FIG. 4, on which resides, inter alfa, the programming corresponding to the ASL and ASE of FIG. 1, are managed by the managed application service provider's network control center, e.g., by the ASM of service management center 50 through a wide area network (WAN) by means of a control channel to the Application Service Provider Managed Applications and Platform. The Application Service Provider Managed Applications and Platform includes a platform management logic module that, with other programming in the Platform and the ASM, allows the managed application service provider to control the hardware elements of the UNA-DA in addition to any other relevant application services logic or hardware that may reside on the user premises. For example, this programming enables managed application service provider to control and manage the hardware elements on the UNA-DA to ensure proper use and allocation of the UNA-DA's processing, memory, storage, and bandwidth, to monitor local hardware security and generate needed alarms or protection sequences, and to prioritize applications based on a set of established policies. The user would have control over specific parameters of the UNA-DA through the User Interface and Platform to Managed Applications (User Controlled Logic) shown in FIG. 4. These parameters allow the user to control the local behavior of the interfaces and to configure the specific applications to accommodate the user network as configured by the user and to implement the user preferences for those applications.

To identify the separation of, and distinguish between, the programming and hardware components subject to control by the managed service provider and those subject to control by the user premises, FIG. 4 identifies a dividing line across the logical elements of the UNA-DA, and a corresponding dividing line across hardware components, referred to as the Applications Service Provider Demarcation. The Applications Service Provider Demarcation is flexible in that it may extend logically through the Application Services Interface (and, in a hardware context, through the Network Interface) to other devices that are under the logical control of the Application Services Provider Managed Applications and Platform, given that "services" are not restricted to a specific hardware boundary.

There is no hard requirement for cross management between the LINDA-DA and the NSP-TA. Under this first scenario the user is responsible for making the configuration changes in the specific user controlled logic modules in order to get the two devices to communicate with each other. Optionally the two sub-systems can be combined together, either physically in one hardware device, or logically as two separate hardware devices, but having one user managed interface.

The two hardware regimes described above (NSP-TA and the UNA-DA) may be combined into one managed hardware platform and, thereby, replace the need for the user to have access to the User Premises Network Interface with the logic residing in the Platform Management logic module of the Application Service Provider Managed Applications and Platform. This would in effect replace the "user" access with a managed "machine" access, for aspects of the NSP-TA, as well as aspects of the application services offered through the UNA-DA. Thus, the combination creates an integral gateway device providing both network service and application services, under centralized management. Although integrated, network interconnect functions of the NSP-TA may still be managed by the network service provider, as in the example of FIG. 4. Those skilled in the art will readily see additional combinations and configurations for the hardware comprising the NSP-TA and the UNA-DA. For example, in a further embodiment, all the hardware dedicated to the Network Service Provider Interface may reside and be integral with the hardware comprising the UNA-DA. Thus, the hardware for the WAN interface may reside on the UNA-DA.

It may be helpful now to consider more detailed examples of the gateway device-service management center network.

Gateway Device and Service Management Center Elements-Overview

Those skilled in the art will recognize that functions of the service management center, which reside in the Application Service Management node on the Service Provider Network, as depicted in FIG. 1, may be implemented in a variety of different ways, on one or more computer hardware platforms connected to the gateway devices via a wide area network. FIG. 5 depicts an example wherein the implementation is on Internet or other wide area IP network 99. The example uses a distributed processing approach, in which the elements/platforms implementing the service management center are interconnected for communication and for wide area communication, and in this way, those elements form a network 50 for implementing the service management center.

As shown in FIG. 5, the service management center network, through the logical capabilities earlier depicted in FIG. 1 as the ASM module of the ASD Platform at the AS Layer, manages application services for a number of gateway devices 10, 10.sub.1 . . . 10.sub.n located at various users' premises. These application services, shown as ASL and ASE in FIG. 1, implement their functionality within the Application Services Layer (FIG. 1), through programming that resides, at least in part, within the Application Service Provider Managed Applications and Platform of the UNA-DA (FIG. 4). As shown in FIG. 5, secure connectivity to the service management center network 50 is provided, in one embodiment, via a WAN Termination interface, such as Ethernet WAN 53 over a broadband connection via the public Internet 99, or, for example, via a wireless EvDO (Evolution Data Optimized) Internet data interface embodied as a PCMCIA (personal computer memory) wireless card 56. When the WAN Termination interface 53 is used, for example, it may provide connectivity to a broadband modem serving as the NSP-TA of FIG. 4, either as a separate unit or on a board included within the gateway device 10. If the wireless WAN interface is used, there may be no physical NSP-TA device, and the logic of the gateway device would implement functions of the NSP-TA as well.

As will be described in greater detail herein below, the service management center 50 generally provides a communications and processing infrastructure for supporting the variety of application services and related communications residing at the gateway devices 10, 10.sub.1 . . . 10.sub.n. In an exemplary embodiment, this infrastructure may be configured to provide a secure environment and may be IP-based. Preferably, this support architecture is designed for high availability, redundancy, and cost-effective scaling.

The secure platform for building and providing multiple application services for digital endpoints associated with a gateway device requires communication connectivity between the gateway device 10 and each of a user's devices (referred interchangeably herein as "endpoint devices" or "digital endpoint devices" throughout, and where one or more of the endpoint devices may be a digital media device communicatively coupled to a television display or to an audio-video system having a television display type output). Some associated endpoint devices may communicate with the gateway device via a public network, e.g., when a user of the endpoint device roams outside the user premises. In most examples, the digital media device will be within the premises, and the communications between the gateway device and the digital media device will utilize local in-premises data communication connectivity. This connectivity may be provided by implementation of one or more USB ports (interfaces) 13, a wired Local Area Network connection such as provided by an Ethernet local area network (LAN) interface 16, or, a wireless network interface via a WiFi LAN access point 62 provided, for example, in accordance with the I.E.E.E. 802.11b/g/n wireless or wireless network communications standard. These physical interfaces provide the required network interconnectivity for the endpoint devices to connect to the multiple application services. Although not shown in FIG. 5, this connectivity between digital endpoint devices and the gateway device may be accomplished by other means, including, by way of example, through of a virtual private area network connection accessed through a WAN interface.

That is, the gateway device 10 interfaces with digital endpoint devices including, but not limited to: a home automation networking device 20 (e.g. X10, Z-Wave or ZigBee) for wired or wireless home network automation and control of networked home devices such as a switch controller 22, sensor devices 23, automatically controlled window blinds 24, a controlled lighting or lamp unit 25 etc, individual or wired or wireless network of personal computing (PC) and laptop/mobile devices 30a, . . . , 30c that serve as file sources, control points and hosts for various other client endpoints, one or more television display devices 32 including associated digital media devices 35, set top boxes (STB) 35a, or digital media adapters (DMA) 35b, one or more VoIP phone devices (e.g. SIP phones) 40, or other devices (not shown) that convert IP interfaces to PSTN FXO and FXS interfaces.

As noted earlier in connection with FIG. 2, the gateway device 10 may provide an interface to a digital media device, such as digital media adaptor (DMA) 35b and audio-video system 530 or television (TV) 32, which enables bidirectional wireline or wireless communication. This interface supports several functions for multiple services including, but not limited to: media (e.g., video and music) by enabling the transfer of media (e.g., video and music) to the TV; voice services, by providing for Called Line ID and for voice mail control; and provide Home Automation Services including status and control of networked home automation devices. The DMA element 35b converts audio and/or video to a format suitable for an audio type presentation, a video type presentation, or a combination of audio and video type presentation on a television display or audio-video system. In addition, the Digital Media Adapter 35b may be capable of receiving context-sensitive commands from a remote control device (shown in FIG. 2) and forwarding those commands to the gateway device 10. This enables the use of menus on the TV 32 for controlling application services and various features functions thereof, as offered by the gateway device 10. For example, the digital media adaptor 35b and television 32 combination is able to provide the following features including, but not limited to: display of media; media control functions, when enabled (FF, REW, STOP, PAUSE, etc); display of Calling Line Identification (CLID); control of voicemail; picture viewing; control of home automation; and user functions for the gateway device 10.

A Set Top Box 35*a*, as shown in FIG. 5, may handle media format conversion (for example NTSC to ATSC television RF signals), digital decryption and other DRM (digital rights management) functions, and Video On Demand Purchases, etc. As described above in connection with FIG. 2, Set Top Box 35*a* may also be configured to operate as a digital media device (e.g., digital media device 35 as shown in FIGS. 2, 3, and 5 and as described above in connection with FIGS. 2 and 4). The Set Top Box/TV combination may thus enable, by way of example: Media format conversion (for example NTSC to ATSC); decryption; other DRM functions (such as expiry of leases), prohibition of copying to digital outputs, function restriction, etc.; Video On Demand Purchases; and media control functions (e.g., FF, REW, STOP, PAUSE, etc.). Alternatively, Set Top Box 35*a* may serve as a media source (e.g., media source 510 shown in FIG. 2) communicatively coupled to digital media device, which may provide audio and/or video type presentations to digital media device 35 and audio-video system 530 or television display 32.

Whether provided by the DMA interface 35*b* and the TV 32 (or audio-video system 530 shown in FIG. 2), by the set-top-box 35*a* and the TV 32, or by digital media device 35 and TV 32, the communications to and from the TV provide a user interface for interaction with the gateway device 10. The programming of the gateway device and/or the digital media device supports, among other things, a graphical user interface (GUI) via the TV, sometimes referred to as the "ten-foot" interface.

With respect to PCs interfacing with the gateway device 10, PCs may serve as, among other things, file sources, control points and hosts for various software clients. Thus, the PC programming may work in conjunction with the ASL and ASE programming of the gateway device. Together, the PC programming and the ASL and ASE programming provide a more comprehensive and robust user experience. The gateway device 10 may further provide a bidirectional wireline or wireless interface 35*c* to a PC device 306 for supporting the transfer of media (e.g., video and music) to the computer for storage and viewing; for supporting voice services, e.g., by providing for calls from SIP (session initiation protocol) soft clients; for file sharing, file back-up and home storage and home automation control functions. The access point 62 offers wireless data communications with a PC 30*c*. The gateway device interface through any PC may provide for the bidirectional moving of files, and status and control for the endpoint devices, including for example, status and control of networked home automation devices. In addition, using the PC interface, users may, for example, share files on the gateway devices, back-up or transfer files to the gateway devices or other storage; access personal page for notifications, RSS, shared photos, voicemail, etc. In addition to the IM (instant messaging) and SIP capabilities of the gateway device, as described more below, PCs may also serve as a host for IM and SIP soft phone clients and other client devices. The client-server interaction of the PC with the application service logic of the gateway device 10 offers an alternative GUI for at least some of the services. The PC based GUI is sometimes referred to as the "two-foot" interface.

Although not shown in FIG. 5, other digital endpoint devices for which connectivity may be established with the gateway device 10 include, but are not limited to: personal music or media players (e.g., device 526 illustrated in FIG. 2), hi-fi audio equipment with media streaming capability (e.g., audio-video system 530 illustrated in FIG. 2), game stations (e.g., media source 510 shown in FIG. 2), Internet radio devices (e.g., media source 510 shown in FIG. 2), WiFi phones, WiFi or other wirelessly enabled digital cameras (e.g., digital camera 522 shown in FIG. 2), facsimile machines, electronic picture frames, health monitors (sensor and monitoring devices), etc.

As described in greater detail herein, the gateway device 10 includes both a hardware and software infrastructure that enables a bridging of the WAN and LAN networks, e.g. a proxy function, such that control of any digital endpoint device at the premises from the same or remote location is possible via the gateway device 10 using, optionally, a secure peer and presence type messaging infrastructure or other communications protocols, e.g. HTTPS. For example, via any presence and networking protocol capable device (i.e., IM-capable device) or client 80*a*, 80*b* respectively connected with an Instant Messaging (IM) or XMPP (Extensible Messaging and Presence Protocol) network messaging infrastructure, e.g. IM networks 99*a*, 99*b* such as provided by Yahoo, Microsoft (MSN), Skype, America Online, ICQ, and the like, shown for purposes of illustration in FIG. 5, a user may access any type of functionality at a subordinate digital endpoint device (e.g., digital media device 35 and television 32, etc.) at the premises via the gateway device 10 and service management center 50 by simple use of peer and presence messaging protocols. In one exemplary embodiment, a peer and presence communications protocol may be used such XMPP (Extensible Messaging and Presence Protocol). Particularly, streaming XML protocols and technologies enable any two entities on the Internet to exchange messages, presence, and other structured information in close to real time. The Internet Engineering Task Force (IETF) has formalized the core XML streaming protocols as an approved instant messaging and presence technology under the name of XMPP, the XMPP specifications of which are incorporated by reference herein as IETF RFC 3920 and RFC 3921. Thus, the gateway device is provided with functionality for enabling a user to remotely tap into and initiate functionality of a digital endpoint device or application at the premises via the IM-based messaging framework. In addition, the gateway device 10 and network connectivity to the novel service management center 50, provides, in a preferred embodiment, a secure peer and presence messaging framework, enabling real-time communications among peers via other gateway devices 10.sub.1 . . . 10.sub.n. For instance, the device 10 provides the ability to construct communication paths between peers with formal communications exchanges available between, for example, one gateway device 10.sub.1 at a first premises and a second gateway device 10.sub.n located at the remote premises. Thus, such an infrastructure provides for content addressing, enabling peers through remote gateway devices 10.sub.1 . . . 10.sub.n to supply and request content such as files, media content or other resources of interest to a community of interest.

As noted above, the novel system architecture allocates the logical functionality of the ASD Platform (FIG. 1) between the gateway device 10 and the service management center 50 within an environment that enables communication and feedback at the AS Layer (FIG. 1) between the gateway device 10 and service management center 50. Thus, the gateway device 10, when operable with the service management center 50, makes possible the management of services for the digital home and facilitates the easy addition of new services or modification of existing services. Such services may include, for example, facility management (home automation), media content downloading and Digital Rights Management (DRM), device updates, data backups, file sharing, media downloading and transmission, etc., without the intermediary of a plurality of external service providers who may typically provide these individual services for every digital endpoint device in the home or premises. The programming for these services resides in the Application Service Provider Managed Applications and Platform of the UNA-DA (FIG. 4). That is, as earlier shown, the gateway device 10 is integrated with hardware and software modules and respective interfaces that handle all aspects of home automation and digital endpoint service and management for the home in a manner without having to rely on external service providers and, in a manner that is essentially seamless to the user. This, advantageously is provided by the service management center 50 which is able to access regions of the gateway device 10 that are not accessible to the user, e.g. for controlling the transport and storing of digital content and downloading and enabling service applications and upgrades and providing largely invisible support for many tasks performed by users.

For example, with the robust capabilities of the Application Service Provider Managed Applications and Platform (FIG. 4), the gateway device 10 is capable of handling all aspects of the digital home communications, e.g. IP, voice, VoIP, phone connectivity. In this example, the service logic located and stored at the gateway device 10 may provide soft-switch functionality for implementing call-processing features at the premises (rather than the network) for voice communications, and enabling management of other service features to be described. With the provision of central office type call services and other service features provided at the gateway devices 10.sub.1 . . . 10.sub.n, a distributed soft-switch architecture is built. The ASM logical functionality of the service management center 50, in cooperation with the ASE logical functionality of the gateway device, may, among other things, provide, manage and regulate, for example, service subscription/registration, authentication/verification, key management, and billing aspects of service provision, etc. With all of the service logic and intelligence residing at the gateway device, a service provider can offer customers a broad spectrum of services including, but not limited to: media services, voice services, e.g. VoIP, automated file backup services, file sharing, digital photo management and sharing, gaming, parental controls, home networking, and other features and functions within the home or premises (e.g. home monitoring and control). Users can access their content and many of the solution's features remotely. Moreover, software updates for the in-home devices that require updating are handled in an automated fashion by the system infrastructure. The service management center infrastructure additionally provides a web interface for third-party service providers to round out the service solutions provided at the gateway device for the premises. For example, a third-party service provider other than the managed service provider associated with the service management center may be allowed access through the infrastructure to particular endpoint devices to provide additional services such trouble shooting, repair and update services.

Gateway Device Software and Hardware Architecture

Figure 6A:
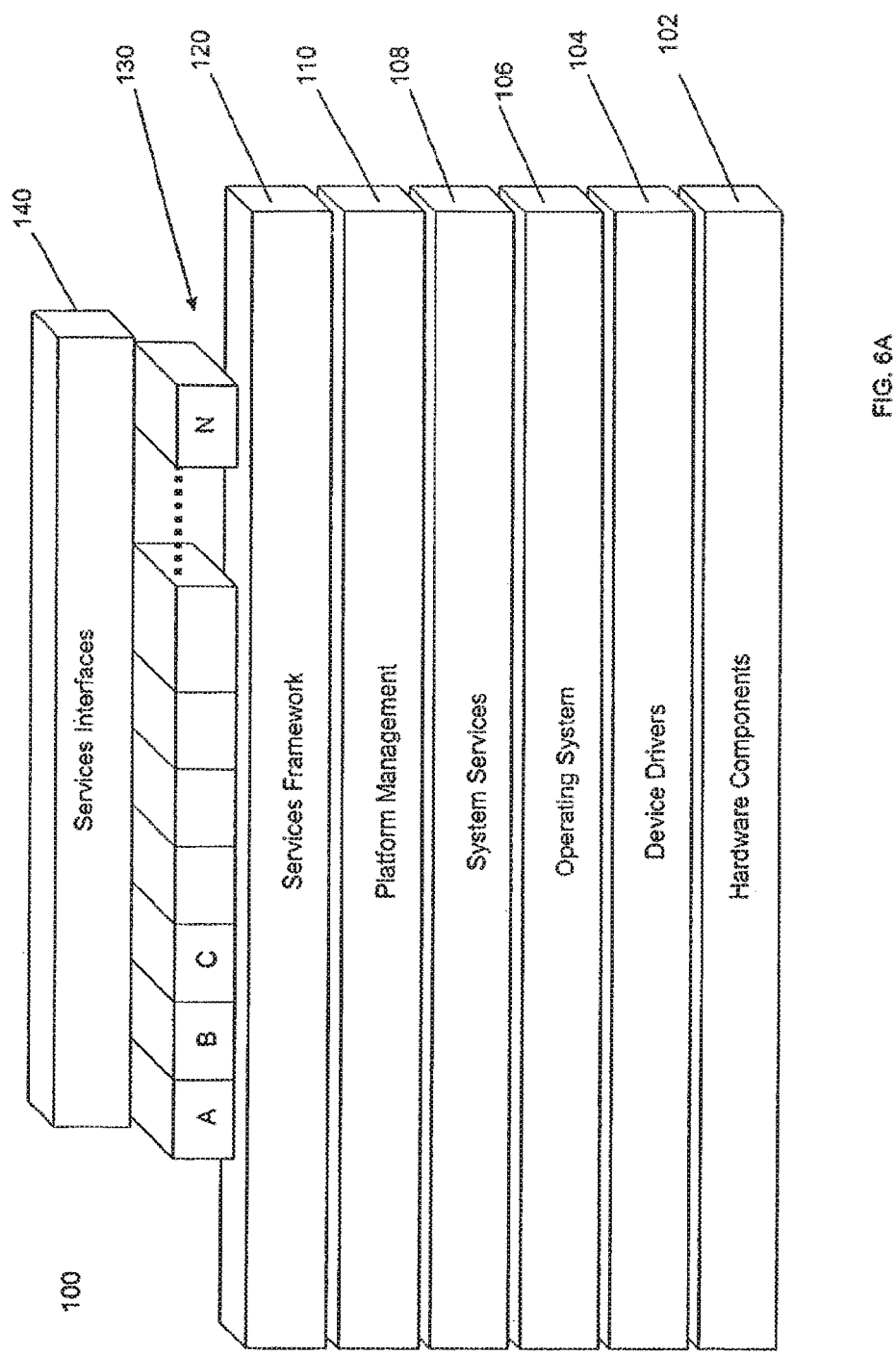
Figure 6B:
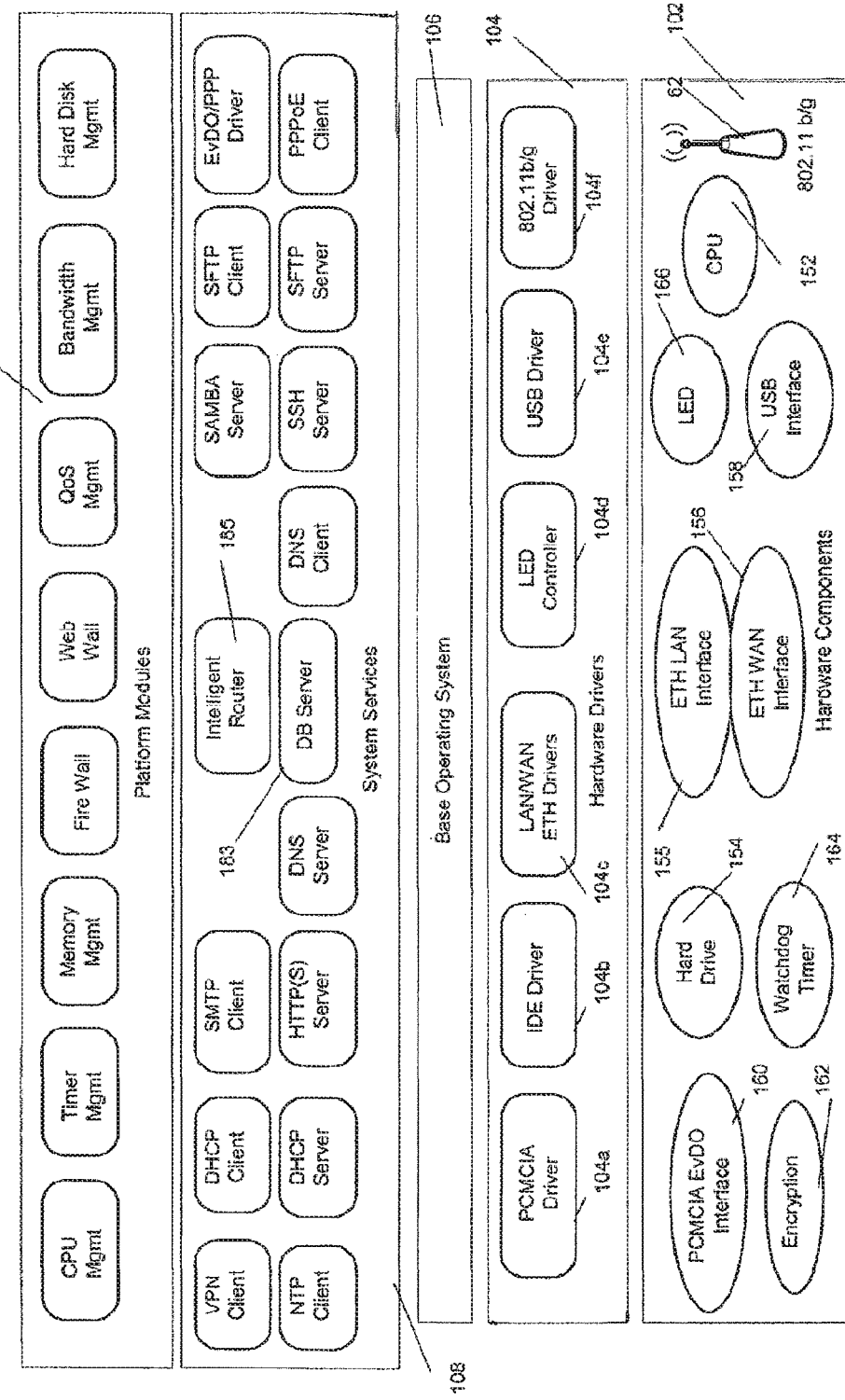
Figure 6D:
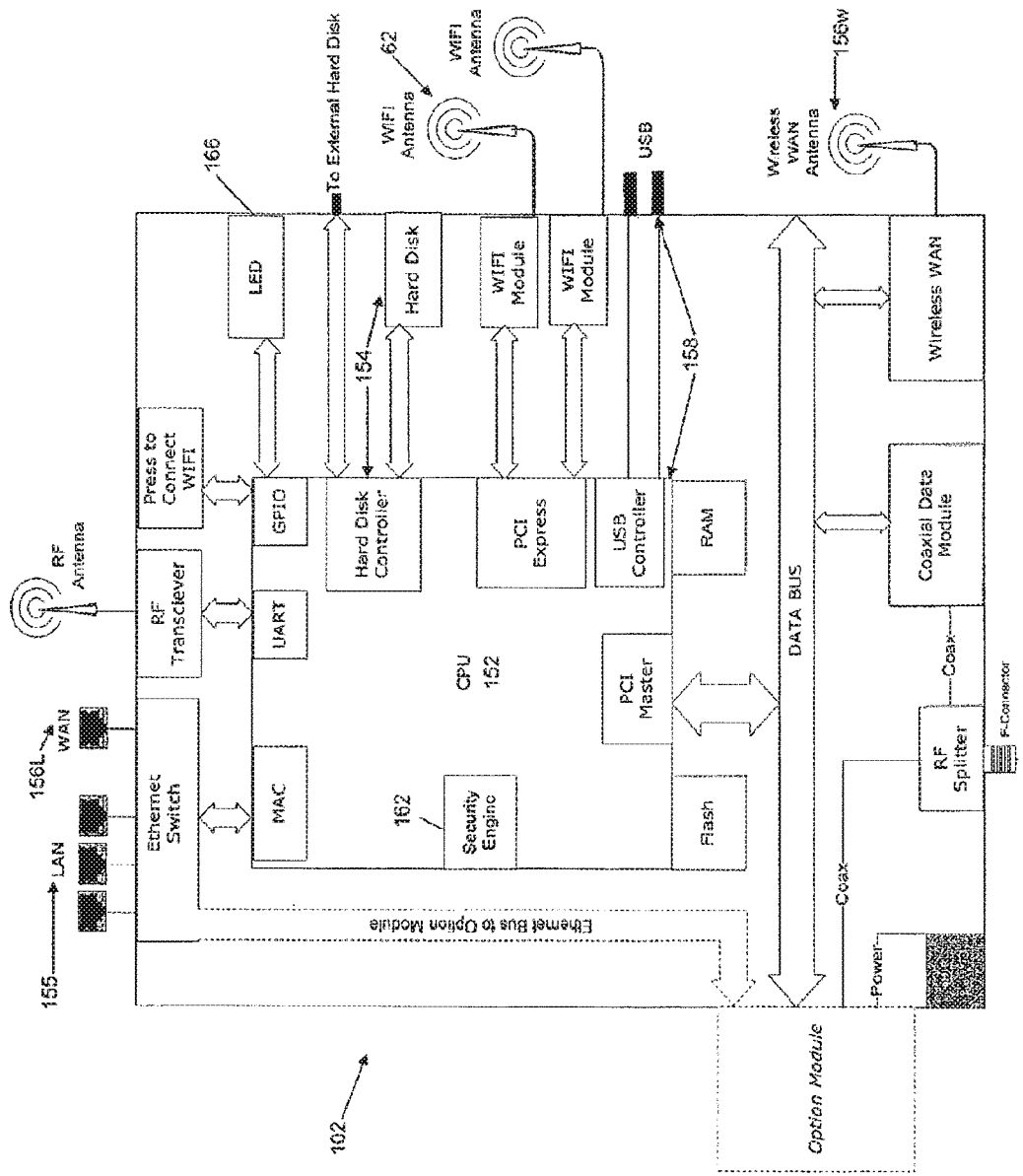

The composition of the premises gateway device 10, earlier described with reference to FIG. 4, is now described in greater detail with reference to FIGS. 6A-6D. As shown in FIG. 6A, the gateway device 10 utilizes a layered architecture 100, which enables the encapsulation of similar functionality and the minimization of dependencies between functions in different layers. FIGS. 6B and 6C depict exemplary functionality (hardware and logical) resident in, or corresponding to, each of the layers shown in FIG. 6A. The layers include a hardware layer 102, and device driver software 104 for allowing the processor to operate other hardware elements of the gateway device 10. FIG. 6D is a functional block diagram illustrating interconnection of exemplary elements of the hardware layer 102. The logical elements of the NI Layer residing on the gateway device 10 (FIG. 5) are found in the Hardware Drivers 104 which govern the operation of the Hardware Components 102. The processor runs an operating system shown at layer 106, which plays a role in each of the NI, NF, AS and Platform Management Layers (FIG. 1). The layered architecture 100 also includes software for systems services 108 and for the platform management layer shown at 110 in this drawing. Logical elements represented by the NF Layer depicted in FIG. 1 are comprised of elements from the system services 108 of FIG. 5. In a similar fashion, the Platform Management Layer depicted in FIG. 1 is implemented in the exemplary architecture of FIGS. 6A-6D by the platform modules 109 and the platform management layer 110.

Particular logical elements comprising the ASL and ASE functionalities of the AS Layer represented in FIG. 1, and that reside on the gateway device 10 (predominately in the Application Service Provider Managed Applications and Platform of the UNA-DA shown in FIG. 4) are depicted in FIG. 6C, and comprise logical elements from each of services framework 120 and application services 130. The layered architecture in FIG. 6C facilitates reuse or sharing of logic across the layers to provide a managed service framework 120. The service management functionality provided by the framework 120 enables deployment of new services as pluggable modules comprising computer readable instructions, data structures, program modules, objects, and other configuration data, in a plug and play fashion. The layered service architecture 100 additionally provides the gateway device 10 with intra-process communication and inter-process communication amongst the many services and modules in the service framework layer 120 that enables the provisioning, management and execution of many applications and services 130, depicted e.g. services A, B . . . N at the gateway device 10. Additionally provided are the application service interfaces 140 that enable communications from user endpoint devices with service environments. In that regard, the interfaces 140 enable the application service logic 130 to act as an appropriate server with respect to client device application or service functionality of the endpoint devices (e.g., digital media device 35 and television display 32 shown in FIG. 2, etc.). The application service interfaces 140 also enable corresponding interfaces for the application services with aspects of service environments implemented outside the user premises. In that regard, the interfaces 140 enable the application service logic 130 to act as an appropriate client, for extending the application or service related communications to a server accessed via the wide area network 99, such as a server of the service management center 50. For example, the gateway device may appear as a SIP server to a SIP client in an end point device, e.g. for a VoIP telephone service; but the gateway device will appear as a SIP client with respect to some related functions provided by a server (such as a SIP directory server) provided by the service management center 50.

FIG. 6A thus depicts a high level service framework upon which are built services, e.g. downloaded via the service management center network 50 and wide area network 99 as packages that are developed and offered by a service entity for customers. These services may be offered as a part of a default service package provisioned and configured at the gateway device 10, or provisioned and configured subject to user subscription and may be added at any time as plug-in service modules in cooperation with the service management center 50. It is understood however, that while the gateway device 10 includes much of the intelligence or service logic for providing various services, it is also possible that for some services, some or all of service logic may reside in the service management center network and/or with a third party provider.

As shown in more detail in FIGS. 6B and 6D, the base support layer 102 comprises hardware components including a processor device 152, e.g. a system on chip central processing unit ("CPU") that includes processing elements, digital signal processor resources and memory. The CPU 152 is also coupled to a random access memory ("RAM") and additionally, non-volatile hard drive/disk magnetic and/or optical disk memory storage 154. Generally, the above-identified computer readable media provide non-volatile storage of computer readable instructions, data structures, program modules, objects, service configuration data and other data for use by the gateway device. The non-volatile hard drive/disk magnetic and/or optical disk memory storage 154 may be partitioned into a network side which is the repository for storing all of the service logic and data associated with executing services subscribed to by the user, and, is invisible to the user, and, a user side for storing user generated content and applications in which the user has visibility. Although not shown, the CPU 152 may be coupled to a microcontroller for controlling a display device.

Additional hardware components include one or more Ethernet LAN and WAN interface cards 155, 156 (e.g. 802.11, T1, T3, 56 b, X.25, DSL or xDSL) which may include broadband connections (e.g. ISDN, Frame Relay, ATM, Gigabit Ethernet, Ethernet over SONET, etc.), wireless connections, or some combination of any or all of the above. The card 155 referred to as the LAN interface card provides data communication connectivity within the user premises, essentially, for communication via a user premises network 60 with any endpoint devices operating within the premises. The card 156 referred to as the WAN interface card provides data communication connectivity for the gateway device 10 and endpoint devices communicating through the device 10, with the wide area IP network 99. For additional or alternative customer premises communications, the hardware components 102 may also include one or more USB interfaces 158; and for additional or alternative communications with the wide area network, the hardware components may also include the PCMCIA EvDO interface card 160.

A data encryption/decryption unit 162 is additionally provided as part of the architecture for providing data security features. A watchdog timer element or like timer reset element 164 is provided as is one or more LED devices 166 for indicating status and other usable information to users of the gateway device 10.

As mentioned above, the gateway device provides an in-premises footprint enabling the service connectivity and local management to client(s). The implementation of functions and the related control such as a router (with quality of service (QoS)), firewall, VoIP gateway, voice services and voice mail may be embodied and performed within the CPU 152.

The discussion of the gateway hardware layer above and the illustration thereof in the drawings provides a high-level functional disclosure of an example of the hardware that may be used in the gateway device. Those skilled in the art will recognize that the gateway device may utilize other hardware platforms or configurations.

Continuing, as shown in FIG. 6B, the device driver layer 104 comprises a multitude of driver interfaces including but not limited to: a PCMCIA driver 104a, for enabling low level communication between the gateway CPU 152 and the PCMCIA network interface card wireless interface, an IDE driver 104b for enabling low level communication between the gateway CPU 152 and the local mass memory storage element, and LAN/WAN drivers 104c for enabling low level communication between the gateway CPU 152 and the respective network interface cards 155 and 156. The exemplary driver layer also includes an LED driver/controller 104d for driving LED(s) 166, a USB driver 104e allowing CPU 152 to communicate via USB interface 158, and an 802.11b/g (or n) wireless network driver 104f for allowing the CPU 152 to communicate via the access point 62. The drivers provide the logical connectivity between the low level hardware devices 102 and the operating system 106 which controls the execution of computer programs and provides scheduling, input-output control, file and data management, memory management, and communication control and related services for the gateway device. With respect to the operating system 106, the gateway computing may support any embedded operating system, any real-time operating system, any open source operating system, any proprietary operating system, or even any operating systems for mobile computing devices as long as the operational needs of the client discussed herein below can be met. Exemplary operating systems that may be employed include Windows.®, Macintosh.degree., Linux or UNIX or even an embedded Linux operating system. For instance, the gateway device 10 may be advantageously provided with an embedded operating system 106 that provides operating system functions such as multiple threads, first-in first-out or round robin scheduling, semaphores, mutexes, condition variables, message queues, etc.

Built upon the system operating system 106 is a system services support layer 108 providing both client-like and server-like functions that enable a wide range of functionality for the types of services capable of being managed by the gateway device 10. For instance, there is provided a Dynamic Host Configuration Protocol (DHCP) client and server software modules. The DHCP client particularly requests via a UDP/IP (User Datagram Protocol/Internet Protocol (e.g. Ipv4, Ipv6, etc.) configured connection information such as the IP address that the gateway device 10 has been dynamically assigned by a DHCP service (not shown), and/or any the subnet mask information, the gateway device should be using. The DHCP server dynamically assigns or allocates network IP addresses to subordinate client endpoints on a leased, e.g. timed basis. A Virtual Private Network (VPN) client may communicate via a proxy server in the service control network 50, according to a VPN protocol or some other tunneling or encapsulation protocol. An SMPT client handles incoming/outgoing email over TCP, in accordance with the Simple Mail Transfer protocol. A Network Time Protocol (NTP) (RFC 1305) generates and correlates timestamps for network events and generally provides time synchronization and distribution for the Internet. A Domain Name Server (DNS) client and server combination are used by the IP stack to resolve fully-qualified host or symbolic names, i.e. mapping host names to IP addresses.

An HTTP(S) server handles secure Hypertext Transfer Protocol (HTTP) (Secure Sockets Layer) communications and provides a set of rules for exchanges between a browser client and a server over TCP. It provides for the transfer of information such as hypertext and hypermedia, and for the recognition of file types. HTTP provides stateless transactions between the client and server.

A Secure File Transfer Protocol (SFTP) client and server combination govern the ability for file transfer over TCP. A SAMBA server is an open source program providing Common Internet Files Services (CIFS) including, but not limited to file and print services, authentication and authorization, name resolution, and service announcement (browsing). An EvDO/PPP driver includes a Point-to-Point Protocol (PPP) daemon configuration for wireless broadband services. A PPPoE (Point-to-Point Protocol over Ethernet) client combines the Point-to-Point Protocol (PPP), commonly used in dialup connections, with the Ethernet protocol; and it supports and provides authentication and management of multiple broadband subscribers in a local area network without any special support required from either the telephone company or an Internet service provider (ISP). The gateway device 10 is thus adapted for connecting multiple computer users on an Ethernet local area network to a remote site through the gateway and can be used to enable all users of an office or home to share a common Digital Subscriber Line (DSL), cable modem, or wireless connection to the Internet. A Secure Shell or SSH server implemented with HTTP protocol provides network protocol functionality adapted for establishing a secure channel between a local and a remote computer and encrypts traffic between secure devices by using public-key cryptography to authenticate the remote computer and (optionally) to allow the remote computer to authenticate the user.

Additionally provided as part of the system services layer 108 is intelligent routing capability provided by an intelligent router device 185 that provides Quality of Service (QoS, guaranteed bandwidth) intelligent routing services, for example, by enforcing routing protocol rules and supporting unlimited multiple input sources and unlimited multiple destinations and, particularly, for routing communications to networked digital endpoint devices subordinate to the gateway. A central database server 183 handles all of the database aspects of the system. For example, the database server 183 maintains and updates registries and status of connected digital endpoint devices, maintains and updates service configuration data, services specific data (e.g. indexes of backed-up files, other service specific indexes, metadata related to media services, etc.) and firmware configurations for the devices. The database server 183 may also store billing and transaction detail records and performance diagnostics. The database server logic 183 also satisfies all other database storage needs as will be described in greater detail herein.

Referring back to FIGS. 6A and 6B, built on top of the system services layer 108 is the platform module layer 109. The platform module layer 109 provides a software framework for operating system and communications level platform functionality such as CPU management; Timer management; memory management functions; a firewall; a web wall for providing seamless WWW access over visual displays via access technologies enumerated herein, e.g. HTTP, SMS (Short Messaging Service) and WAP (Wireless Access Protocol); QoS management features, bandwidth management features, and, hard disk drive management features. The layered architecture 100 further provides a platform management layer 110 as shown in FIG. 6C, which together with the platform modules 109 implement the platform management layer/logic discussed earlier (with regard to FIG. 1).

The features/functions in the layer 110 include a platform manager module which will implement unique rules based notification services. On operational failure, for example, when one of the components or services fails, the platform manager would detect this failure and take appropriate action such as implement a sequence of rules to provide notification to a user. A scheduler module manages scheduled device maintenance, managing scheduled services, e.g. back-up services, etc. The layer 110 also includes a diagnostics module and a firmware upgrades management module for managing firmware upgrades. A resource management module manages system resources and digital contention amongst the various resources, e.g. CPU/Bandwidth utilization, etc. A display management module and a logger management module store and track gateway log-in activity of users and applications, e.g. voice call logs, at the user premises. The platform management layer 110 in concert with resource and service management components enforces the separation of network side managed service control and user side delegations depending upon service subscriptions and configurations. For example, the platform and resource management encompass rules and guidelines provided according to subscribed services that act to enforce, manage and control input/output operations, and use of hard drives space, etc. A demarcation point, logically depicted as the Application Service Provider Demarcation in FIG. 4, is thus defined that provides a hard line between what is owned by the customer and what is owned by the service provider.

The logical platform management layer 110 allows for inter-layer allocation of local resources. This function guarantees access between the application service/management logic implemented at the higher layers in the gateway device 10 and the applications service management function in the service management center 50, by assuring that the local user premises hardware and software modules are functioning at a required state (CPU and memory usage, bandwidth usage, QoS settings, etc.). The platform manager is also responsible for implementing that part of the managed application services to be performed by the gateway device. In that regard, the platform manager secures and manages the overall hardware platform, given that in this scenario, the network function layer and the application service layer reside on one hardware platform. This secure hardware platform provides a robust and secure operating environment for the application services layer. So, to establish a secure and robust hardware operating environment, the platform management layer must interface with all the layers above it and allow for bi-directional management information flow among all of the functions.

Referring back to FIGS. 6A and 6C, built on top of the platform management layer 110 is the Services Framework 120, which provides a library of application support service processes that facilitate data collection and data distribution to and from the multimedia endpoint devices. The application support service processes include, but are not limited to: an authentication manager for use in authenticating devices connected to the gateway device; a billing manager for collecting and formatting service records and service usage by endpoint devices, e.g. calls, back-up services etc.; a fault manager for detecting and managing determined system and/or service faults that are monitored and used for performance monitoring and diagnostics; a database manager; a control channel interface via which the gateway initiates secure communications with the operations support infrastructure; a configuration manager for tracking and maintaining device configuration; a user manager; a service manager for managing service configuration and firmware versions for subscribed services provided at the gateway device; and a statistics manager for collecting and formatting features associated with the gateway device. Statistics may relate to use of one or more services and associated time-stamped events that are tracked.

Built on top of the Services Framework layer 120 is the Application Services layer 130 providing library of user application services and application support threads including, but not limited to: file sharing functionality; backup services functionality; home storage functionality; network device management functionality; photo editing functionality; home automation functionality; media services functionality; call processing functionality; voice mail and interactive voice response functionality; presence and networking functionality; parental control functionality; and intelligent ads management functionality. The multi-services applications gateway 10 further provides application service interfaces 140 that are used to enable a variety of user applications and communications modalities.

For instance, the SIP Interface 141 is an interface to the generic transactional model defined by the Session Initiation Protocol (SIP) that provides a standard for initiating, modifying or terminating interactive user sessions that involve one or more multimedia elements that can include voice, video, instant messaging, online games, etc., by providing access to dialog functionality from the transaction interface. For instance a SIP signaling interface enables connection to a SIP network that is served by a SIP directory server via a Session Border Controller element in the service management center 50 (FIG. 5).

The Web Interface 142 enables HTTP interactions (requests and responses) between two applications. The Web services interface 149 provides the access interface and manages authentication as multi-services gateway devices access the service management center 50 (FIG. 5) via web services. The IM Interface 144 is a client that enables the multi-services gateway device 10 to connect to one or more specific IM network(s). As further shown in FIG. 6C, the UpNp (Universal Plug and Play) interface enables connectivity to other stand-alone devices and PCs from many different vendors.

The XMPP interface 145 is provided to implement the protocol for streaming (XML) elements via the gateway device 10, in order to exchange messages and presence information in close to real time, e.g. between two gateway devices. The core features of XMPP provide the building blocks for many types of near-real-time applications, which may be layered as application services on top of the base TCP/IP transport protocol layers by sending application-specific data qualified by particular XML namespaces. In the example, the XMPP interface 145 provides the basic functionality expected of an instant messaging (IM) and presence application that enable users to perform the following functions including, but not limited to: 1) Exchange messages with other users; 2) Exchange presence information with other devices; 3) Manage subscriptions to and from other users; 4) Manage items in a contact list (in XMPP this is called a "roster"); and 5) Block communications to or from specific other users by assigning and enforcing privileges to communicate and send or share content amongst users (buddies) and other devices.

As noted, FIG. 6D provides a functional block diagram of exemplary elements of the hardware layer 102. For example, a system on a chip provides the CPU 152 and associated system components. The CPU 152 is also coupled to a random access memory ("RAM") and flash memory. The system on a chip also includes a hard drive controller for controlling a hard disk drive, and together the controller and drive form the hard disk example of the storage 154. An Ethernet switch and associated LAN port(s) provide the Ethernet LAN interface 155; and the Ethernet switch and associated WAN port provide a landline implementation of the WAN interface 156L, for connection to a broadband modem or the like implementing the NSP-TA. The WAN interface may also be wireless, as implemented at 156w for example by a wireless WAN module and associated antenna. An example of such an interface would be the EvDO interface discussed earlier. If the gateway device uses the wireless WAN interface 156w, there would be no separate NSP-TA.

In the example of FIG. 6D, a USB controller in the system on a chip and one or more associated USB ports provide the USB interface 158. The USB interface 158 may provide an alternate in-premises data communication link instead of or in addition to the wired or wireless Ethernet LAN communications. The system on a chip includes a security engine, which performs the functions of the data encryption/decryption unit 162.

The hardware layer 102 may also include an option module. The UNA-DA hardware components at layer 102 have multiple interfaces for connection to such an option module. These interfaces, by way of example, could be a data bus (e.g. PCI, etc), network interface (e.g. Ethernet (RJ45), MoCA/HPNA (Coax)) and Power feeds. The option module allows additional functionality to be added to the base UNA-DA functionality of the gateway device. For example, this additional functionality could be everything from support for a variety of extra Wide Area Network Interfaces (e.g. xDSL, DOCSIS, Fiber (PON), Cellular Packet, WIMAX, etc.), Media Processing (e.g. Cable TV termination, Digital Video Recording, Satellite TV Termination, etc), to Voice Processing (FXS, FXO, Speech Detection, Voice to Text, etc). The option module may have its own standalone CPU, Memory, I/O, Storage, or provide additional functionality by its use of the CPU, Memory, I/O, and storage facilities off of the main hardware board. The option module may or may not be managed directly by the Platform Management of the UNA-DA.

Gateway Processing

For the in-home services, the multi-services gateway device 10 connects the various service delivery elements together for enabling the user to experience a connected digital home, where information from one source (for example, voicemail) can be viewed and acted on at another endpoint (for example, the TV 32). Various application services available via gateway device 10 may be provided to endpoint devices (e.g., TV 32) via digital media device 35. The multi-services gateway device 10 thus hosts the various in-home device interfaces, and facilitates the moving of information from one point to another. Digital media device 35 may collaboratively operate gateway device 10 to provide services to endpoint devices communicatively coupled to digital media device 35.

Some of the in-home endpoint device processing duties performed by the gateway device 10 include, but are not limited to: 1) detecting new devices and provide IP addresses dynamically or statically; 2) functioning as a (Network Address Translator) NAT, Router and Firewall; 3) providing a centralized disk storage in the home; 4) obtaining configuration files from the service management center and configuring all in-home devices; 5) acting as a Registrar for SIP-based devices; 6) receiving calls from and delivering calls to voice devices; providing voicemail services; 7) decrypting and securely streaming media having digital rights management (DRM) encoding; 8) distributing media to an appropriate in-home device; 9) compressing and encrypting files for network back-up; 10) backing-up files to the network directly from gateway device; 11) handling home automation schedules and changes in status; 12) providing in-home personal web-based portals for each user; 13) providing Parental Control Services (e.g. URL filtering, etc.); 14) creating and transmitting billing records of in-home devices including, recording and uploading multi-service billing event records; 15) distributing a PC client to PCs in the home, used in support of the various services such as monitoring events or diagnostic agents; 16) storing and presenting games that users and buddies can play; 17) delivering context-sensitive advertising to the endpoint device; and, 18) delivering notifications to the endpoint device; and, 19) enabling remote access through the web, IM client, etc. Other duties the gateway device 10 may perform include: service maintenance features such as setting and reporting of alarms and statistics for aggregation; perform accessibility testing; notify a registration server (and Location server) of the ports it is "listening" on; utilize IM or like peer and presence communications protocol information for call processing and file sharing services; receive provisioning information via the registration server; utilize a SIP directory server to make/receive calls via the SBC network element to/from the PSTN and other gateway device devices; and download DRM and non-DRM based content and facilitating the DRM key exchanges with media endpoints.

Gateway to Gateway Device Communications

As mentioned earlier, the gateway devices and service management center support a communication capability between the appliances. This feature, for example, may be utilized for enabling secure peer-to-peer sharing of data between or among the gateway appliances.

Additional aspects of the peering capabilities enabled by the gateway device-service management architecture include the ability to store a roster or contact list of distant gateways on either the gateway 10 or within the service management center 50 and utilizing these addresses to maintain the presence and routing information of selected other gateways. This roster information is used to establish and manage access and message routing, via XMPP messaging, to gateways, to locate and address other gateways, and set up peering relationships between the gateways.

A gateway may also expose other details about resources or endpoints within the home to other gateways by communicating resource information along with presence information. As an example, a gateway may send presence information to selected "buddies" via the signaling channel and also include information about the resources available to the distant buddy. Examples of resources include digital picture frames that the distant gateway user may direct photos to, web cams, or other resources, enabling direct interaction between an end user connected to one gateway, or in automated scenarios, the gateway itself, and a distant device connected to the local area network of another gateway.

When a user interacts with the resource sharing functions of their gateway 10, the user may select a specific gateway 10.sub.1 from their roster, represented as a "buddy" list. When the user selects a "buddy", additional resource details are displayed to the user, providing information about any resources that the end user may utilize via that selected peer gateway device 10.sub.1.

The XMPP messaging protocol, combined with the roster and XMPP addressing mechanisms may be utilized for either end user interactions or automated interactions between gateways. Automated use of the peering capabilities include directing utility data for usage and network management information to designated collectors within peering groups and then having the designated collector forward the combined information to the service management center. This distributes the collection processing to the gateways and decreases the overall processing and bandwidth utilization in the service management center. Of course, the XMPP protocol is discussed here merely by way of example, and those skilled in the art will recognize that the gateway to gateway device communications may use other protocols.

Various media device operations as well as the gateway device 10 and its interactions with the digital media device 35, various other endpoint devices, and with the service management center 50 have been described with reference to diagrams of methods, apparatus (systems) and computer program products. It will be understood that elements and functions illustrated in the diagrams, can be implemented by computer program instructions running on one or more appropriately configured hardware platforms, e.g. to operate as a digital media device 35, a gateway device 10 or as one or more elements of the service management center 50. Hence, operations described above may be carried out by execution of software, firmware, or microcode operating on a computer other programmable device of any type. Additionally, code for implementing such operations may comprise computer instruction in any form (e.g. source code, object code, interpreted code, etc.) stored in or carried by any computer or machine readable medium.

Graphical User Interface (GUI)

Figure 8A:
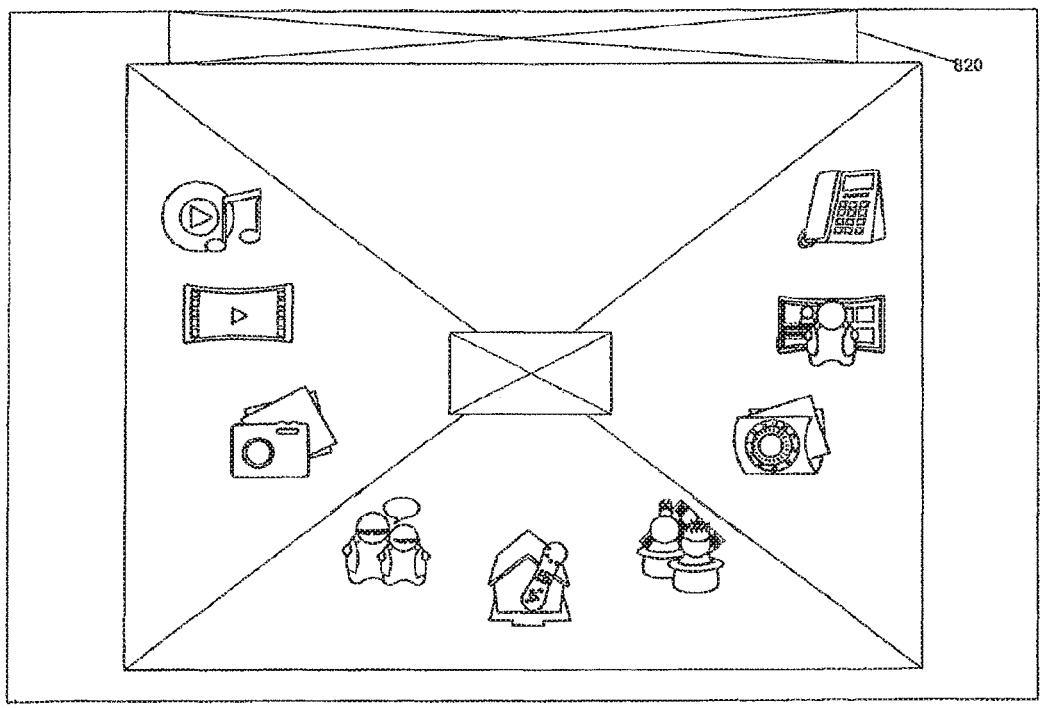
FIG. 8A illustrates a graphical user interface depicting icons in a substantially curved arrangement.

FIG. 8A illustrates an exemplary graphical user interface 820, which may provide service and media selections for a user. These selectable services and media options may be managed by gateway device 10, based at least in part on applications, services, and/or media sources that a user may have subscribed to. Additionally, some selections may be based in part on media sources (e.g., media source 510), storage devices (e.g., devices 522, 524, or 526, etc.) communicatively connected to the digital media device 35. Gateway device 10, or a combination of gateway device 10 and digital media device 35, may provide the exemplary graphical user interface 820 for presentation to a user on television display 32.

As illustrated in FIG. 8A, interface 820 may be presented by digital media device 35 for display on television display 32 to users. As shown, interface 820 may have an arrangement of graphical icons 822 in a pattern. The pattern, which is substantially curved as shown in FIG. 8A, may have first end 824 and second end 826, with first end 824 and second end 826 each defined by a display edge of the television display. Each graphical icon 822 may represent a media application, service application, or media and service application. Examples of applications represented by icons include music, video, pictures, home automation, games, phone and messaging, parental control, or any other suitable applications. Some graphical icons 822 may represent media applications that may be provided by a media source such as media source 510, from storage devices 520 (e.g., digital camera 522, flash memory 524, PMP device 526, etc.), or from other devices via interfaces 650, 660, 670, 680 of media device 35. Some graphical icons 822 may represent media applications, service applications, or media and service applications provided via gateway device 10.

Using a remote control or other control device, a user may highlight one of the graphical icons 822 located substantially a center 828 (e.g., the apex of the curve) of the pattern to enable selection of the one graphical icon. Digital media device 35 may receive a selection from a remote (e.g., remote 550) to move the arrangement graphical icons in a first direction or a second direction (e.g., in the curved pattern shown in FIG. 8A, the graphical icons may be moved rotationally in a clockwise or counterclockwise direction). After movement of icons 822, one or more of the graphical icons 822 may be different, where the movement of the arrangement of icons 822 enables at least one graphical icon to be rotated beyond the display edge and the one or more previously hidden icons to enter the display area. After movement, the graphical icon located substantially at the center of the pattern may be in a position to enable selection (e.g., the apex of a curved pattern shown). Digital media device 35 may receive a selection of the highlighted icon for at least one media application, service application, or media and service application. The selected media application, service application, or media and service application may be displayed on the television display 32. More specifically, upon receiving a selection of the highlighted icon, digital media device 35 executes programming to provide the service application from gateway device 10 to digital media device 35 via a user premises data communications network (e.g., a wireless or wired communication system).

Upon receiving a selection of the highlighted icon, digital media device 35 executes programming to enable digital media device 35 to provide the media application, service application, or media and service application. Depending on the media application, service application, or media and service application selected, the digital media device may enable a device (e.g., media source 510, etc.), gateway 10, another digital media device communicatively coupled to network 99, to provide the selected application to digital media device 35. Alternatively, upon receiving a selection of a highlighted icon, digital media device 35 may display a screen related to the selected icon to provide access to additional applications and/or services related to the selection. For example, selection of a highlighted icon may display: scratchpad functionality GUI screen illustrated in FIG. 9B; one or more of the backup GUI screens illustrated in FIGS. 10A-10; one or more of the file sharing GUI screens illustrated in FIGS. 11A-11B; and/or one or more of the home automation GUI screens illustrated in FIGS. 12A-12I These screens may, for example, be inserted or overlaid onto a video-type presentation presented on television display 32 (shown in FIG. 2), or may fully occupy the display area of television display 32.

Digital media device 35 may also provide the media application, service application, or media and service application from memory 602 or digital storage device 604 (illustrated in FIG. 3). In addition, digital media device 35 may be enabled to provide the media application, service application, or media and service application received via wireless network interface 650 or wired network interface 660 (illustrated in FIG. 3). The execution of the programming embodied on digital media device 35 may dynamically add or remove one or more graphical icons from the arrangement of graphical icons 822 in the pattern (e.g., the substantially curved pattern shown in FIG. 8A). The dynamic adding or removing of the one or more icons may be, for example, determined by subscriptions to media applications, service applications, or media and service applications. The dynamic adding or removing of the one or more icons may also be provisioned by gateway device 10. Additionally, the dynamic adding or removing of icons may relate to the availability of directories of content hosted by gateway device 10, memory 602 or digital storage device 604 of digital media device 35 or another digital media device connected to network 99, content servers communicatively coupled to network 99, digital storage devices 520, or any other suitable content hosted by devices communicatively coupled to digital media device 35.

Figure 8B:
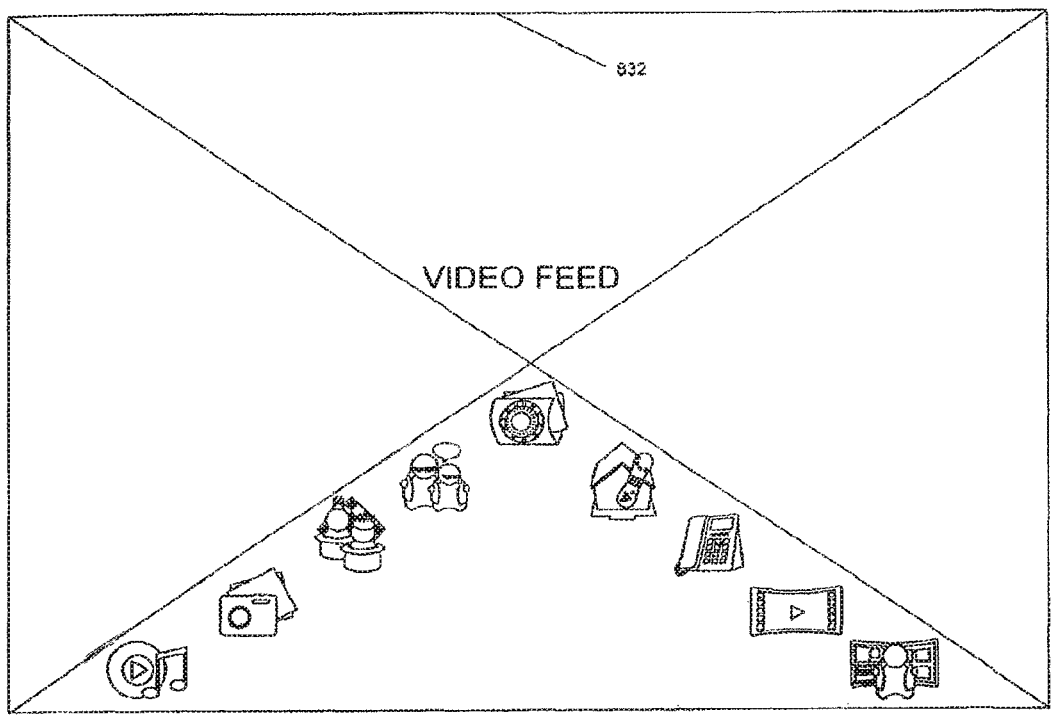
FIG. 8B illustrates a composite image of a graphical user interface depicting icons in a substantially linear arrangement overlaid onto a video display from a media source.

Alternatively, as illustrated in FIG. 8B, graphical icons 830, similar to graphical icons 822 shown in FIG. 8A, may be overlaid on a display screen 832 in a substantially linear arrangement. Icons 822 shown in FIG. 8A or icons 830 shown in FIG. 6B may have either a substantially curved or substantially linear arrangement. A signal from at least one media source may be the primary image on display screen 832, and the arrangement of graphical icons 830 may be a secondary image overlaid onto the primary image 832.

The substantially linear arrangement of graphical icons shown in FIG. 8B may have first end 834 and second end 836, with first end 834 and second end 836 each defined by a display edge of the television display. Each graphical icon 830 may represent a media application, service application, or media and service application. Examples of applications represented by icons include music, video, pictures, home automation, games, phone and messaging, parental control, or any other suitable applications. Some graphical icons 830 may represent media applications that may be provided by a media source such as media source 510, from storage devices 520 (e.g., digital camera 522, flash memory 524, PMP device 526, etc.), or from other devices via interfaces 650, 660, 670, 680 of media device 35. Some graphical icons 830 may represent media applications, service applications, or media and service applications provided via gateway device 10.

Using a remote control or other control device, a user may highlight one of the graphical icons 830 located substantially a center 838 of the substantially linear pattern to enable selection of the one graphical icon. Digital media device 35 may receive a selection from a remote (e.g., remote 550) to move the arrangement graphical icons in a first direction or a second direction (e.g., in the substantially linear pattern shown in FIG. 8A, the graphical icons may be moved in a left or right direction). After movement of icons 830, one or more of the graphical icons 830 may be different, where the movement of the arrangement of icons 830 enables at least one graphical icon to be moved beyond the display edge and the one or more previously hidden icons to enter the display area. After movement, the graphical icon located substantially at the center (e.g., at center 838) of the linear pattern may enable selection. Digital media device 35 may receive a selection of the highlighted icon for at least one media application, service application, or media and service application. The selected media application, service application, or media and service application may be presented on the television display 32 or audio-video system 530. More specifically, upon receiving a selection of the highlighted icon, digital media device 35 executes programming to provide the service application from gateway device 10 to digital media device 35 via a user premises data communications network (e.g., a wireless or wired communication system).

Upon receiving a selection of the highlighted icon, digital media device 35 executes programming to enable digital media device 35 to provide the media application, service application, or media and service application. Depending on the media application, service application, or media and service application selected, the digital media device may enable a device (e.g., media source 510, etc.) or gateway 10 to provide the selected application to digital media device 35. Alternatively, as described above, selection of the highlighted icon may present additional displays presenting selections for applications and/or services related to the selected icon.

The execution of the programming embodied on digital media device 35 may dynamically add or remove one or more graphical icons from the arrangement of graphical icons 830 in the substantially linear pattern. The dynamic adding or removing of the one or more icons may be, for example, determined by subscriptions to media applications, service applications, or media and service applications.

For ease of operation, the gateway device provides a GUI interface that supports functional test, diagnostics and control capabilities for itself and for the other home network devices that it communicates with. The test and diagnostics include connection and bandwidth tests, statistics and alarms (alerts) for use by service support centers and users. The control capabilities include automated configuration and management. To this end, users of gateway device 10.sub.1, . . . , 10.sub.n access the Web/Internet via a personal computer/computing device, mobile or laptop computer, personal digital assistant, or like device implementing web-browser functionality, e.g., Firefox 1.5 and Internet Explorer.®. 6.0 or later, or other browsing technology that may be compatible. In an exemplary embodiment, the browser interface employs the user interaction techniques, e.g., Web 2.0, and implements web development technologies such as AJAX (Asynchronous JavaScript and XML).

Figure 9A:
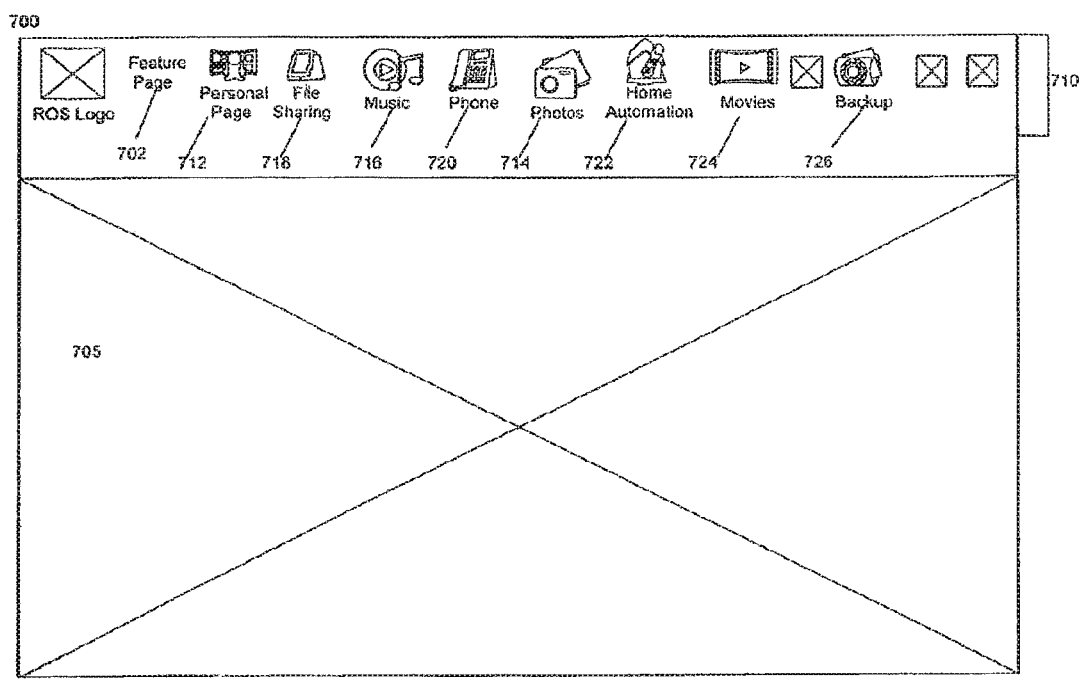
FIG. 9A depicts an example Home screen page 700 for accessing applications and/or services.

With respect to accessing the gateway device 10 and services from service management center 50 via an interface (e.g., web interface, etc.), or accessing media and/or services from devices communicatively coupled to digital media device 35, users may, for example, log-in to a home page screen (not shown) via a web-based communication or other suitable network communication by entering a username and a password. Upon submitting this login information, both the username and password may be validated. If either the username or password is invalid, then an appropriate error message may be displayed explaining the nature of the error. If the login is successful, and the gateway appliance has already been initialized, a user's personal page will be loaded by default which page is user is configurable. For purposes of illustration, a user "Home Center" screen is displayed as shown in FIG. 9A that depicts an example administrator's page 700. Common to any page may be header 702, where a title of the screen is indicated, a content display area 705, and, a system's status indication displayed indicating the present functional capability of the system. A tooltip functionality may be provided for more details regarding system status. If the status is, for example, red, the user can select the status indicator to get a diagnostic screen with a network map (not shown). This screen may display the current status of all devices managed by the gateway appliance and includes a button to allow the user to test the current status. A top bar may also be used to indicate the progress status of any backup jobs currently running. A tooltip may be provided to indicate the schedule name and the progress percentage. The top bar may also indicate the space usage of the user. A tooltip may be provided to indicate the percentage of the space used by the user of the allocated space configured by the administrator user. Various labels may be provided that display the current user information (e.g., administrator), and a link to logout of the home center, or other suitable labels. When the user selects the logout link, the users' web session will be invalidated and the login page will be displayed. Additional links may be provided to change the user preferences. For example, when the user selects the "Preferences" link, a dialog box may be displayed to enable the user to change the user preferences settings such as color, font, themes, or any other suitable preference settings.

A list of home center icons 710 may be arranged on the header. When the user selects an icon, the content area 705 may be replaced with the content selected feature. If a particular feature is not available, the icon will be grayed. If the feature represented by the icon is not available, then the icon may be, for example, grayed and a tooltip may be provided to display an explanation. Although not shown, notifications for each feature may be displayed as an icon, which may be animated, below that feature in the second bar. A tooltip is provided with more details for each notification. When the user selects the notification icon, detailed notification information may be displayed.

As shown in FIG. 9A, the list of user-selectable tabs or icons may be provided that enable user interactivity with the services provided by the gateway appliance or other device communicatively coupled to digital media device 35. These icons include, but are not limited to: a Personal Page icon 714 that displays the personal page allowing a user to organize and configure a set of useful "widgets" provided by the gateway device; a Photos icon 714 that displays a photos page allowing a user to browse stored images; a Music icon 716 that displays a music page allowing a user to browse music stored; a File Sharing icon 718 that displays a file sharing page allowing a user to view and manage the shared files with buddies; a Calendar icon 724 that displays a calendar page allowing a user to manage their own calendar; a Phones icon 720 that displays a "phones" page allowing a user to view and manage the list of voicemail and call logs stored at the gateway appliance; a Backup icon 726 that displays a backup page allowing a user to view and manage the backups managed by the gateway appliance, and, a Home Automation icon 724 that displays a home automation page allowing a user to view and manage the home automation devices.

Backup Services GUI

Figure 10A:
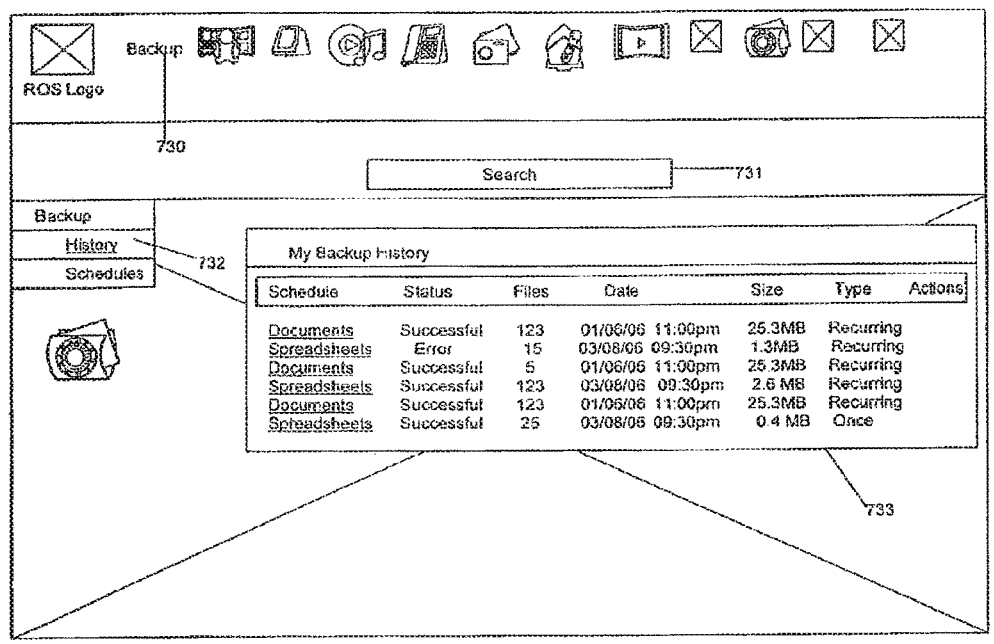
FIGS. 10A-10D depict exemplary GUI screen pages for accessing backup services functionality.

As shown in FIG. 9A, upon selection of the Backup icon 726, backup page 730, as shown in FIG. 10A, may be displayed. The backup page may enable a user to view and manage the backups managed by, e.g., the gateway appliance. A title bar of the content area may display the total number of backups performed by the gateway appliance, or any other related information. Search box 731 may be provided to enable the user to find any files that have been backed up. Each matched file may be displayed in a list with substantially all related metadata. The submenu on the right provides options for the user to access the backup history and schedules.

As shown in FIG. 10A, via backup page 730, in response to selecting a History option 732, a list or pop-up display may be generated to display the backup history data in a table with the following exemplary columns: 1) Schedule—the name of the backup schedule. When the user clicks on the name, a backup schedule screen will be displayed; 2) Status indicator—the status of the backup; 3) Files—the number of files that were backed up; 4) Date—The date and time the backup was done. When the user selects the date, the backup details may be displayed to enable the user to view the list of files that were backed up; 5) Size—the total size of the files that were backed up; 6) Type—the type of backup, e.g., Recurring-full backup of all files every time the backup runs, or, Once-immediate backups; and 6) Actions—the actions that can be done on each backup. When the user clicks on the restore icon, all of the files in the backup will be restored to their original location.

Figure 10B:
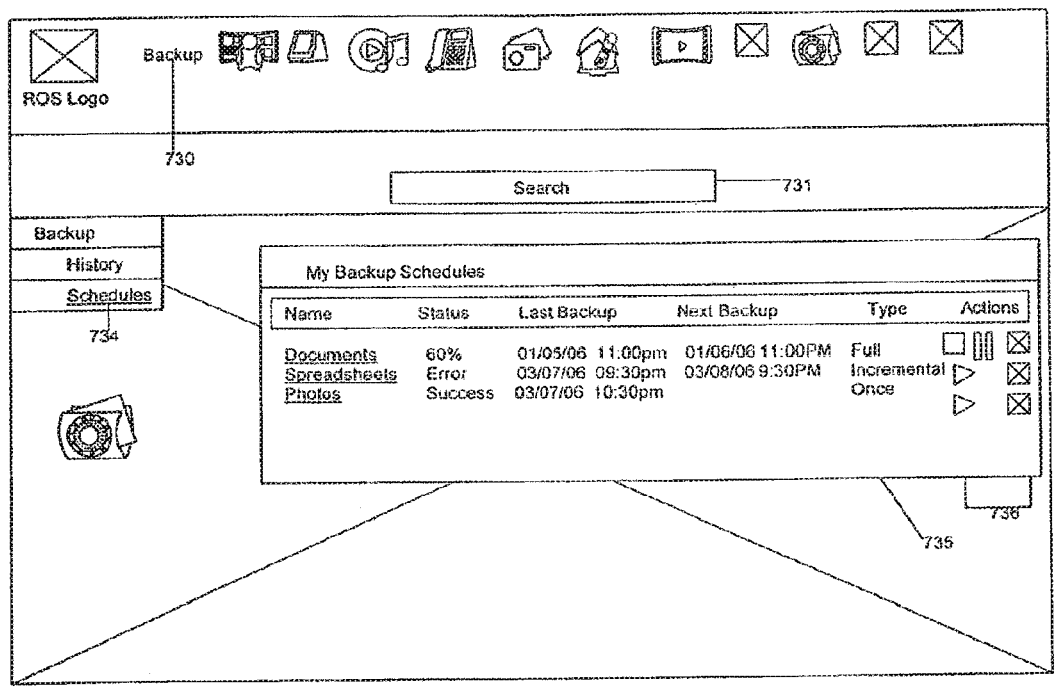

As shown in FIG. 10B, via backup page 730, in response to selecting a Schedules option 734, a list or pop-up display 735 may be generated to display the total number and types of scheduled backups. The content area lists the schedule data in a table with the an exemplary columns having the name of the backup schedule, or other exemplary columns. When the user clicks on the name, the schedule details will be displayed so that the user may modify the schedule; the Status indicator—the status of the backup. For a backup in progress, a dynamic progress bar and percentage indicator will be displayed; the Last Backup—the date and time of the last backup for this schedule; the Next Backup—the date and time of the next backup for this schedule; the Type—the type of backup, e.g., a recurring or full backup of all files every time the backup runs, or immediate backups, a single back-up or an incremental backup; and, the Actions that may be done on each schedule as implemented by selecting an icon from a group 736 of icons, e.g., a Stop icon, which, when selected, stops the current backup in progress. When the user selects the stop icon, the user may be prompted to keep the files that have already been backed up; Pause/Start-pause the current backup in progress or start a backup that is not in progress; a Report icon which when selected, displays a report of the backup (report screen design); and, an icon for deleting the schedule. When the user selects the delete icon, the user will be prompted to confirm the delete operation; and, an immediate Backup (i.e., backup now) option.

Figure 10C:
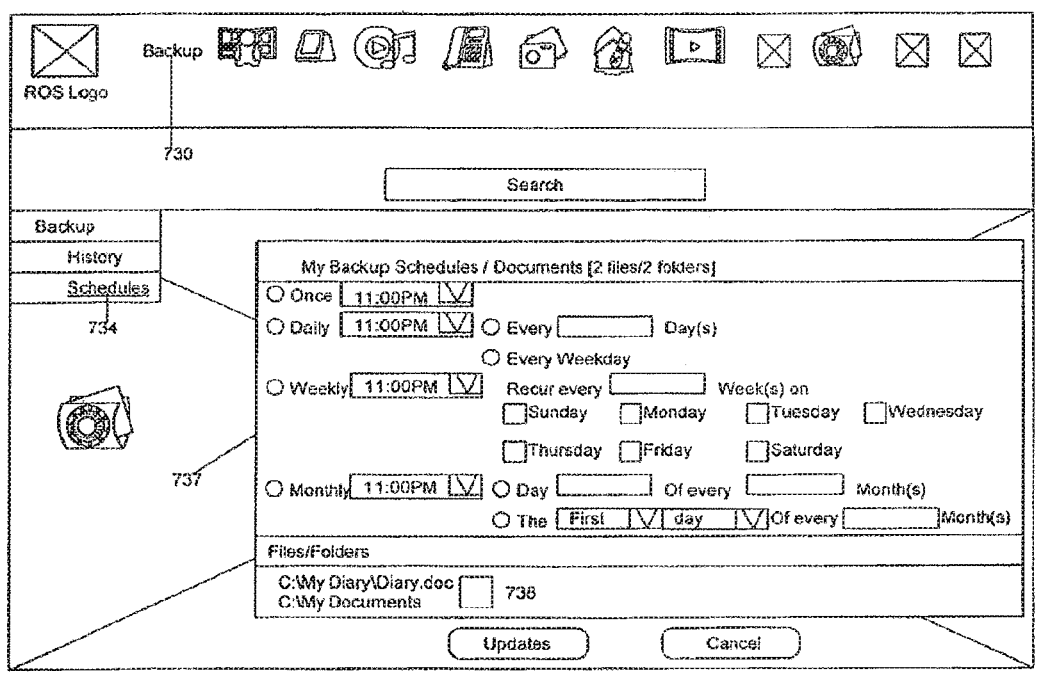

FIG. 10C depicts the resulting backup schedule screen 737 resulting from selection of the "documents" backup name from the display depicted in FIG. 9A. Via this display, functionality may be enabled for the user to edit an existing schedule for each of the files and folders 738 managed by the schedule as displayed. The content area displays the current schedule information. However, the user may change the schedule settings and select the Update button to modify the schedule. Particularly, the user may: change the list of files for the schedule; clone and modify an existing schedule; and/or change the list of files. It is understood that the file backup feature may be additionally integrated with use of a Calendar application. The user may additionally select the Cancel button to return to the list of scheduled backups.

Figure 10D:
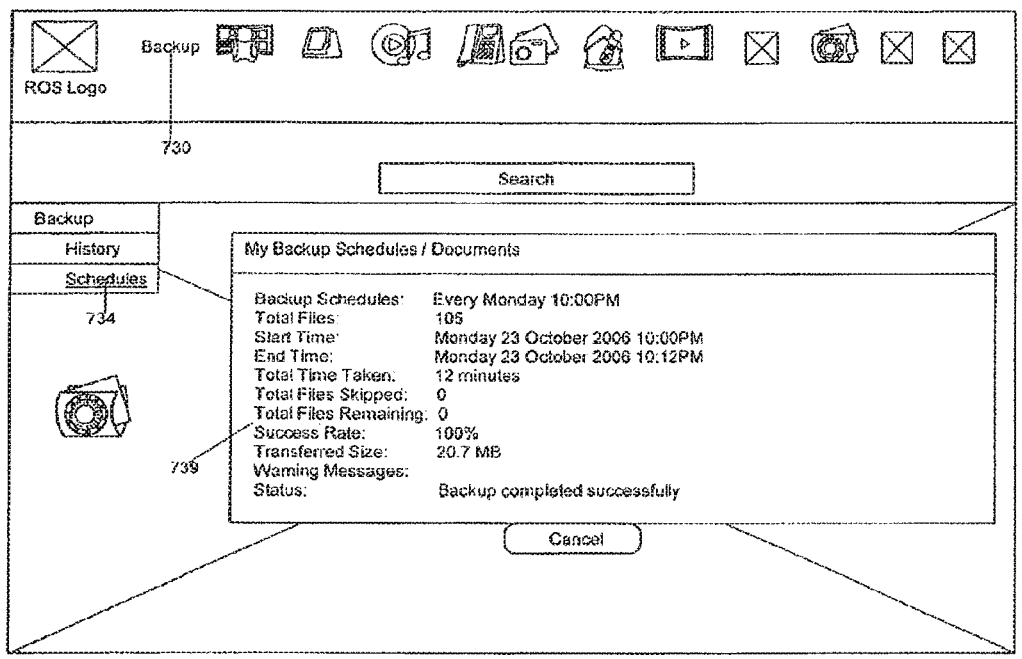

FIG. 10D depicts the resulting backup report display 739 resulting from selection of the Report action icon from the screen depicted in FIG. 10B. This enables the user to view a status report of a backup schedule with the content area displaying the status information about the backup job.

Filesharing Services GUI

Figure 11A:
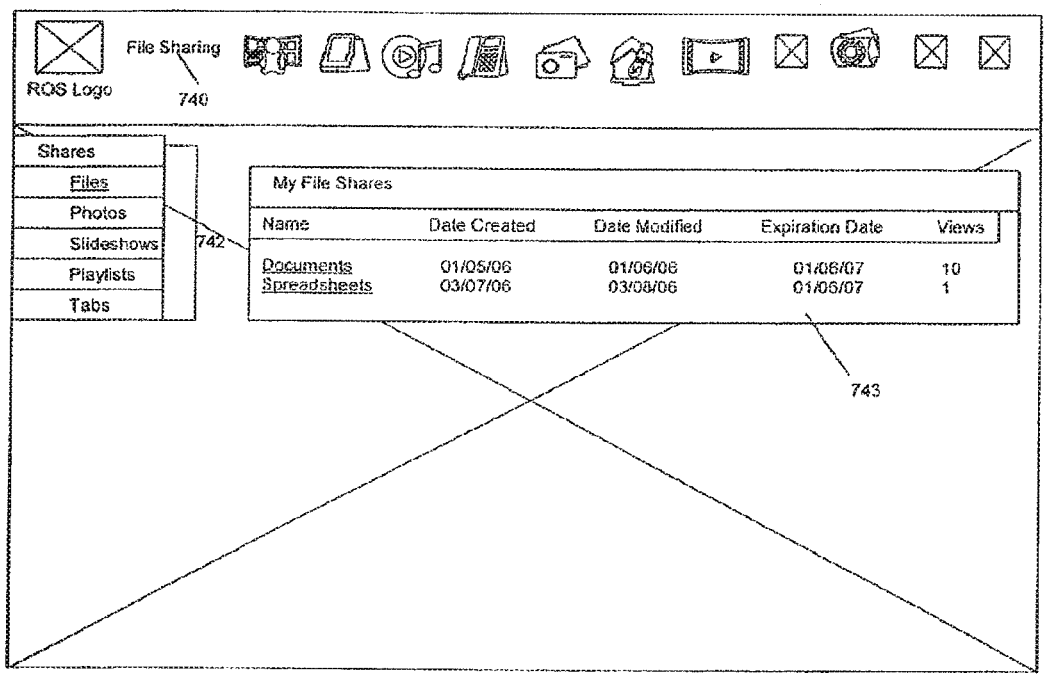
FIGS. 11A-11B depict exemplary GUI screen pages for accessing appliance file sharing services functionality.

Returning to FIG. 9A, upon selection of the FileSharing icon 718, exemplary filesharing page 740 may be displayed, as shown in FIG. 11A. The filesharing page enables a user to view and manage the shared files (shares) with buddies. The shares may grouped by the following exemplary types: files, photos, slideshows, playlists, tabs, etc. The submenu 742 may enable the user to view the list of shares of each type. As shown in FIG. 11A, the shares may be displayed as a list 743 including, but not limited to the name (e.g., documents), date created, date modified, expiration date and number of views for each share are displayed. The shares may be sorted by each column by, for example, selecting the header label for that column. The total number of shares of each type may be displayed in the title bar of the content area (in displayed list 743). FIG. 11A depicts an example screen display showing file type shares displayed in list 743. The user may be additionally enabled to delete a share, e.g., by clicking on a "delete" icon (not shown). For example, by moving a mouse or other graphical control device over a share name, an icon may be displayed that allows the user to delete the share. The user can view the files that make up the share by selecting the name link for each share.

Figure 11B:
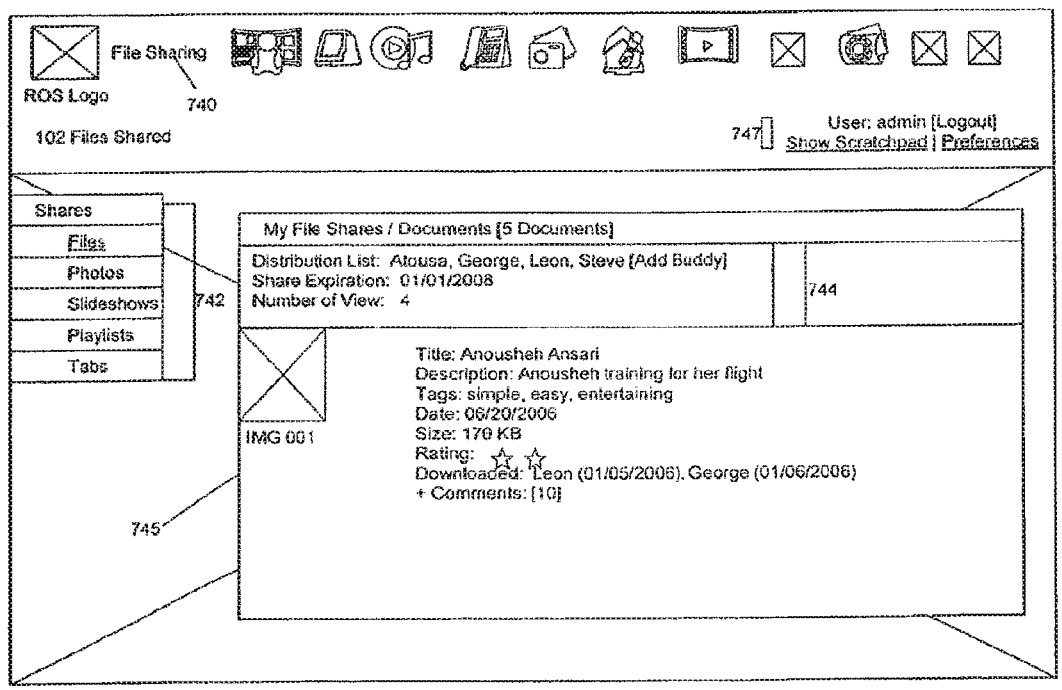

Continuing to FIG. 11B, upon selection of the shares name, e.g., documents, via example page 740 shown in FIG. 11A, there is displayed a list 745 of files of that shared file type, e.g., documents. The files and folders in the share are displayed as a list and include a thumbnail, file name, title, description, tags, date, size, buddy rating (which buddies downloaded the file and when), and the total number of comments added by buddies are displayed. The title, description and tags can be modified by inline editing. For folders, users can drill into the folder item and then see the list of files shared in that folder. The buddies that make up the distribution list for the share may be displayed individually as shown in content area 744. Each buddy that has not viewed the share is highlighted. When a cursor is moved over a buddy name, an icon is displayed next to the name providing functionality to remove that buddy from the distribution list. There is a link next to the list of names to add a new buddy. When the user selects the Add Buddy link, a list of other buddies may be displayed. The user may select which buddies to add from the list. The expiration date of the share is additionally displayed. The user can change the expiration date using inline editing. Upon moving a displayed mouse cursor over an item, an icon is displayed to allow the user to remove the item from the share. An icon is displayed next to the number of comments. When the user selects the icon, the list of comments may be displayed inline below the metadata of the shared file. The user may collapse the comments by selecting the icon again.

Scratchpad GUI

Additional functionality may be implemented (e.g., adding items to the share) by using a scratchpad which functions as a visual clipboard to collect items which are used at a later time. To display the scratchpad, the user may select the Show Scratchpad link 747 in the header shown in example display of FIG. 11B. Any items in the scratchpad can then be drag-and-dropped onto the list of items, or selected in any other suitable fashion, to add them to the share.

Figure 9B:
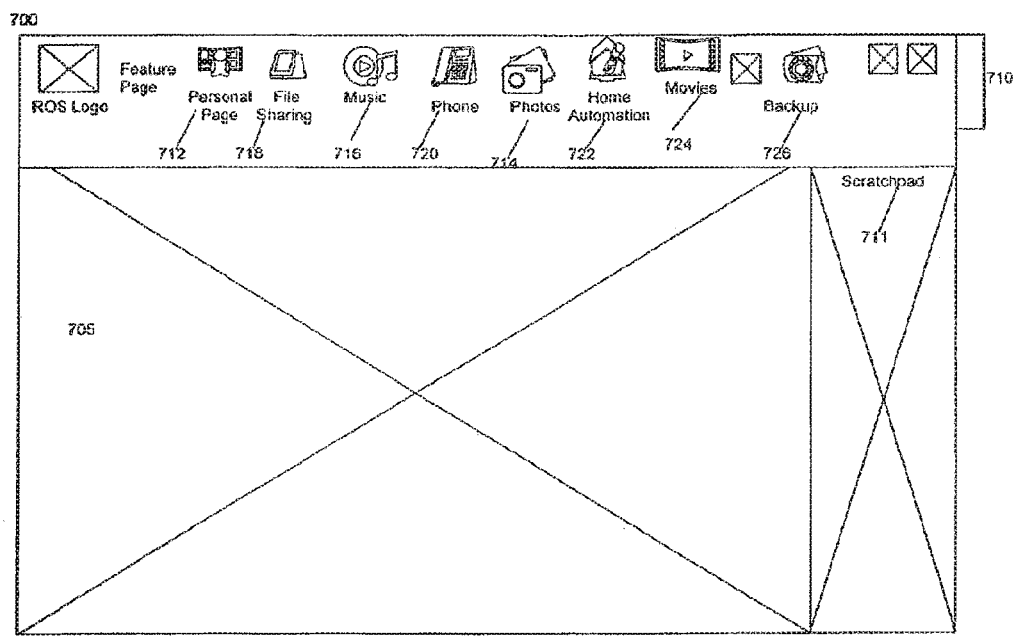
FIG. 9B depicts an example GUI Home Screen page 700 for accessing scratchpad functionality.

With respect to use of the scratchpad, as shown in FIG. 9B, a Show/Hide Scratchpad link may be provided to display the scratchpad (e.g., on the right side of the header). When the user selects the Show Scratchpad link, a scratchpad area may be displayed on the right of the content area. The scratchpad may have window controls to maximize and minimize its content area. Users may then drag-and-drop items from the content area 705 onto the scratchpad area, or select them for the content area 705 in any other suitable manner. Items may also be added on other devices such as a TV, where the TV may be used to flag such an item. Any operations on the items in the scratchpad may be performed from the web GUI. Items may be displayed as thumbnails with metadata. When the user moves a cursor over the thumbnail, a tooltip may be provided with the details for that item. In addition, each item in the scratchpad may have a link to remove it from the scratchpad.

Items in the scratchpad can be grouped into collections and the total files size of the items in each collection is displayed. By default, there is a collection called "My Collection". The user may change the name of the collection by using inline editing. When the user selects the New Collection link 711, a new collection boundary may be added to the bottom of the scratchpad. Users may move items between collections by using drag-and-drop functionality, or other suitable functionality. Each collection may have a link to remove it from the scratchpad. When the user right clicks on a collection, a context menu may be displayed providing an option for sharing the files in the collection. A dialog (not shown) may be presented that displays the list of buddies to share with. A right-click context menu (not shown) additionally allows the user to save the collection as a slideshow, photo album or as a music playlist depending on the type of items in the collection.

Home Automation Services GUI

Figure 12A:
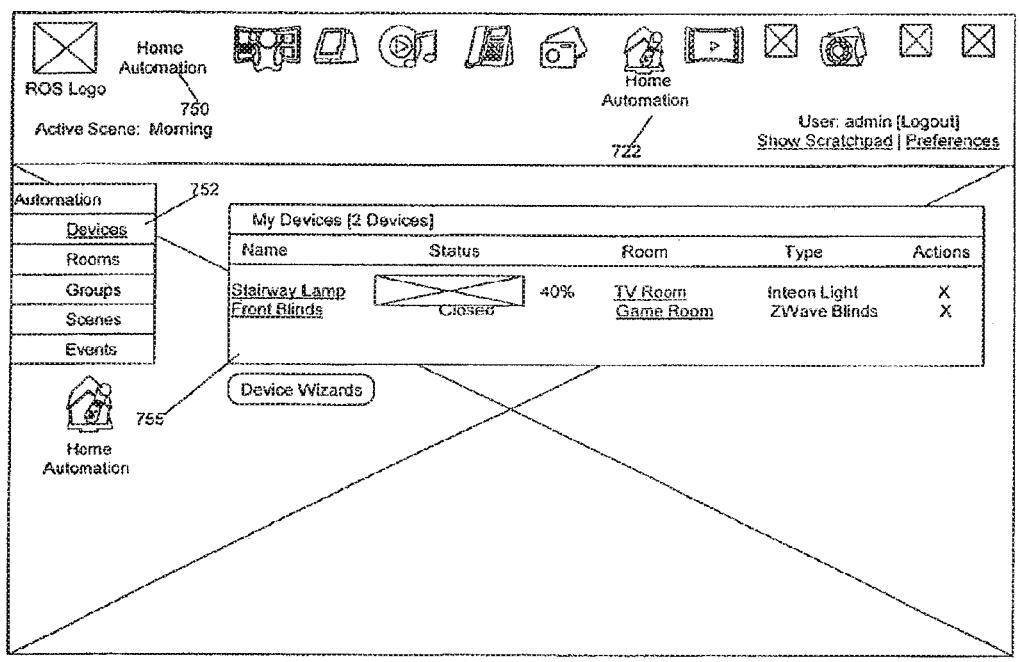
FIGS. 12A-12I depict exemplary GUI screen pages for accessing appliance home automation services functionality.

Referring back to FIG. 9A, upon selection of the Home Automation icon 724, a home automation page may be displayed, such as the example home automation screen 750 shown in FIG. 12A, that enables users to view and control all of the devices managed by the gateway appliance, or, alternatively, manage devices communicatively coupled to digital media device 35. As shown in FIG. 12A, in response to selecting a devices option 752 via home automation page 750, a list or pop-up display 755 may be generated to display the following for the controlled devices: 1) the user defined name for the device. After the devices are automatically detected, the gateway appliance will default the name to the type. The user can modify the name by using inline editing; 2) a Status indicator icon or label indicating the current status and possible value of the device; 3) a user defined room in which the device is located. When the devices are automatically detected, the default room will be the empty however, the user can change the default room by using inline editing; 4) the manufacturer and type of device; and, 5) any actions that can be done on each device.

Figure 12B:
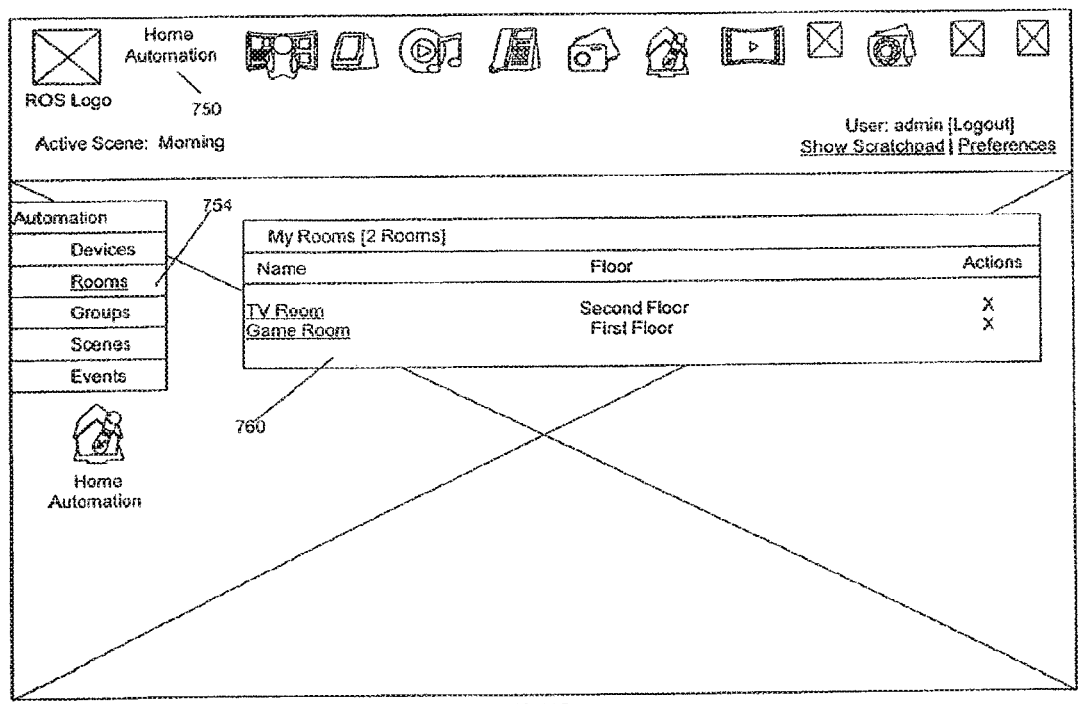

As shown in FIG. 12B, in response to selecting a rooms option 754 via home automation screen 750, a list or pop-up display 760 may be generated to allows the user to view and design one or more the rooms in the house. A total number of rooms may be displayed and an icon may be provided that enables the user to add a new room to the list. When the user selects the add icon, a new room screen may be displayed. The content area lists the rooms in a table with the following exemplary columns: 1) a user defined name for the room. The user can modify the name by using inline editing; and, 2) the floor on which room is located. The user can change the default room by using inline editing; and, 3) the actions that can be done on each room, e.g., delete the room. When the user moves a cursor over each room in the table, the room plan is displayed inline.

Figure 12C:
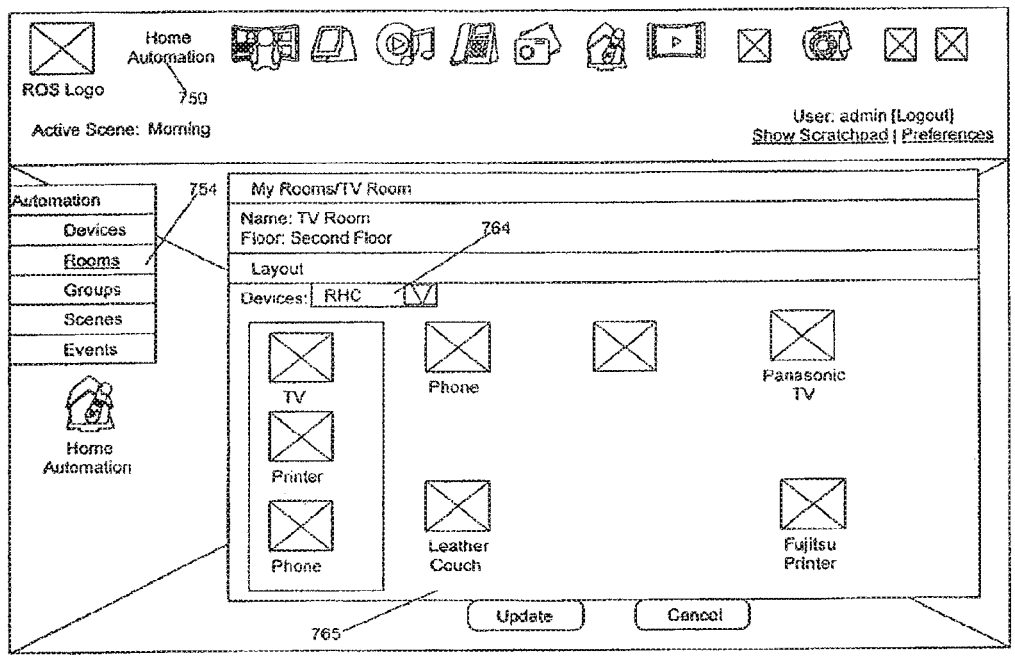

As shown in FIG. 12C, via home automation screen 750, a user may edit an existing room. The content area thus displays the current room name and floor that the user can edit to change. As shown in FIG. 12C, the content area may display the layout editor 763 for the room that includes a list of icons for devices that can be drag-and-dropped on a work area for that room. The devices are grouped into categories that may be selected from a drop-down menu 764. When a category is selected, the icons for that category may displayed in the list. Once an icon is dropped onto the work area 765, it may be moved around, for example, using direct manipulation and be labeled by using inline editing. An icon can be removed from the work area by using the delete option from the right-click menu or by dropping it outside of the work area (e.g., by using the remote control 550). Each icon may have a status indicator to see the current status of the device if it is managed by the gateway appliance. The user may change the room settings and press an update button to modify the group.

Figure 12D:
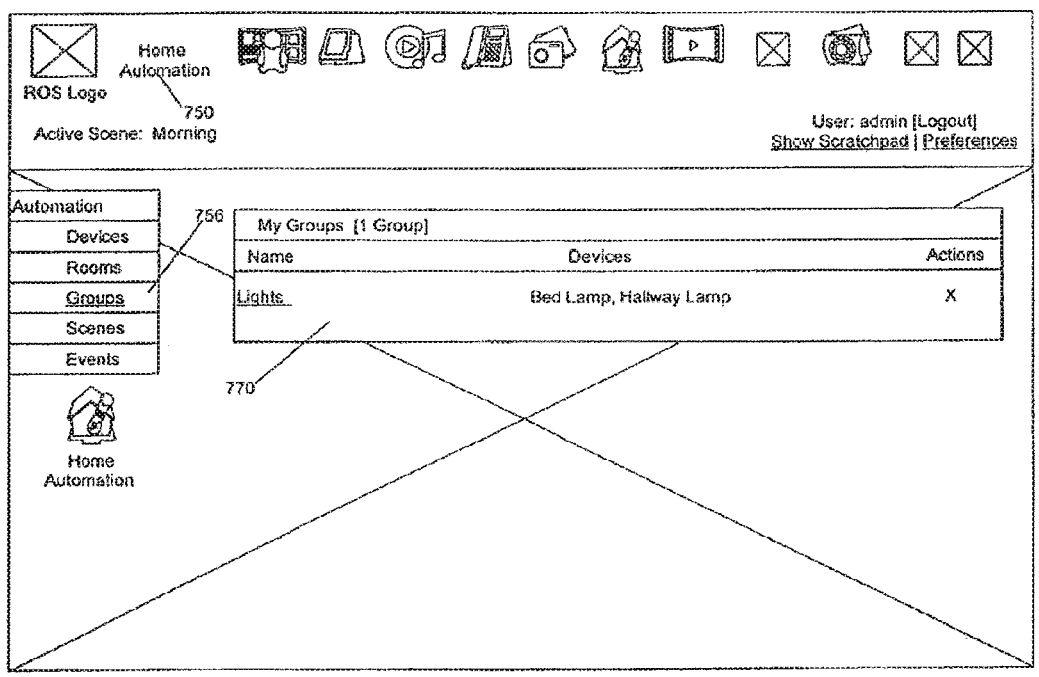
Figure 12E:
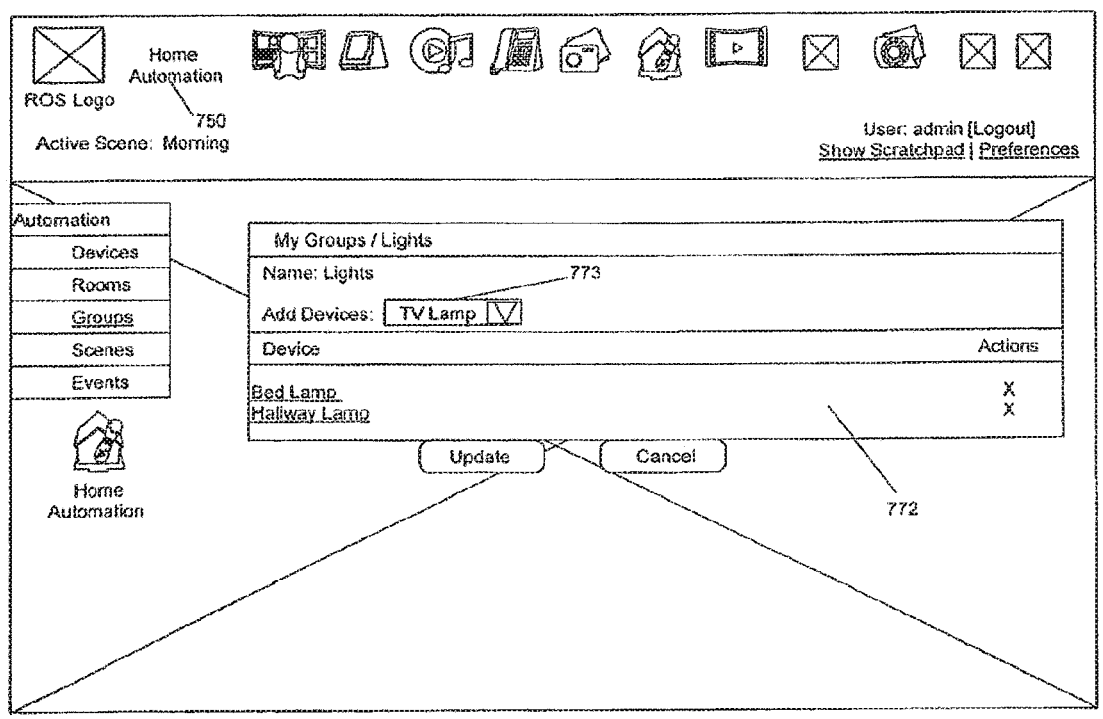

As shown in FIG. 12D, via home automation screen 750, a user may view and control a plurality of the groups of devices created by the user upon selection of the group menu option 756. When the user selects the name for a device, the settings for that group will be displayed. An icon is displayed to allow the user to add a new group to the list. When the user clicks on the add icon, the new group screen will be displayed such as shown in FIG. 12E. Particularly, in FIG. 12D, the content area provides a list of the groups in a table 770 having the following columns: 1) the user defined name for the group which can be modified; 2) the list of devices that make up the group, and 3) Actions—the actions that can be done on each group.

In FIG. 12E, the home automation group screen may enable the user to edit an existing group. The content area may display the current group name and the list of devices 772. The user can use inline editing to change the group name. An Add Device drop-down menu 773 allows the user to select a new device to add to the list. When the user clicks on the add icon, the device will be added to the list of devices that display the names of the devices. The actions column allows the user to delete a device from the list. When the user clicks on the delete icon, the user will be prompted to confirm the delete operation. The user may change the group settings and select an Update button to modify the group or select the Cancel button to return to the list of groups screen.

Figure 12F:
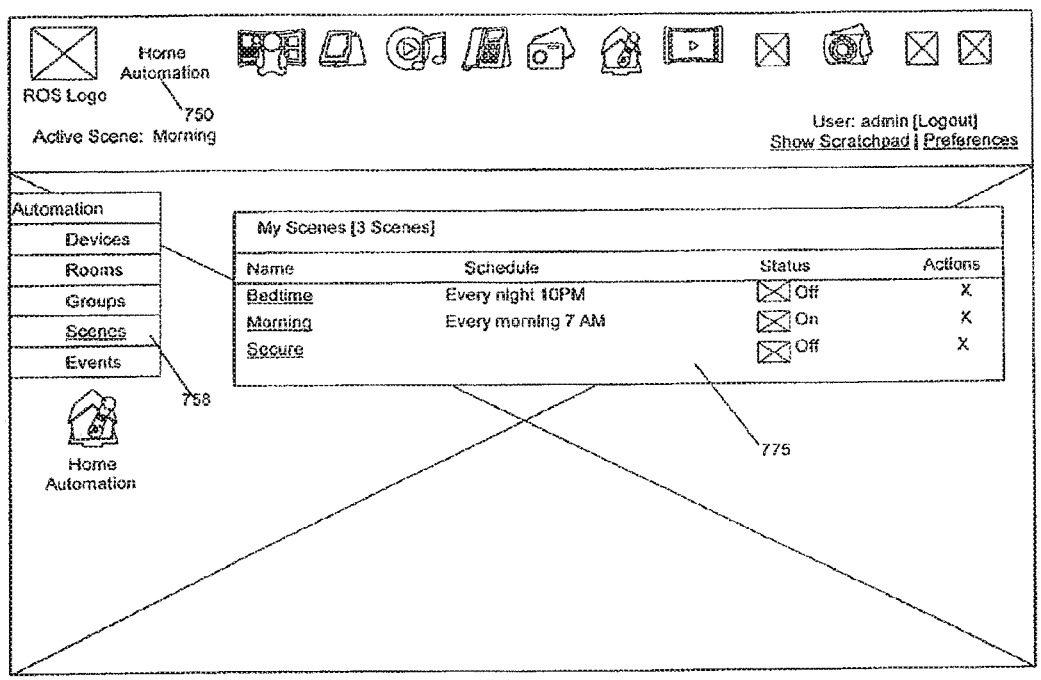

As shown in FIG. 12F, via home automation screen 750 a user may view and control one or more scenes created by the user upon selection of the scenes menu option 758. Generally, upon selection of the scenes menu option 758, the total number of scenes, for example, is displayed via the list 775 shown in FIG. 12F. An icon is displayed to enable the user to add a new scene to the list via functionality implemented via the example GUI shown in FIG. 12G. When the user selects the add icon, the new scene screen may be displayed. The content area 775 lists the scenes in a table with the following exemplary columns: 1) the user defined name for the scene. The user can modify the name by using inline editing; 2) the schedule to activate the scene, if defined; 3) the current status of the scene, e.g., either On or Off. The user can click the icon to toggle the status of the scene; and, 4) the actions that can be performed on each scene.

Figure 12G:
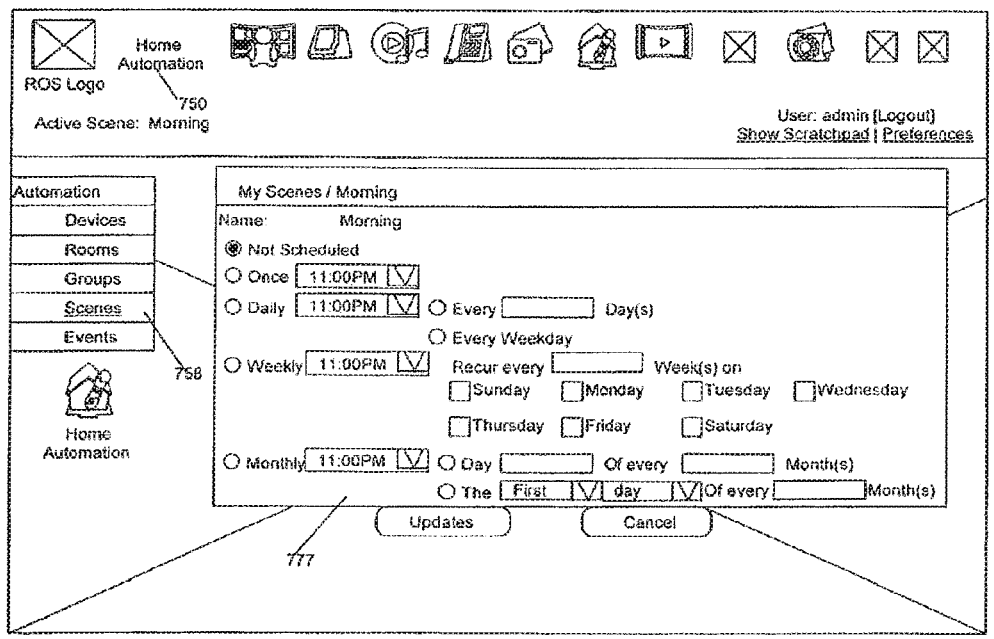

In FIG. 12G, the home automation group screen may enable the user to edit an existing scene. The content area 777 displayed may present the current scene name and schedule. The user may utilize, for example, inline editing to change the scene name, e.g., "morning", change the scene settings and/or select the Update button to modify the scene. The user may select the Cancel button to return to the list of scenes screen.

Figure 12H:
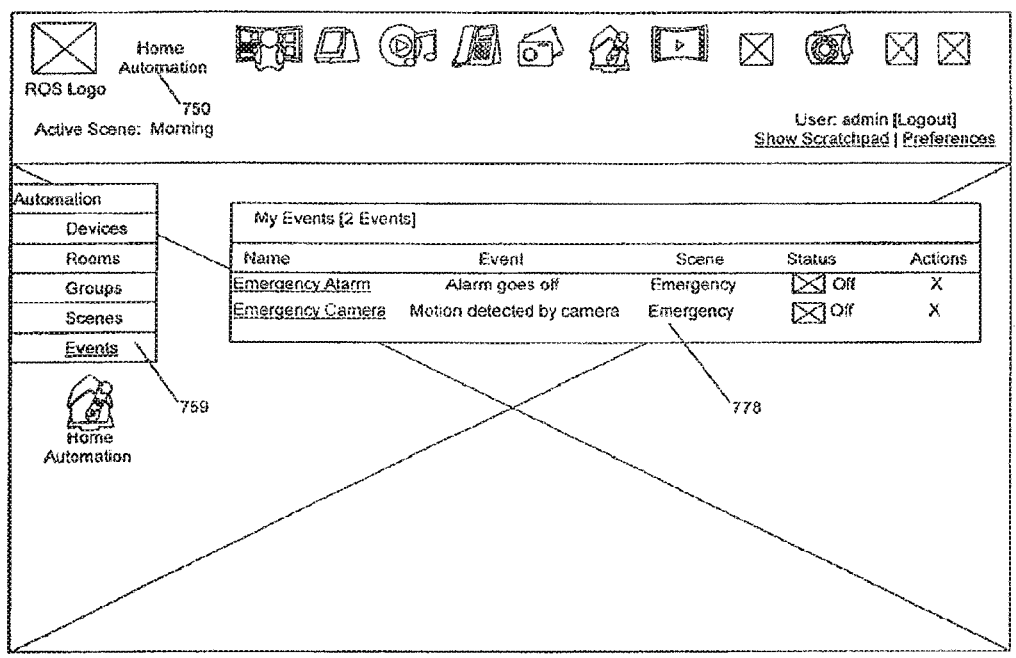

As shown in FIG. 12H, via home automation screen 750 a user may view and control all of the events generated by the gateway appliance. In the exemplary screen display shown in FIG. 17H, the total number of events may be displayed. An icon may be displayed to allow the user to add a new event to the list. When the user selects the add icon, a new event screen is displayed for user configuration. The content area lists the events in a table 778 with the following columns: the user defined name for the event; the automation event; the scene to be invoked for the event. A hyperlink may be provided to the scene screen; the current status of the event, e.g., either On or Off. The user may test the event mapping by selecting the icon to toggle the status of the scene; and, the actions that can be done on each event.

Figure 12I:
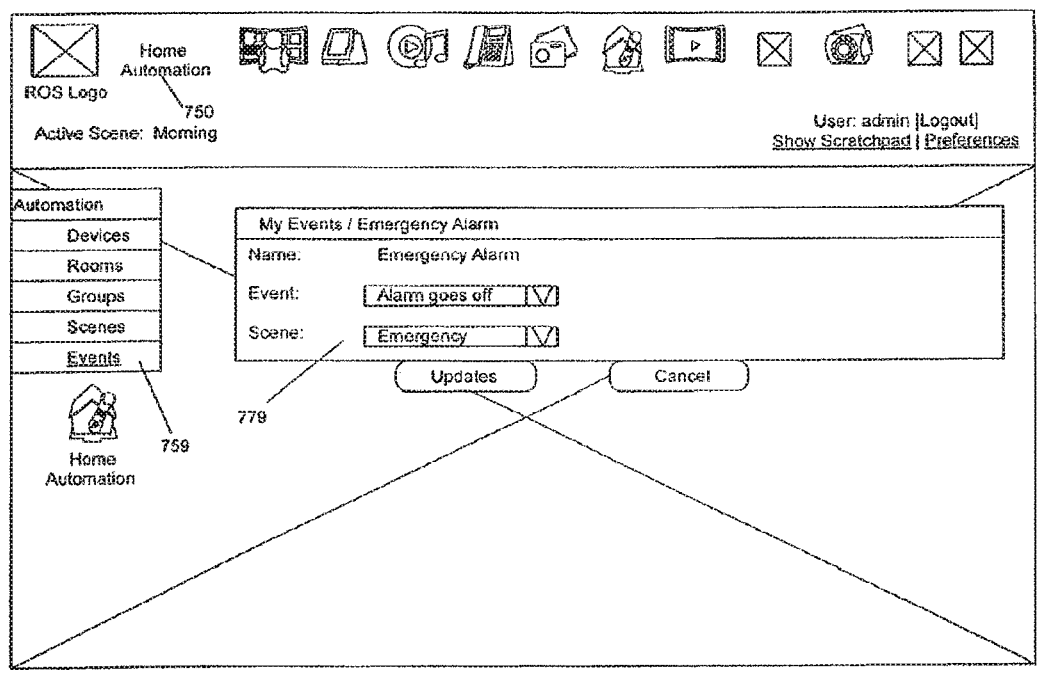

As shown in FIG. 12I, the home automation group screen may allow the user to edit an existing event. The content area displays a list 779 providing the event name, automation event and scene. The user may, for example, use inline editing to change the scene name, or change the event settings and select the Update button to modify the event. The user may select the Cancel button to return to the list of events screen.

Program aspects of the technology may be thought of a "products," typically in the form of executable code and/or associated data for implementing desired functionality, which is carried on or embodied in a type of machine readable medium. In this way, computer program instructions may be provided to a processor of a general purpose computer, special purpose computer, embedded processor or other programmable data processing apparatus to produce a machine, such that the instructions, which execute via the processor of the computer or other programmable data processing apparatus, so as to implement functions described above.

Terms regarding computer or machine "readable medium" (or media) as used herein therefore relate to any storage medium and any physical or carrier wave transmission medium, which participates in providing instructions or code or data to a processor for execution or processing. Storage media include any or all of the memory of the gateway device or associated modules thereof or any of the hardware platforms as may be used in the service management center, such as various semiconductor memories, tape drives, disk drives and the like, which may provide storage at any time for the software programming. All or portions of the software may at times be communicated through the Internet or various other telecommunication networks. Such communications, for example, may enable loading of the software from one computer into another computer, for example, from the updater 51*a* hardware platform for a gateway device 10 or from another source into an element of the service management center 50. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. Hence, the broad class of media that may bear the instructions or data encompass many forms, including but not limited to, non-volatile storage media, volatile storage media as well as carrier wave and physical forms of transmission media.

Those skilled in the art will recognize that the teachings of this disclosure may be modified, extended and/or applied in a variety of ways. An extension of the system architecture, for example, provides the ability of various and disparate third-party application service providers to provide multiple application services independently. Application services are managed by the "managed" service provider through the service management center 50, meaning, generally, authorizing, provisioning, and monitoring the usage of a particular application service. This can be accomplished in a variety of ways with varying degrees of involvement of, or coordination with, the service management center. The service management center 50 could manage these items "soup-to-nuts" or have minimal involvement. For example, the service management center 50 could deal directly with the third-party service provider to acquire application services at the request of a user and manage the delivery, authorization, usage-monitoring and upgrading of the application service. At the other end of the spectrum, the managed service provider may have arrangements with the third-party application service provider by which orders or requests from the users may come directly to the third-party application service provider, and services are delivered to the user by the third-party service provider who in turn coordinates with the managed service provider to register and monitor the particular application service placed in the gateway device 10. It should be noted that this ability to manage application services extends through the gateway device into the end-point devices registered or associated with the gateway or network.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The invention claimed is:

1. A digital media device, comprising:
   at least one processor; and
   memory having instructions that, when executed by the at least one processor, configures the digital media device to
   communicate, via a wide area network, with a management center, and enable user management of one or more subscriptions managed by the management center,
   receive user input,
   cause a graphical interface to be displayed, the graphical interface is configured to provide access to a plurality of icons representing media applications that enable access to media based on the received user input, the media applications include—
      a locally stored first media application associated with first media available from a first service provider, the first media application locally manages at least one of first authentication information or a first key used by the first service provider to authorize access to the first media application, the first media, or both, wherein the digital media device stores the at least one of first authentication information or first key,
      in response to the local authentication, sending a request for streaming the selected first media from the first service provider to the digital media device,
      a locally stored second media application associated with second media available from a second service provider, the second media application manages at least one of second authentication information or second key used by the second service provider to authorize access to the second media application, the second media, or both, wherein the digital media device stores the at least one of second authentication information or second key, and
      in response to the local authentication, sending a request for streaming the selected second media from the second service provider to the digital media device.

2. The digital media device of claim 1, wherein the digital media device is programmed to display, via a display, a composite image including a media image and icons representing a plurality of sources of media, wherein the digital media device is configured to establish bi-directional communication with each source of media via the wide area network.

3. The digital media device of claim 1, wherein the digital media device is programmed to display, via a display, a composite image including a media image and icons representing a plurality of sources of media, wherein the digital media device automatically establishes bi-directional communication with each source of media.

4. The digital media device of claim 1, wherein the memory has
a billing manager, and
subscription instructions that enable management of subscriptions for the media applications.

5. The digital media device of claim 1, wherein the received user input includes subscription information.

6. The digital media device of claim 1, wherein the memory has a voice processing module and at least one user application service for interactive voice response functionality.

7. The digital media device of claim 1, wherein the memory has instructions that, when executed, enable speech detection.

8. The digital media device of claim 1, wherein the first media application is configured to enable the first service provider to authorize, based at least in part on the at least one of first authentication information or a first key, streaming to the digital media device independent of authorization, based at least in part on the manages at least one of the second authentication information or the second key, by the second service provider to stream to the digital media device.

9. The digital media device of claim 1, wherein the instructions, when executed, cause the digital media device to provide the at least one of the first authentication information or the first key to enable service authorization by the first service provider.

10. The digital media device of claim 1, wherein the instructions, when executed by the at least one processor, cause the digital media device to manage key exchanges.

11. The digital media device of claim 1, wherein the digital media device is communicatively coupled to a display screen.

12. The digital media device of claim 11, wherein the display screen is a television screen.

13. The digital media device of claim 1, wherein the memory includes instructions to provide parental control functions.

14. A digital media device, comprising:
at least one processor; and
memory having instructions that, when executed by the at least one processor, configures the digital media device to
communicate, via a wide area network, with a management center, and enable user management of one or more subscriptions,
receive user input,
cause a graphical interface to be displayed, the graphical interface is configured to provide access to a plurality of icons representing media applications that enable access to media based on the received user input, the media applications include—
a locally stored first media application associated with first media available from a first service provider, the first media application is configured to manage locally stored first data for authorizing access to the first media application, the first media, or both before sending a request for streaming the selected first media from a first server associated with the first service provider, wherein the first data includes authentication/verification data and/or keys associated with the first service provider, and
a locally stored second media application associated with second media available from a second service provider, the second media application is configured to manage locally stored second data for authorizing access to the second media application, the second media, or both before sending a request for streaming the selected second media from a second server associated with the second service provider, wherein the second data includes authentication/verification and/or keys associated with the second service provider.

15. The digital media device of claim 14, wherein the digital media device is configured to
manage at least one first subscription for the first media application independent of at least one second subscription for the second media application, and
display icons representing the first media based on the at least one first subscription.

16. The digital media device of claim 14, wherein the digital media device is configured to
move the application icons along a display of an electronic display in response to receiving one or more signals from a remote control;
display content media for one of the media applications selected via the remote control; and
deliver media, selected via the remote control, from the digital media device to the electronic display.

17. The digital media device of claim 14, wherein the memory has instructions that, when executed, configure the digital media device for speech detection.

18. The digital media device of claim 14, wherein the memory has instructions that, when executed, configure the digital media device for authentication by one of the first or second service providers.

19. The digital media device of claim 14, wherein the first data is provided to the first service provider for authorizing streaming.

20. The digital media device of claim 14, wherein the first media application is configured to enable the first service provider to authorize a streaming service based at least in part on the first data and the authorization is independent of service authorization, based at least in part on the second data, by the second service provider.

21. The digital media device of claim 14, wherein the instructions, when executed by the at least one processor, provide user premises side authentication of one or more services and key exchanges with one or more local endpoint devices.

22. The digital media device of claim 14, wherein the digital media device is integrated with a television system.

23. The digital media device of claim 14, wherein the digital media device is communicatively coupled to a display screen.

* * * * *